US012570749B2

(12) United States Patent
Hauskins et al.

(10) Patent No.: US 12,570,749 B2
(45) Date of Patent: Mar. 10, 2026

(54) ANTI-IDIOTYPIC ANTIBODIES TO GPRC5D-TARGETED BINDING DOMAINS AND RELATED COMPOSITIONS AND METHODS

(71) Applicant: Juno Therapeutics, Inc., Seattle, WA (US)

(72) Inventors: Collin Hauskins, Seattle, WA (US); Kimberly Harrington, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 948 days.

(21) Appl. No.: 17/781,358

(22) PCT Filed: Dec. 4, 2020

(86) PCT No.: PCT/US2020/063497
§ 371 (c)(1),
(2) Date: May 31, 2022

(87) PCT Pub. No.: WO2021/113780
PCT Pub. Date: Jun. 10, 2021

(65) Prior Publication Data
US 2023/0192869 A1 Jun. 22, 2023

Related U.S. Application Data

(60) Provisional application No. 63/061,757, filed on Aug. 5, 2020, provisional application No. 62/945,064, filed on Dec. 6, 2019.

(51) Int. Cl.
*C07K 1/14* (2006.01)
*C07K 16/28* (2006.01)

(52) U.S. Cl.
CPC ............ *C07K 16/2866* (2013.01); *C07K 1/14* (2013.01); *C07K 2317/24* (2013.01); *C07K 2317/622* (2013.01)

(58) Field of Classification Search
CPC .. C07K 16/2866; C07K 1/14; C07K 2317/24; C07K 2317/622; C07K 16/2809;
(Continued)

(56) References Cited

U.S. PATENT DOCUMENTS 4,452,773 A    6/1984  Molday
4,795,698 A    1/1989  Owen et al.
(Continued)

FOREIGN PATENT DOCUMENTS

CN    103483453 A    1/2014
CN    108239144      7/2018
(Continued)

OTHER PUBLICATIONS

US 8,252,592 B2, 08/2012, Sadelain (withdrawn)
(Continued)

*Primary Examiner* — Joanne Hama
*Assistant Examiner* — Hannah Sunshine
(74) *Attorney, Agent, or Firm* — Morrison & Foerster LLP

(57) ABSTRACT

Provided are anti-idiotype antibodies that specifically recognize anti-GPRC5D antibody moieties, in particular, anti-GPRC5D antibody moieties present in recombinant receptors, including chimeric antigen receptors (CARs). The disclosure further relates to uses of antiidiotype antibodies for specifically identifying and/or selecting cells expressing such recombinant receptors, such as anti-GPRC5D CAR T cells. The disclosure further relates to uses of anti-idiotype antibodies for specifically activating such cells.

32 Claims, 5 Drawing Sheets

Specification includes a Sequence Listing.

(58) Field of Classification Search
CPC .............. C07K 16/28; C07K 14/70521; C07K
2317/732; C07K 2317/92; A61P 35/00;
A61P 35/02; G01N 33/6854; A61K
2039/505
See application file for complete search history.

(56) References Cited

U.S. PATENT DOCUMENTS

| | | | |
|---|---|---|---|
| 4,816,567 | A | 3/1989 | Cabilly et al. |
| 5,200,084 | A | 4/1993 | Liberti et al. |
| 5,208,020 | A | 5/1993 | Chari et al. |
| 5,219,740 | A | 6/1993 | Miller et al. |
| 5,225,539 | A | 7/1993 | Winter |
| 5,283,173 | A | 2/1994 | Fields et al. |
| 5,416,064 | A | 5/1995 | Chari et al. |
| 5,468,614 | A | 11/1995 | Fields et al. |
| 5,585,089 | A | 12/1996 | Queen et al. |
| 5,624,821 | A | 4/1997 | Winter et al. |
| 5,635,483 | A | 6/1997 | Pettit et al. |
| 5,712,374 | A | 1/1998 | Kuntsmann et al. |
| 5,714,586 | A | 2/1998 | Kuntsmann et al. |
| 5,739,116 | A | 4/1998 | Hamann et al. |
| 5,767,285 | A | 6/1998 | Hamann et al. |
| 5,770,701 | A | 6/1998 | McGahren et al. |
| 5,770,710 | A | 6/1998 | McGahren et al. |
| 5,773,001 | A | 6/1998 | Hamann et al. |
| 5,780,588 | A | 7/1998 | Pettit et al. |
| 5,877,296 | A | 3/1999 | Hamann et al. |
| 6,040,177 | A | 3/2000 | Riddell et al. |
| 6,123,655 | A | 9/2000 | Fell |
| 6,207,453 | B1 | 3/2001 | Maass et al. |
| 6,407,213 | B1 | 6/2002 | Carter et al. |
| 6,410,319 | B1 | 6/2002 | Raubitschek et al. |
| 6,451,995 | B1 | 9/2002 | Cheung et al. |
| 6,602,684 | B1 | 8/2003 | Umana et al. |
| 6,630,579 | B2 | 10/2003 | Chari et al. |
| 6,733,433 | B1 | 5/2004 | Fell |
| 6,737,056 | B1 | 5/2004 | Presta |
| 6,982,321 | B2 | 1/2006 | Winter |
| 7,070,995 | B2 | 7/2006 | Jensen |
| 7,087,409 | B2 | 8/2006 | Barbas et al. |
| 7,217,797 | B2 | 5/2007 | Hinton et al. |
| 7,265,209 | B2 | 9/2007 | Jensen |
| 7,354,762 | B2 | 4/2008 | Jensen |
| 7,446,179 | B2 | 11/2008 | Jensen |
| 7,446,190 | B2 | 11/2008 | Sadelain et al. |
| 7,446,191 | B2 | 11/2008 | Jensen |
| 7,498,298 | B2 | 3/2009 | Doronina et al. |
| 7,521,541 | B2 | 4/2009 | Eignebrot et al. |
| 7,732,570 | B2 | 6/2010 | Hinton et al. |
| 7,855,275 | B2 | 12/2010 | Eignebrot et al. |
| 8,324,353 | B2 | 12/2012 | Jensen |
| 8,339,645 | B2 | 12/2012 | Nakawaki |
| 8,389,282 | B2 | 3/2013 | Sadelain et al. |
| 8,479,118 | B2 | 7/2013 | Lyndersay et al. |
| 8,802,374 | B2 | 8/2014 | Jensen |
| 8,822,647 | B2 | 9/2014 | Jensen |
| 8,911,993 | B2 | 12/2014 | June et al. |
| 9,163,080 | B2 * | 10/2015 | Morita .................... A61P 35/00 |
| 10,098,951 | B2 | 10/2018 | Lu et al. |
| 10,464,988 | B2 | 11/2019 | Lu et al. |
| 10,590,196 | B2 | 3/2020 | Brentjens et al. |
| 10,633,426 | B2 | 4/2020 | Brentjens et al. |
| 10,906,956 | B2 | 2/2021 | Brentjens et al. |
| 11,566,071 | B2 | 1/2023 | Brentjens et al. |
| 2002/0131960 | A1 | 9/2002 | Sadelain et al. |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2003/0207388 | A1 | 11/2003 | Baker et al. |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |

| | | | |
|---|---|---|---|
| 2004/0259150 | A1 | 12/2004 | Nakamura et al. |
| 2005/0019320 | A1 | 1/2005 | Sugaru et al. |
| 2005/0031613 | A1 | 2/2005 | Nakamura et al. |
| 2005/0123546 | A1 | 6/2005 | Umana et al. |
| 2005/0272916 | A1 | 12/2005 | Hanai et al. |
| 2006/0270045 | A1 | 11/2006 | Cregg et al. |
| 2007/0116690 | A1 | 5/2007 | Yang et al. |
| 2007/0134759 | A1 | 6/2007 | Nishiya |
| 2008/0057063 | A1 | 3/2008 | Rinkenberger et al. |
| 2008/0171951 | A1 | 7/2008 | Fell |
| 2008/0241884 | A1 | 10/2008 | Shitara et al. |
| 2009/0203078 | A1 | 8/2009 | Ogawa et al. |
| 2010/0143254 | A1 | 6/2010 | Dall'Acqua et al. |
| 2011/0003380 | A1 | 1/2011 | Miltenyi et al. |
| 2011/0166330 | A1 | 7/2011 | Koblika et al. |
| 2013/0130379 | A1 | 5/2013 | Ablynx |
| 2013/0149337 | A1 | 6/2013 | Cooper et al. |
| 2013/0287748 | A1 | 10/2013 | June et al. |
| 2014/0170678 | A1 | 6/2014 | Kasdan et al. |
| 2014/0271635 | A1 | 9/2014 | Brogdon et al. |
| 2014/0322183 | A1 | 10/2014 | Milone et al. |
| 2015/0330971 | A1 | 11/2015 | Kasdan et al. |
| 2018/0037651 | A1 | 2/2018 | Attar et al. |
| 2018/0118803 | A1 | 5/2018 | Brentjens et al. |
| 2020/0123249 | A1 | 4/2020 | Brentjens et al. |
| 2020/0270326 | A1 | 8/2020 | Brentjens et al. |
| 2020/0270327 | A1 | 8/2020 | Brentjens et al. |
| 2021/0393689 | A1 | 12/2021 | Sather et al. |

FOREIGN PATENT DOCUMENTS

| | | | |
|---|---|---|---|
| EP | | 0425235 | 5/1991 |
| EP | | 0452342 | 10/1991 |
| EP | | 1331266 | 7/2003 |
| EP | | 1 468 694 | 10/2004 |
| EP | | 1705251 | 9/2006 |
| EP | | 2537416 | 12/2012 |
| WO | WO 1992/008796 | | 5/1992 |
| WO | WO 1994/011026 | | 5/1994 |
| WO | WO 1994/028143 | | 12/1994 |
| WO | WO 1997/030087 | | 8/1997 |
| WO | WO 1998/058964 | | 12/1998 |
| WO | WO 1999/022764 | | 5/1999 |
| WO | WO 1999/058572 | | 11/1999 |
| WO | WO 2000/014257 | | 3/2000 |
| WO | WO 2000/038762 | | 7/2000 |
| WO | WO 2003/011878 | | 2/2003 |
| WO | WO 2004/056312 | | 7/2004 |
| WO | WO 2004/072117 | | 8/2004 |
| WO | WO 2005/019258 | | 3/2005 |
| WO | WO 2009/039192 | | 3/2009 |
| WO | WO 2009/055711 | | 4/2009 |
| WO | WO 2009/072003 | | 6/2009 |
| WO | WO 2010/033140 | | 3/2010 |
| WO | WO 2011/056983 | | 5/2011 |
| WO | WO 2011/083088 | | 7/2011 |
| WO | WO 2011/128893 | | 10/2011 |
| WO | WO 2012/009790 | | 1/2012 |
| WO | WO 2012/129514 | | 9/2012 |
| WO | WO 2013/071154 | | 5/2013 |
| WO | WO 2013/123061 | | 8/2013 |
| WO | WO 2013/126726 | | 8/2013 |
| WO | WO 2013/166321 | | 11/2013 |
| WO | WO 2013/185552 | | 12/2013 |
| WO | WO 2014/031687 | | 2/2014 |
| WO | WO 2014/055668 | | 4/2014 |
| WO | WO 2014/097286 | | 6/2014 |
| WO | WO 2014/097287 | | 6/2014 |
| WO | WO 2014/114800 | | 7/2014 |
| WO | WO 2014/127261 | | 8/2014 |
| WO | WO 2014/191128 | | 12/2014 |
| WO | WO 2015/158868 | | 10/2015 |
| WO | WO 2016/073602 | | 5/2016 |
| WO | WO 2016/090312 | | 6/2016 |
| WO | WO 2016/090320 | | 6/2016 |
| WO | WO 2016/090329 | | 6/2016 |
| WO | WO 2017/172981 | | 10/2017 |
| WO | WO 2017/222593 | | 12/2017 |

(56)                    References Cited

FOREIGN PATENT DOCUMENTS

WO       WO 2019/032927       2/2019
WO       WO 2019/090003       5/2019
WO       WO 2020/092854       5/2020

OTHER PUBLICATIONS

Koenig P, Lee CV, Walters BT, et al. Mutational landscape of antibody variable domains reveals a switch modulating the interdomain conformational dynamics and antigen binding. Proc Natl Acad Sci U S A. 2017;114(4):E486-E495. (Year: 2017).*

Rabia LA, Desai AA, Jhajj HS, Tessier PM. Understanding and overcoming trade-offs between antibody affinity, specificity, stability and solubility. Biochem Eng J. Sep. 15, 2018;137:365-374. (Year: 2018).*

U.S. Appl. No. 18/145,254, filed Dec. 22, 2022, by Brentjens et al.

Al-Lazikani et al., "Standard Conformations for the Canonical Structures of Immunoglobulins," J. Mol. Biol. (1997) 273: 927-948.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93 (11 pages).

Atamaniuk et al., "Overexpression of G protein-coupled receptor SD in the bone marrow is associated with poor prognosis in patients with multiple myeloma," European Journal of Clinical Investigation, 42(9):953-960 (2012).

Barderas et al., "Affinity maturation of antibodies assisted by in silico modeling," Proc. Natl. Acad. Sci. U.S.A. (2008) 105(26):9029-34.

Barret, D.M. et al. (2014, e-pub. Nov. 20, 2013). "Chimeric Antigen Receptor Therapy for Cancer," Annu Rev Med. (2014);65:333-347.

Beckman et al., "Antibody constructs in cancer therapy: protein engineering strategies to improve exposure in solid tumors," Cancer (2007) 109:170-79.

Boris-Lawrie, K.A. et al. "Recent advances in retrovirus vector technology", Curr Opin Genet Dev. (1993) 3(1):102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177):177ra38 (19 pages).

Brown et al., "Tolerance of single, but not multiple, amino acid replacements in antibody VH CDR2: a means of minimizing B cells wastage from somatic hypermutation?" J. Immunol. (1996) 156(9):3285-3291.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-46.

Carrillo et al., "The Multiple Sequence Alignment Problem in Biology," SIAM J Applied Math (1988) 48: 1073 (10 pages).

Carter et al., "Humanization of an Anti-p185HER2 Antibody for Human Cancer Therapy," Proc. Natl. Acad. Sci. USA. (1992) 89:4285-4289.

Cavalieri et al., "Human T lymphocytes transduced by lentiviral vectors in the absence of TCR activation maintain an intact immune competence," Blood (2003) 102(2): 497-505.

Chari et al., "Immunoconjugates containing novel maytansinoids: promising anticancer drugs," Cancer Res. (1992) 52:127-131.

Cheadle et al., "Chimeric antigen receptors for T-cell based therapy," Methods Mol Biol. (2012);907:645-66.

Chicaybam et al., "An efficient low cost method for gene transfer to T lymphocytes," PLoS ONE (2013) 8(3): e60298 (11 pages).

Cho et al., "Human mammalian cell sorting using a highly integrated micro-fabricated fluorescence-activated cell sorter (microFACS)," Lab Chip (2010) 10: 1567-1573.

Chothia et al.,"Canonical Structures for the Hypervariable Regions of Immunoglobulins," J. Mol. Biol. (1987) 196:901-917.

Clackson et al. "Making antibody fragments using phage display libraries," Nature (1991) 352:624-628.

Cohen et al., "GPRC5D is a promising marker for monitoring the tumor load and to target multiple myeloma cells," Hematology 18(6):348-351 (2013).

Coico (Koyko) et al., "Immunology," translation from English, edited by N.B. Serebryanaya, Mosow, "Akademiya," 2008, p. 37 (in Russian).

Cooper et al., "T-cell clones can be rendered specific for CD19: toward the selective augmentation of the graft-versus-B-lineage leukemia effect," Blood (2003) 101:1637-1644.

Davila et al., "CD19 CAR-targeted T cells induce long-term remission and B Cell Aplasia in an immunocompetent mouse model of B cell acute lymphoblastic leukemia," PLoS ONE (2013) 8(4): e61338 (14 pages).

De Felipe, "Skipping the co-expression problem: the new 2A "Chysel" technology," Genet Vaccines Ther (2004) Sep. 13;2(1):13 (6 pages).

De Felipe, "Targeting of proteins derived from self-processing polyproteins containing multiple signal sequences," Traffic (2004) 5(8):616-626.

Dennis et al., "Cancer: Off by a Whisker," Nature (20006) 442:739-41.

Dubowchik et al., "Doxorubicin immunoconjugates containing bivalent, lysosomally-cleavable dipeptide linkages," Bioorg. & Med. Chem. Letters (2002) 12:1529-1532.

Dykman et al."Gold nanoparticles in biology and medicine. Recent Advances and Prospects," (2011) Acta Naturae. 3(2):34-55.

Endo et al., "High-throughput, genome-scale protein production method based on the wheat germ cell-free expression system," Biotechnol. Adv. (2003) 21: 695-713.

Fedorov et al., "PD-1- and CTLA-4-based inhibitory chimeric antigen receptors (iCARs) divert off-target immunotherapy responses," Sci. Transl. Medicine (2013) 5(215) (25 pages).

Flatman et al., "Process analytics for purification of monoclonal antibodies," J. Chromatogr. (2007) B 848:79-87.

Fujimori et al., "A modeling analysis of monoclonal antibody percolation through tumors: a binding-site barrier," J Nucl. Med. (1990) 31:1191-98.

Gerngross et al., "Advances in the Production of Human Therapeutic Proteins in Yeasts and Filamentous Fungi," Nature Biotechnology. (2004) 22(11):1409-1414.

Gershoni et al., "Epitope mapping—The first step in developing epitope-based vaccines," Biod, Adis International Ltd, 21 (3 ): 145-156 (2007).

Godin et al., "Microfluidics and photonics for Bio-System-on-a-Chip: a review of advancements in technology towards a microfluidic flow cytometry chip," J Biophoton. (2008) 1(5):355-376.

Harris, W.J. (1995). "Production of Humanized Monoclonal and Antibodies for in vivo Imaging and Therapy," Biochem. Soc. Transactions 23:1035-1038.

Hinman et al., "Preparation and characterization of monoclonal antibody conjugates of the calicheamicins: a novel and potent family of antitumor antibiotics," Cancer Res. (1993) 53:3336-3342.

Hirano et al., "Novel reciprocal regulation of cAMP signaling and apoptosis by orphan G-protein-coupled receptor GPRC5A gene expression," Biochemical and Biophysical Research Communications (2006) 351:185-91.

Honegger et al., "Yet another numbering scheme for immunoglobulin variable domains: an automatic modeling and analysis tool," J Mol Biol, (2001) 8;309(3):657-670.

Hoogenboom et al., "Overview of antibody phage-display technology and its applications," Methods in Molecular Biology (2002) 178:1-37.

Huang et al., "DNA transposons for modification of human primary T lymphocytes," Methods Mol Biol (2009) 506: 115-126.

(56) References Cited

OTHER PUBLICATIONS

Hudecek et al., "Receptor affinity and extracellular domain modifications affect tumor recognition by ROR1-specific chimeric antigen receptor T cells," Clin. Cancer Res. (2013) 19:3153-3164.
Hudecek et al., "The nonsignaling extracellular spacer domain of chimeric antigen receptors is decisive for in vivo antitumor activity," Cancer Immunol Res (2015) 3(2):125-135.
Hurle et al., "Protein Engineering Techniques for Antibody Humanization," Curr. Op. Biotech. (1994) 5(4):428-433.
Jeffrey et al., "Dipeptide-based highly potent doxorubicin antibody conjugates," Bioorganic & Med. Chem. Letters (2006) 16:358-362.
Jiang et al., "T-cell exhaustion in the tumor microenvironment," Cell Death & Disease (2015) 6:e1792 (9 pages).
Johnston, et al., "Biolistic transformation: microbes to mice," Nature (1990) 346: 776-777.
Jones et al., "Replacing the Complementarity-Determining Regions in a Human Antibody With Those From a Mouse," Nature. (1986) 321:522-525.
Kanda, Y. et al., "Comparison of cell lines for stable production of fucose-negative antibodies with enhanced ADCC," Biotechnol. Bioeng. (2006) 94(4):680-688.
Kindt et al. (2007). "Antigens And Antibodies," Chapter 4 In Kuby Immunology 6th Ed., W.H. Freeman And Co., p. 91.
King et al., "Monoclonal antibody conjugates of doxorubicin prepared with branched peptide linkers: inhibition of aggregation by methoxytriethyleneglycol chains," J. Med. Chem. (2002) 45:4336-4343.
Klebanoff et al., "Sorting through subsets: which T-cell populations mediate highly effective adoptive immunotherapy?," J Immunother. (2012) 35(9): 651-660.
Kochenderfer et al., "Adoptive transfer of syngeneic T cells transduced with a chimeric antigen receptor that recognizes murine CD19 can eradicate lymphoma and normal B cells," Blood (2010) 116(19):3875-3886.
Kochenderfer et al., "Treating B-cell cancer with T cells expressing anti-CD19 chimeric antigen receptors," Nature Reviews Clinical Oncology (2013) 10, 267-276.
Koste et al., "T-cell receptor transfer into human T cells with ecotropic retroviral vectors," Gene Therapy (2014) 21: 533-538.
Kratz et al., "Prodrugs of anthracyclines in cancer chemotherapy," Current Med. Chem. (2006) 13:477-523.
Lefranc et al., "IMGT unique numbering for immunoglobulin and T cell receptor variable domains and Ig superfamily V-like domains," Dev Comp Immunol (2003) 27(1):55-77.
Li et al., "Optimization of humanized IgGs in glycoengineered Pichia pastoris," Nat Biotechnol. (2006) 24(2):210-215.
Lloyd et al., "Modelling the human immune response: performance of a 10/∧11 human antibody repertoire against a broad panel of therapeutically relevant antigens," Protein Engineering, Design & Selection (2009) 22(3):159-68.
Lode et al., "Targeted therapy with a novel enediyne antibiotic calicheamicin theta(I)1 effectively suppresses growth and dissemination of liver metastases in a syngeneic model of murine neuroblastoma," Cancer Res. (1998) 58:2925-2928.
Lupton S. D. et al., "Dominant positive and negative selection using a hygromycin phosphotransferase-thymidine kinase fusion gene," Mol. and Cell Biol. (1991) 11(6): 3374-3378.
Maccallum et al., "Antibody-antigen interactions: Contact analysis and binding site topography," J. Mol. Biol. (1996) 262, 732-745.
Manuri et al., "piggyBac transposon/transposase system to generate CD19-specific T cells for the treatment of B-lineage malignancies," Hum Gene Ther (2010) 21(4): 427-437.
Mariuzza et al., "The structural basis of antigen-antibody recognition," Annual Review of Biophysis and Biophysical Chemistry (1987) 16:139-59.
Maynard et al., "Protection against anthrax toxin by recombinant antibody fragments correlates with antigen affinity," Nature Biotech. (2002) 20(6):597-601.

Methods in Molecular Medicine, vol. 58: Metastasis Research Protocols, vol. 2: Cell Behavior In Vitro and In Vivo, p. 17-25 Edited by: S. A. Brooks and U. Schumacher © Humana Press Inc., Totowa, NJ (2001).
Miller et al., "Improved retroviral vectors for gene transfer and expression," BioTechniques (1989) 7:980-990.
Miller et al., "Retrovirus packaging cells," Human Gene Therapy (1990) 1:5-14.
Nagy et al., "Stability of cytotoxic luteinizing hormone-releasing hormone conjugate (AN-152) containing doxorubicin 14-O-hemiglutarate in mouse and human serum in vitro: implications for the design of preclinical studies," Proc. Natl. Acad. Sci. USA (2000) 97:829-834.
Okazaki et al., "Fucose depletion from human IgG1 oligosaccharide enhances binding enthalpy and association rate between IgG1 and FcgammaRIIIa," J. Mol. Biol. (2004) 336:1239-1249.
Ozhegov et al. "Dictionary of a Russian Language: 80,000 words and phraseological expressions," 4th ed. Supplemented, Mosow, "OOO 'A TEMP'" 2006, p. 375.
Park et al., "Treating cancer with genetically engineered T cells," Trends Biotechnol. (2011) 29(11): 550-557.
Parkman R., "Clonal analysis of murine graft-vs-host disease. I. Phenotypic and functional analysis of T lymphocyte clones," J. Immunol. (1986) 136(10):3543-3548.
Portolano et al., "Lack of promiscuity in autoantigen-specific H and L chain combinations as revealed by human H and L chain "roulette"," J. Immunol. (1993) 150:880-887.
Presta et al., "Humanization of an Antibody Directed Against IgE," J. Immunol. (1993) 151(2):2623-2632.
Presta, "Antibody engineering," Curr Opi Struct Biol (1992) 2(4):593-596.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3:319-338.
Riechmann et al., "Reshaping Human Antibodies for Therapy," Nature. (1988) 33(6162):323-327.
Ripka et al., "Two Chinese hamster ovary glycosylation mutants affected in the conversion of GDP-mannose to GDP-fucose," Arch. Biochem. Biophys. (1986) 249:533-545.
Rudnick et al., "Affinity and avidity in antibody-based tumor targeting," Can. Biotherap. & Radiopharm. (2009) 24(2):155-62.
Sadelain et al., "The basic principles of chimeric antigen receptor design," Cancer Discov. (2013) 3(4): 388-398.
Scarpa et al., "Characterization of recombinant helper retroviruses from Moloney-based vectors in ecotropic and amphotropic packaging cell lines," Virology (1991) 180:849-852.
Scatchard, G. (1949). "The Attractions of Proteins for Small Molecules and Ions," Annals of the New York Academy of Sciences, Department of Chemistry, Massachusetts Institute of Technology, MA, 51(4)660-672.
Sharma et al., "Efficient sleeping beauty DNA transposition from DNA minicircles," Molec Ther Nucl Acids (2013) 2, e74 (10 pages).
Sims et al., "A Humanized CD18 Antibody Can Block Function without Cell Destruction," The Journal of Immunology. (1993) 151(4):2296-2308.
Sitaraman et al., "High-throughput protein expression using cell-free system," Methods Mol. Biol. (2009) 498: 229-44.
Smith et al, "GPRC5D is a target for the immunotherapy of multiple myeloma with rationally designed Car T cells," Sci. Trans. Med. (2019) 11(485): eaau7746 (26 pages).
Spirin et al., "High-throughput cell-free systems for synthesis of functionally active proteins," Trends Biotechnol. (2004) 22: 538-45.
Talmadge et al., "Murine models to evaluate novel and conventional therapeutic strategies for cancer," Am. J. Pathol. (2007) 170(3):793-804.
Tang and Bluestone, "The Foxp3+ regulatory T cell: a jack of all trades, master of regulation," Nat Immunol (2008) 9(3):239-44.
Terakura et al., "Generation of CD19-chimeric antigen receptor modified CD8+ T cells derived from virus-specific central memory T cells," Blood (2012) 1:72-82.

(56)                    References Cited

OTHER PUBLICATIONS

Timmerman et al., "Functional reconstruction and synthetic mim-icry of a conformational epitope using CLIPS technology," J Mol Recognit (2007) 20(5):283-299.
Torgov et al., "Generation of an intensely potent anthracycline by a monoclonal antibody-beta-galactosidase conjugate," Bioconj. Chem. (2005) 16:717-721.
Turtle et al., "Engineered T cells for anti-cancer therapy," Curr. Opin. Immunol. (2012) 24(5): 633-39.
Van Tendeloo et al., "High-level transgene expression in primary human T lymphocytes and adult bone marrow CD34+ cells via electroporation-mediated gene delivery," Gene Therapy (2000) 7(16): 1431-1437.
Vaswani et al., "Humanized Antibodies as Potential Therapeutic Drugs," Ann. Allergy, Asthma & Immunol. (1998) 81:105-119.
Verhoeyen et al., "Lentiviral vector gene transfer into human T cells," Methods Mol Biol. (2009) 506: 97-114.
Verhoeyen et al., "Reshaping human antibodies: grafting an antilysozyme activity," Science (1988) 239(4847):1534-1536.
Vitetta et al., "Redesigning nature's poisons to create anti-tumor reagents," Science (1987) 238:1098 (9 pages).
Voskoglou-Nomikos et al., "Clinical predictive value of the in vitro cell line, human xenograft, and mouse allograft preclinical cancer models," Clin. Canc. Res. (2003) 9:4227-39.
Wang et al., "Phenotypic and functional attributes of lentivirus-modified CD19-specific human CD8+ central memory T cells manufactured at clinical scale," J Immunother. (2012) 35(9):689-701.
Wilson, "Tech.Sight. Analyzing biomolecular interactions," Science (2002) 295(5562): 2103-2105.
Winkler et al., "Changing the Antigen Binding Specificity by Single Point Mutations of an Anti-p24 (HIV-1) Antibody," J Immunol. 165:4505-4514, 2000. (11 Pages).
Wolff et al., "Monoclonal Antibody Homodimers: Enhanced Anti-tumor Activity in Nude Mice," Can Res. (1993) 53:2560-2565.
Wu et al., "Adoptive T-cell therapy using autologous tumor-infiltrating lymphocytes for metastatic melanoma: current status and future outlook," Cancer (2012) 18(2): 160-75.
Yamane-Ohnuki et al., "Establishment of FUT8 knockout Chinese hamster ovary cells: an ideal host cell line for producing completely defucosylated antibodies with enhanced antibody-dependent cellu-lar cytotoxicity," Biotech. Bioeng. (2004) 87: 614 (9 pages).
Yeger (Jaeger), L., "Clinical Immunology and Allergology" vol. 1, 219-222 (1990).
Zhong et al., "Chimeric antigen receptors combining 4-1BB and CD28 signaling domains augment PI3kinase/AKT/Bcl-XL activa-tion and CD8+ T cell-mediated tumor eradication," Mol Ther (2010) 18(2):413-20.

Almagro et al., "Humanization of antibodies," Front Biosci (Jan. 2008) 13:1619-33.
Altshuler et al., "Generation of recombinant antibodies and means for increasing their affinity," Biochemistry (Mosc) (Dec. 2010) 75(13):1584-1605.
Berahovich et al., "CAR-T Cells Based on Novel BCMA Mono-clonal Antibody Block Multiple Myeloma Cell Growth," Cancers (Basel) (2018) 10(9):323, 16 pages.
Chen et al., "Enhancement and destruction of antibody function by somatic mutation: unequal occurrence is controlled by V gene combinatorial associations," EMBO J (Jun. 1995) 14(12):2784-94.
Cho et al., "BCMA CAR T-cell therapy arrives for multiple myeloma: a reality," Ann Transl Med (2018) 6(Suppl 2):S93, 5 pages.
Curran et al., "Chimeric antigen receptors for T cell immunotherapy: current understanding and future directions," J Gene Med (2012) 14(6):405-415.
Ebert et al., "Logic-gated approaches to extend the utility of chimeric antigen receptor T-cell technology," Biochem Soc Trans (Apr. 2018) 46(2):391-401.
Edwards et al., "The remarkable flexibility of the human antibody repertoire; isolation of over one thousand different antibodies to a single protein, BLyS," J. Mol. Biol. (2003) 334(1):103-118.
Hasegawa et al., "Single amino acid substitution in LC-CDR1 induces Russell body phenotype that attenuates cellular protein synthesis through eIF2α phosphorylation and thereby downregulates IgG secretion despite operational secretory pathway traffic," MAbs (Jul. 2017, e-pub. Apr. 5, 2017) 9(5):854-873.
Huang et al., "Recombinant immunotherapeutics: current state and perspectives regarding the feasibility of the market," Appl. Microbiol. Biotechnol. (2010) 87:401-410.
Lippow et al., "Computational design of antibody-affinity improve-ment beyond in vivo maturation," Nat Biotechnol (Oct. 2007, e-pub. Sep. 23, 2007) 25(10):1171-1176.
Marchalonis et al., "The antibody repertoire in evolution: chance, selection, and continuity," Dev Comp Immunol (2006) 30(1-2):223-247.
Pearson et al., "An introduction to sequence similarity ("homol-ogy") searching," Curr Protoc Bioinformatics (2013) Chapter 3:3. 1.1-3.1.8.
Sulea et al., "Application of Assisted Design of Antibody and Protein Therapeutics (ADAPT) improves efficacy of a Clostridium difficile toxin A single-domain antibody," Sci Rep (Feb. 2, 2018) 8(1):2260, 11 pages.
Thurber et al., "Antibody tumor penetration: transport opposed by systemic and antigen-mediated clearance," Adv Drug Deliv Rev (2008) 60(12):1421-1434.
Tsujisaki et al., "Analysis of anti idiotypic monoclonal antibodies and their application in tumor immunology," Drug Delivery System (1993) 8(6):425-432. English abstract provided.

* cited by examiner

```
                          SEQUENCE LISTING

<160> NUMBER OF SEQ ID NOS: 45

<210> SEQ ID NO 1
<211> LENGTH: 5
<212> TYPE: PRT
<213> ORGANISM: Artificial Sequence
<220> FEATURE:
<223> OTHER INFORMATION: CDR-H1 (Kabat)

<400> SEQUENCE: 1

Ser His Ser Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: CDR-H2 (Kabat)

<400> SEQUENCE: 2

Ser Ile Ser Ser Asp Ser Thr Tyr Thr Tyr Tyr Ala Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: CDR-H3 (Kabat)

<400> SEQUENCE: 3

Ser Gly Gly Gln Trp Lys Tyr Tyr Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDR-L1 (Kabat)

<400> SEQUENCE: 4

Gln Gly Asp Ser Leu Arg Ser Tyr Tyr Ala Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR-L2 (Kabat)

<400> SEQUENCE: 5

Gly Lys Asn Asn Arg Pro Ser
1               5

<210> SEQ ID NO 6
<211> LENGTH: 12
<212> TYPE: PRT
<213> ORGANISM: Artificial Sequence
```

-continued

<220> FEATURE:
<223> OTHER INFORMATION: CDR-L3 (Kabat)

<400> SEQUENCE: 6

Asn Ser Arg Asp Ser Ser Gly Asn Pro Pro Val Val
1               5                   10

<210> SEQ ID NO 7
<211> LENGTH: 119
<212> TYPE: PRT
<213> ORGANISM: Artificial Sequence
<220> FEATURE:
<223> OTHER INFORMATION: anti-GPRC5D VH chain

<400> SEQUENCE: 7

Gln Val Gln Leu Val Glu Ser Gly Gly Gly Leu Val His Pro Gly Gly
1               5                   10                  15

Ser Leu Arg Leu Ser Cys Ala Ala Ser Gly Phe Thr Phe Arg Ser His
            20                  25                  30

Ser Met Asn Trp Val Arg Gln Ala Pro Gly Lys Gly Leu Glu Trp Val
        35                  40                  45

Ser Ser Ile Ser Ser Asp Ser Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Gly Gln Trp Lys Tyr Tyr Asp Tyr Trp Gly Gln Gly
            100                 105                 110

Thr Leu Val Thr Val Ser Ser
        115

<210> SEQ ID NO 8
<211> LENGTH: 110
<212> TYPE: PRT
<213> ORGANISM: Artificial Sequence
<220> FEATURE:
<223> OTHER INFORMATION: anti-GPRC5D VL chain

<400> SEQUENCE: 8

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Pro
                85                  90                  95

Pro Val Val Phe Gly Gly Gly Thr Lys Leu Thr Val Leu Gly
            100                 105                 110

<210> SEQ ID NO 9
<211> LENGTH: 250
<212> TYPE: PRT
<213> ORGANISM: Artificial Sequence
<220> FEATURE:

<223> OTHER INFORMATION: anti-GPRC5D scFv (VL-VH)

<400> SEQUENCE: 9

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Pro
                85                  90                  95

Pro Val Val Phe Gly Gly Gly Thr Lys Leu Thr Val Leu Gly Ser Arg
                100                 105                 110

Gly Gly Gly Gly Ser Gly Gly Gly Gly Ser Gly Gly Gly Gly Ser Leu
        115                 120                 125

Glu Met Ala Gln Val Gln Leu Val Glu Ser Gly Gly Gly Leu Val His
    130                 135                 140

Pro Gly Gly Ser Leu Arg Leu Ser Cys Ala Ala Ser Gly Phe Thr Phe
145                 150                 155                 160

Arg Ser His Ser Met Asn Trp Val Arg Gln Ala Pro Gly Lys Gly Leu
                165                 170                 175

Glu Trp Val Ser Ser Ile Ser Ser Asp Ser Thr Tyr Thr Tyr Tyr Ala
                180                 185                 190

Asp Ser Val Lys Gly Arg Phe Thr Ile Ser Arg Asp Asn Ala Lys Asn
                195                 200                 205

Ser Leu Tyr Leu Gln Met Asn Ser Leu Arg Ala Glu Asp Thr Ala Val
    210                 215                 220

Tyr Tyr Cys Ala Arg Ser Gly Gly Gln Trp Lys Tyr Tyr Asp Tyr Trp
225                 230                 235                 240

Gly Gln Gly Thr Leu Val Thr Val Ser Ser
                245                 250
```

<210> SEQ ID NO 10
<211> LENGTH: 21
<212> TYPE: PRT
<213> ORGANISM: Artificial Sequence
<220> FEATURE:
<223> OTHER INFORMATION: Linker

<400> SEQUENCE: 10

```
Ser Arg Gly Gly Gly Gly Ser Gly Gly Gly Gly Ser Gly Gly Gly Gly
1               5                   10                  15

Ser Leu Glu Met Ala
            20
```

<210> SEQ ID NO 11
<211> LENGTH: 12
<212> TYPE: PRT
<213> ORGANISM: Artificial Sequence
<220> FEATURE:
<223> OTHER INFORMATION: Spacer

<400> SEQUENCE: 11

```
Glu Ser Lys Tyr Gly Pro Pro Cys Pro Pro Cys Pro
```

```
1              5             10
```

<210> SEQ ID NO 12
<211> LENGTH: 28
<212> TYPE: PRT
<213> ORGANISM: Artificial Sequence
<220> FEATURE:
<223> OTHER INFORMATION: CD28 transmembrane domain

<400> SEQUENCE: 12

```
Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25
```

<210> SEQ ID NO 13
<211> LENGTH: 42
<212> TYPE: PRT
<213> ORGANISM: Artificial Sequence
<220> FEATURE:
<223> OTHER INFORMATION: 4-1BB-derived intracellular co-signaling
      sequence

<400> SEQUENCE: 13

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 14
<211> LENGTH: 112
<212> TYPE: PRT
<213> ORGANISM: Artificial Sequence
<220> FEATURE:
<223> OTHER INFORMATION: CD3-zeta derived intracellular

<400> SEQUENCE: 14

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 15
<211> LENGTH: 5
<212> TYPE: PRT
<213> ORGANISM: Artificial Sequence
<220> FEATURE:
<223> OTHER INFORMATION: CDR-H1 (Kabat)

<400> SEQUENCE: 15

-continued

```
Asp Tyr Tyr Met Tyr
1               5

<210> SEQ ID NO 16
<211> LENGTH: 17
<212> TYPE: PRT
<213> ORGANISM: Artificial Sequence
<220> FEATURE:
<223> OTHER INFORMATION: CDR-H2 (Kabat)

<400> SEQUENCE: 16

Thr Ile Ser Asp Gly Gly Ser Tyr Thr Tyr Tyr Pro Asp Ser Val Lys
1               5                   10                  15

Gly

<210> SEQ ID NO 17
<211> LENGTH: 15
<212> TYPE: PRT
<213> ORGANISM: Artificial Sequence
<220> FEATURE:
<223> OTHER INFORMATION: CDR-H3 (Kabat, Chothia, AbM)

<400> SEQUENCE: 17

Asp Trp Asn Pro Tyr Tyr Gly Ser Gly Gly Trp Phe Gly Tyr
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: CDR-H1 (Chothia)

<400> SEQUENCE: 18

Gly Phe Thr Phe Ser Asp Tyr
1               5

<210> SEQ ID NO 19
<211> LENGTH: 6
<212> TYPE: PRT
<213> ORGANISM: Artificial Sequence
<220> FEATURE:
<223> OTHER INFORMATION: CDR-H2 (Chothia)

<400> SEQUENCE: 19

Ser Asp Gly Gly Ser Tyr
1               5

<210> SEQ ID NO 20
<211> LENGTH: 10
<212> TYPE: PRT
<213> ORGANISM: Artificial Sequence
<220> FEATURE:
<223> OTHER INFORMATION: CDR-H1 (AbM)

<400> SEQUENCE: 20

Gly Phe Thr Phe Ser Asp Tyr Tyr Met Tyr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: CDR-H2 (AbM)

<400> SEQUENCE: 21
```

-continued

```
Thr Ile Ser Asp Gly Gly Ser Tyr Thr Tyr
1               5                   10

<210> SEQ ID NO 22
<211> LENGTH: 15
<212> TYPE: PRT
<213> ORGANISM: Artificial Sequence
<220> FEATURE:
<223> OTHER INFORMATION: CDR-L1 (Kabat, Chothia, AbM)

<400> SEQUENCE: 22

Lys Ala Ser Gln Ser Val Asp Tyr Asp Gly Asp Ser Tyr Met Asn
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: CDR-L2 (Kabat, Chothia, AbM)

<400> SEQUENCE: 23

Ala Ala Ser Asn Leu Glu Ser
1               5

<210> SEQ ID NO 24
<211> LENGTH: 9
<212> TYPE: PRT
<213> ORGANISM: Artificial Sequence
<220> FEATURE:
<223> OTHER INFORMATION: CDR-L3 (Kabat, Chothia, AbM)

<400> SEQUENCE: 24

Gln Gln Ser Asn Glu Asp Pro Phe Thr
1               5

<210> SEQ ID NO 25
<211> LENGTH: 124
<212> TYPE: PRT
<213> ORGANISM: Artificial Sequence
<220> FEATURE:
<223> OTHER INFORMATION: Anti-ID VH chain

<400> SEQUENCE: 25

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Asp Trp Val
        35                  40                  45

Ala Thr Ile Ser Asp Gly Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Asp Trp Asn Pro Tyr Tyr Gly Ser Gly Gly Gly Trp Phe Gly
            100                 105                 110

Tyr Trp Gly Gln Gly Thr Leu Val Thr Ala Ser Ala
        115                 120

<210> SEQ ID NO 26
```

<211> LENGTH: 111
<212> TYPE: PRT
<213> ORGANISM: Artificial Sequence
<220> FEATURE:
<223> OTHER INFORMATION: Anti-ID VL chain

<400> SEQUENCE: 26

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu Ile Lys
            100                 105                 110

<210> SEQ ID NO 27
<211> LENGTH: 454
<212> TYPE: PRT
<213> ORGANISM: Artificial Sequence
<220> FEATURE:
<223> OTHER INFORMATION: Anti-ID Heavy chain

<400> SEQUENCE: 27

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Asp Trp Val
        35                  40                  45

Ala Thr Ile Ser Asp Gly Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Asp Trp Asn Pro Tyr Tyr Gly Ser Gly Gly Gly Trp Phe Gly
            100                 105                 110

Tyr Trp Gly Gln Gly Thr Leu Val Thr Ala Ser Ala Ala Lys Thr Thr
        115                 120                 125

Ala Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg

```
       210              215              220
Gly Pro Thr Ile Lys Pro Cys Pro Pro Cys Lys Cys Pro Ala Pro Asn
225              230              235              240

Leu Leu Gly Gly Pro Ser Val Phe Ile Phe Pro Pro Lys Ile Lys Asp
              245              250              255

Val Leu Met Ile Ser Leu Ser Pro Ile Val Thr Cys Val Val Val Asp
              260              265              270

Val Ser Glu Asp Asp Pro Asp Val Gln Ile Ser Trp Phe Val Asn Asn
              275              280              285

Val Glu Val His Thr Ala Gln Thr Gln Thr His Arg Glu Asp Tyr Asn
      290              295              300

Ser Thr Leu Arg Val Val Ser Ala Leu Pro Ile Gln His Gln Asp Trp
305              310              315              320

Met Ser Gly Lys Glu Phe Lys Cys Lys Val Asn Asn Lys Asp Leu Pro
              325              330              335

Ala Pro Ile Glu Arg Thr Ile Ser Lys Pro Lys Gly Ser Val Arg Ala
              340              345              350

Pro Gln Val Tyr Val Leu Pro Pro Pro Glu Glu Met Thr Lys Lys
              355              360              365

Gln Val Thr Leu Thr Cys Met Val Thr Asp Phe Met Pro Glu Asp Ile
      370              375              380

Tyr Val Glu Trp Thr Asn Asn Gly Lys Thr Glu Leu Asn Tyr Lys Asn
385              390              395              400

Thr Glu Pro Val Leu Asp Ser Asp Gly Ser Tyr Phe Met Tyr Ser Lys
              405              410              415

Leu Arg Val Glu Lys Lys Asn Trp Val Glu Arg Asn Ser Tyr Ser Cys
              420              425              430

Ser Val Val His Glu Gly Leu His Asn His His Thr Thr Lys Ser Phe
              435              440              445

Ser Arg Thr Pro Gly Lys
    450
```

```
<210> SEQ ID NO 28
<211> LENGTH: 218
<212> TYPE: PRT
<213> ORGANISM: Artificial Sequence
<220> FEATURE:
<223> OTHER INFORMATION: Anti-ID Light chain

<400> SEQUENCE: 28

Asp Ile Val Leu Thr Gln Ser Pro Ala Ser Leu Ala Val Ser Leu Gly
1               5               10              15

Gln Arg Ala Thr Ile Ser Cys Lys Ala Ser Gln Ser Val Asp Tyr Asp
              20              25              30

Gly Asp Ser Tyr Met Asn Trp Tyr Gln Gln Lys Pro Gly Gln Pro Pro
              35              40              45

Lys Leu Leu Ile Tyr Ala Ala Ser Asn Leu Glu Ser Gly Ile Pro Ala
    50              55              60

Arg Phe Ser Gly Ser Gly Ser Gly Thr Asp Phe Thr Leu Asn Ile His
65              70              75              80

Pro Val Glu Glu Glu Asp Ala Ala Thr Tyr Tyr Cys Gln Gln Ser Asn
              85              90              95

Glu Asp Pro Phe Thr Phe Gly Ser Gly Thr Lys Leu Glu Ile Lys Arg
              100             105             110

Ala Asp Ala Ala Pro Thr Val Ser Ile Phe Pro Pro Ser Ser Glu Gln
```

```
              115                    120                     125
Leu Thr Ser Gly Gly Ala Ser Val Val Cys Phe Leu Asn Asn Phe Tyr
    130                    135                     140

Pro Lys Asp Ile Asn Val Lys Trp Lys Ile Asp Gly Ser Glu Arg Gln
145                    150                     155                     160

Asn Gly Val Leu Asn Ser Trp Thr Asp Gln Asp Ser Lys Asp Ser Thr
                165                    170                     175

Tyr Ser Met Ser Ser Thr Leu Thr Leu Thr Lys Asp Glu Tyr Glu Arg
                180                    185                     190

His Asn Ser Tyr Thr Cys Glu Ala Thr His Lys Thr Ser Thr Ser Pro
                195                    200                     205

Ile Val Lys Ser Phe Asn Arg Asn Glu Cys
    210                    215
```

<210> SEQ ID NO 29
<211> LENGTH: 372
<212> TYPE: DNA
<213> ORGANISM: Artificial Sequence
<220> FEATURE:
<223> OTHER INFORMATION: Anti-ID VH chain

<400> SEQUENCE: 29

```
gaagtgcagc tggtggagtc tgggggaggc ttagtgaagc ctggagggtc cctgaaactc      60
tcctgtgcag cctctggatt cactttcagt gactattaca tgtattgggt tcgccagact     120
ccggaaaaga ggctggactg ggtcgcaacc attagtgatg gtggtagtta cacctactat     180
ccagacagtg tgaaggggcg attcaccatc tccagagaca atgccaagaa caacctgtac     240
ctgcaaatga gcagtctgaa gtctgaggac acagccatgt attactgtgc aagagattgg     300
aacccctact acggtagtgg ggggggctgg tttggttact ggggccaagg gactctggtc     360
actgcctctg ca                                                          372
```

<210> SEQ ID NO 30
<211> LENGTH: 334
<212> TYPE: DNA
<213> ORGANISM: Artificial Sequence
<220> FEATURE:
<223> OTHER INFORMATION: Anti-ID VL chain

<400> SEQUENCE: 30

```
gacattgtgc tgacccaatc tccagcttct ttggctgtgt ctctagggca gagggccacc      60
atctcctgca aggccagcca aagtgttgat tatgatggtg atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtaatga ggatccattc     300
acgttcggct cggggacaaa gttggaaata aaac                                  334
```

<210> SEQ ID NO 31
<211> LENGTH: 1362
<212> TYPE: DNA
<213> ORGANISM: Artificial Sequence
<220> FEATURE:
<223> OTHER INFORMATION: Anti-ID Heavy chain

<400> SEQUENCE: 31

```
gaagtgcagc tggtggagtc tgggggaggc ttagtgaagc ctggagggtc cctgaaactc      60
tcctgtgcag cctctggatt cactttcagt gactattaca tgtattgggt tcgccagact     120
```

```
ccggaaaaga ggctggactg ggtcgcaacc attagtgatg gtggtagtta cacctactat        180
ccagacagtg tgaaggggcg attcaccatc tccagagaca atgccaagaa caacctgtac        240
ctgcaaatga gcagtctgaa gtctgaggac acagccatgt attactgtgc aagagattgg        300 aaccccttact acggtagtgg gggggctgg tttggttact ggggccaagg gactctggtc        360
actgcctctg cagccaaaac aacagcccca tcggtctatc cactggcccc tgtgtgtgga        420
gatacaactg gctcctcggt gactctagga tgcctggtca agggttattt ccctgagcca        480
gtgaccttga cctggaactc tggatccctg tccagtggtg tgcacacctt cccagctgtc        540
ctgcagtctg acctctacac cctcagcagc tcagtgactg taacctcgag cacctggccc        600
agccagtcca tcacctgcaa tgtggcccac ccggcaagca gcaccaaggt ggacaagaaa        660
attgagccca gagggcccac aatcaagccc tgtcctccat gcaaatgccc agcacctaac        720
ctcttgggtg gaccatccgt cttcatcttc cctccaaaga tcaaggatgt actcatgatc        780
tccctgagcc ccatagtcac atgtgtggtg gtggatgtga gcgaggatga cccagatgtc        840
cagatcagct ggtttgtgaa caacgtggaa gtacacacag ctcagacaca aacccataga        900
gaggattaca acagtactct ccgggtggtc agtgccctcc ccatccagca ccaggactgg        960
atgagtggca aggagttcaa atgcaaggtc aacaacaaag acctcccagc gcccatcgag       1020
agaaccatct caaaacccaa agggtcagta agagctccac aggtatatgt cttgcctcca       1080
ccagaagaag atgatgactaa gaaacaggtc actctgacct gcatggtcac agacttcatg       1140
cctgaagaca tttacgtgga gtggaccaac aacgggaaaa cagagctaaa ctacaagaac       1200
actgaaccag tcctggactc tgatggttct tacttcatgt acagcaagct gagagtggaa       1260
aagaagaact gggtggaaag aaatagctac tcctgttcag tggtccacga gggtctgcac       1320
aatcaccaca cgactaagag cttctcccgg actccgggta aa                          1362
```

```
<210> SEQ ID NO 32
<211> LENGTH: 654
<212> TYPE: DNA
<213> ORGANISM: Artificial Sequence
<220> FEATURE:
<223> OTHER INFORMATION: Anti-ID Light chain

<400> SEQUENCE: 32
```

```
gacattgtgc tgacccaatc tccagcttct ttggctgtgt ctctagggca gagggccacc         60
atctcctgca aggccagcca aagtgttgat tatgatggtg atagttatat gaactggtac        120
caacagaaac aggacagcc acccaaactc ctcatctatg ctgcatccaa tctagaatct        180
gggatcccag ccaggtttag tggcagtggg tctgggacag acttcaccct caacatccat        240
cctgtggagg aggaggatgc tgcaacctat tactgtcagc aaagtaatga ggatccattc        300
acgttcggct cggggacaaa gttggaaata aaacgggctg atgctgcacc aactgtatcc        360
atcttcccac catccagtga gcagttaaca tctggaggtg cctcagtcgt gtgcttcttg        420
aacaacttct accccaaaga catcaatgtc aagtggaaga ttgatggcag tgaacgacaa        480
aatggcgtcc tgaacagttg gactgatcag gacagcaaag acagcaccta cagcatgagc        540
agcaccctca cgttgaccaa ggacgagtat gaacgacata acagctatac ctgtgaggcc        600
actcacaaga catcaacttc acccattgtc aagagcttca acaggaatga gtgt            654
```

```
<210> SEQ ID NO 33
<211> LENGTH: 357
<212> TYPE: PRT
```

-continued

<213> ORGANISM: Artificial Sequence
<220> FEATURE:
<223> OTHER INFORMATION: Truncated EGFR (tEGFR)

<400> SEQUENCE: 33

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65              70                  75                  80

Leu Asp Ile Leu Lys Thr Val Lys Glu Ile Thr Gly Phe Leu Leu Ile
            85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
            165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
        210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
            245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
    275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
            325                 330                 335

Thr Gly Met Val Gly Ala Leu Leu Leu Leu Leu Val Val Ala Leu Gly
            340                 345                 350

Ile Gly Leu Phe Met
        355
```

<210> SEQ ID NO 34
<211> LENGTH: 41
<212> TYPE: PRT

<213> ORGANISM: Homo sapiens
<220> FEATURE:
<223> OTHER INFORMATION: CD28 (amino acids 180-220 of P10747)

<400> SEQUENCE: 34

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 35
<211> LENGTH: 41
<212> TYPE: PRT
<213> ORGANISM: Homo sapiens
<220> FEATURE:
<223> OTHER INFORMATION: CD28 (LL to GG)

<400> SEQUENCE: 35

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 36
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 36

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
            85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 37
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 37

Glu Ser Lys Tyr Gly Pro Pro Cys Pro Pro Cys Pro Ala Pro Glu Phe

```
1                5              10             15

Leu Gly Gly Pro Ser Val Phe Leu Phe Pro Pro Lys Pro Lys Asp Thr
             20              25              30

Leu Met Ile Ser Arg Thr Pro Glu Val Thr Cys Val Val Val Asp Val
         35              40              45

Ser Gln Glu Asp Pro Glu Val Gln Phe Asn Trp Tyr Val Asp Gly Val
     50              55              60

Glu Val His Asn Ala Lys Thr Lys Pro Arg Glu Glu Gln Phe Asn Ser
65               70              75              80

Thr Tyr Arg Val Val Ser Val Leu Thr Val Leu His Gln Asp Trp Leu
             85              90              95

Asn Gly Lys Glu Tyr Lys Cys Lys Val Ser Asn Lys Gly Leu Pro Ser
             100             105             110

Ser Ile Glu Lys Thr Ile Ser Lys Ala Lys Gly Gln Pro Arg Glu Pro
         115             120             125

Gln Val Tyr Thr Leu Pro Pro Ser Gln Glu Glu Met Thr Lys Asn Gln
     130             135             140

Val Ser Leu Thr Cys Leu Val Lys Gly Phe Tyr Pro Ser Asp Ile Ala
145             150             155             160

Val Glu Trp Glu Ser Asn Gly Gln Pro Glu Asn Asn Tyr Lys Thr Thr
             165             170             175

Pro Pro Val Leu Asp Ser Asp Gly Ser Phe Phe Leu Tyr Ser Arg Leu
             180             185             190

Thr Val Asp Lys Ser Arg Trp Gln Glu Gly Asn Val Phe Ser Cys Ser
             195             200             205

Val Met His Glu Ala Leu His Asn His Tyr Thr Gln Lys Ser Leu Ser
     210             215             220

Leu Ser Leu Gly Lys
225

<210> SEQ ID NO 38
<211> LENGTH: 24
<212> TYPE: PRT
<213> ORGANISM: Artificial Sequence
<220> FEATURE:
<223> OTHER INFORMATION: T2A peptide

<400> SEQUENCE: 38

Leu Glu Gly Gly Gly Glu Gly Arg Gly Ser Leu Leu Thr Cys Gly Asp
1                5              10             15

Val Glu Glu Asn Pro Gly Pro Arg
             20

<210> SEQ ID NO 39
<211> LENGTH: 19
<212> TYPE: PRT
<213> ORGANISM: Artificial Sequence
<220> FEATURE:
<223> OTHER INFORMATION: P2A peptide

<400> SEQUENCE: 39

Ala Thr Asn Phe Ser Leu Leu Lys Gln Ala Gly Asp Val Glu Glu Asn
1                5              10             15

Pro Gly Pro

<210> SEQ ID NO 40
<211> LENGTH: 22
<212> TYPE: PRT
```

<213> ORGANISM: Artificial Sequence
<220> FEATURE:
<223> OTHER INFORMATION: P2A peptide

<400> SEQUENCE: 40

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 41
<211> LENGTH: 20
<212> TYPE: PRT
<213> ORGANISM: Artificial Sequence
<220> FEATURE:
<223> OTHER INFORMATION: E2A peptide

<400> SEQUENCE: 41

Gln Cys Thr Asn Tyr Ala Leu Leu Lys Leu Ala Gly Asp Val Glu Ser
1               5                   10                  15

Asn Pro Gly Pro
            20

<210> SEQ ID NO 42
<211> LENGTH: 23
<212> TYPE: PRT
<213> ORGANISM: Artificial Sequence
<220> FEATURE:
<223> OTHER INFORMATION: E2A peptide

<400> SEQUENCE: 42

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 43
<211> LENGTH: 22
<212> TYPE: PRT
<213> ORGANISM: Artificial Sequence
<220> FEATURE:
<223> OTHER INFORMATION: F2A peptide

<400> SEQUENCE: 43

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 44
<211> LENGTH: 25
<212> TYPE: PRT
<213> ORGANISM: Artificial Sequence
<220> FEATURE:
<223> OTHER INFORMATION: F2A peptide

<400> SEQUENCE: 44

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 45
<211> LENGTH: 18

-continued

```
<212> TYPE: PRT
<213> ORGANISM: Artificial Sequence
<220> FEATURE:
<223> OTHER INFORMATION: T2A peptide

<400> SEQUENCE: 45

Glu Gly Arg Gly Ser Leu Leu Thr Cys Gly Asp Val Glu Glu Asn Pro
1               5                   10                  15

Gly Pro
```

ANTI-IDIOTYPIC ANTIBODIES TO GPRC5D-TARGETED BINDING DOMAINS AND RELATED COMPOSITIONS AND METHODS

CROSS-REFERENCE TO RELATED APPLICATIONS

This application is a national stage application under 35 U.S.C. § 371 of International Application No. PCT/US2020/063497, filed internationally on Dec. 4, 2020, which claims priority to U.S. provisional application 62/945,064, filed Dec. 6, 2019, entitled "ANTI-IDIOTYPIC ANTI-BODIES TO GPRC5D-TARGETED BINDING DOMAINS AND RELATED COMPOSITIONS AND METHODS," and U.S. provisional application 63/061,757, filed Aug. 5, 2020, entitled "ANTI-IDIOTYPIC ANTIBODIES TO GPRC5D-TARGETED BINDING DOMAINS AND RELATED COMPOSITIONS AND METHODS," the contents of which are incorporated by reference in their entirety for all purposes.

INCORPORATION BY REFERENCE OF SEQUENCE LISTING

The present application is being filed along with a Sequence Listing in electronic format. The Sequence Listing is provided as a file entitled 735042022600SeqList.txt, created May 31, 2022, which is 30,980 bytes in size. The information in the electronic format of the Sequence Listing is incorporated by reference in its entirety.

FIELD

The present disclosure relates in some aspects to anti-idiotype antibodies that bind to or recognize antibodies against G Protein-Coupled Receptor Class C Group 5 Member D (GPRC5D), i.e., anti-GPRC5D antibody moieties, in particular, anti-GPRC5D antibody moieties present in recombinant receptors, including chimeric antigen receptors (CARs). The disclosure further relates to uses of anti-idiotype antibodies for specifically identifying, detecting or selecting cells expressing such recombinant receptors, such as anti-GPRC5D CAR T cells. The disclosure further relates to uses of anti-idiotype antibodies for specifically activating such cells.

BACKGROUND

Methods are available for adoptive cell therapy using engineered cells expressing recombinant receptors, such as chimeric antigen receptor (CARs) containing extracellular antibody antigen-binding domains. Various strategies are available to assess activity of such cells either in vitro or upon in vivo to a subject. Improved methods are needed to specifically assess activity of CAR-expressing cells. Provided are reagents, compositions, and articles of manufacture that meet such needs.

SUMMARY

Provided herein are agents that bind to or recognize antibodies and antigen-binding fragments thereof, including antibody fragments such as scFvs, and chimeric molecules containing the same, such as chimeric antigen receptors. Also provided are compositions and articles of manufacture containing such agents, including those including a surface to which the agent is bound, such as a solid surface, e.g. a plate or bead. Also among the embodiments provided herein are uses and methods of using such agents, compositions and articles, including for detection, use, manipulation and/or stimulation of cells or therapies containing or suspected of containing the antibody or chimeric molecule, such as in the detection, stimulation or use of CAR-expressing cells.

Provided herein, in some embodiments, is an anti-idiotype antibody or antigen-binding fragment thereof that binds to or recognizes an anti-GPRC5D target antibody or antigen-binding fragment thereof, wherein the anti-idiotype antibody or antigen-binding fragment comprises: a heavy chain variable (VH) region comprising the amino acid sequence set forth in SEQ ID NO: 25; and a light chain variable (VL) region comprising the amino acid sequence set forth in SEQ ID NO: 26.

Also provided herein, in some embodiments, is an anti-idiotype antibody or antigen-binding fragment thereof that binds to or recognizes an anti-GPRC5D target antibody or antigen-binding fragment thereof, wherein the anti-idiotype antibody or antigen-binding fragment comprises: a VH region comprising an amino acid sequence having at least 90% sequence identity to the amino acid sequence set forth in SEQ ID NO: 25; and a VL region comprising an amino acid sequence having at least 90% sequence identity to the amino acid sequence set forth in SEQ ID NO: 26.

Also provided herein, in some embodiments, is an anti-idiotype antibody or antigen-binding fragment thereof that binds to or recognizes an anti-GPRC5D target antibody or antigen-binding fragment thereof, wherein the anti-idiotype antibody or antigen-binding fragment comprises: a VH region comprising a heavy chain complementarity-determining region 1 (CDR-H1) comprising the amino acid sequence set forth in SEQ ID NO: 15, a CDR-H2 comprising the amino acid sequence set forth in SEQ ID NO: 16, and a CDR-H3 comprising the amino acid sequence set forth in SEQ ID NO: 17; and a VL region comprising a light chain complementarity-determining region 1 (CDR-L1) comprising the amino acid sequence set forth in SEQ ID NO: 22, a CDR-L2 comprising the amino acid sequence set forth in SEQ ID NO: 23, and a CDR-L3 comprising the amino acid sequence set forth in SEQ ID NO: 24.

Also provided herein, in some embodiments, is an anti-idiotype antibody or antigen-binding fragment thereof that binds to or recognizes an anti-GPRC5D target antibody or antigen-binding fragment thereof, wherein the anti-idiotype antibody or antigen-binding fragment thereof comprises: a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 25; and a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 26.

In some of any such embodiments, the VH region comprises a CDR-H1 comprising the amino acid sequence set forth in SEQ ID NO: 15, a CDR-H2 comprising the amino acid sequence set forth in SEQ ID NO: 16, and a CDR-H3 comprising the amino acid sequence set forth in SEQ ID NO: 17; and the VL region comprises a CDR-L1 comprising the amino acid sequence set forth in SEQ ID NO: 22, a CDR-L2 comprising the amino acid sequence set forth in SEQ ID NO: 23, and a CDR-L3 comprising the amino acid sequence set forth in SEQ ID NO: 24.

In some of any such embodiments, the VH region comprises an amino acid sequence having at least 90% sequence identity to the amino acid sequence set forth in SEQ ID NO: 25; and the VL region comprises an amino acid sequence having at least 90% sequence identity to the amino acid sequence set forth in SEQ ID NO: 26. In some of any such embodiments, the VH region comprises the amino acid sequence set forth in SEQ ID NO: 25; and the VL region comprises the amino acid sequence set forth in SEQ ID NO: 26.

In some of any such embodiments, the anti-idiotype antibody or antigen-binding fragment thereof comprises: a heavy chain comprising an amino acid sequence having at least 90% sequence identity to the amino acid sequence set forth in SEQ ID NO: 27; and a light chain comprising an amino acid sequence having at least 90% sequence identity to the amino acid sequence set forth in SEQ ID NO: 28. In some of any such embodiments, the anti-idiotype antibody or antigen-binding fragment thereof comprises: a heavy chain comprising an amino acid sequence set forth in SEQ ID NO: 27; and a light chain comprising an amino acid sequence set forth in SEQ ID NO: 28.

In some of any such embodiments, the anti-GPRC5D target antibody or antigen-binding fragment thereof comprises a VH region comprising the amino acid sequence set forth in SEQ ID NO: 7, and a VL region comprising the amino acid sequence set forth in SEQ ID NO: 8.

In some of any such embodiments, the anti-GPRC5D target antibody or antigen-binding fragment thereof is a single chain fragment.

In some of any such embodiments, the single chain fragment comprises a flexible linker positioned between the VH region and the VL region. In some of any such embodiments, the flexible linker comprises the amino acid sequence set forth in SEQ ID NO: 10.

In some of any such embodiments, the single chain fragment of the anti-GPRC5D target antibody or antigen binding fragment is a single chain variable fragment (scFv). In some of any such embodiments, the scFv comprises the amino acid sequence set forth in SEQ ID NO: 9.

In some of any such embodiments, the anti-idiotype antibody or antigen-binding fragment thereof binds to or recognizes an epitope within or including all or a portion of a complementarity determining region (CDR) of the anti-GPRC5D target antibody or antigen-binding fragment thereof.

In some of any such embodiments, the anti-GPRC5D target antibody or antigen-binding fragment thereof is within or included in an antigen-binding domain of an extracellular portion of a chimeric antigen receptor (CAR); and/or the anti-idiotype antibody or antigen-binding fragment thereof binds the anti-GPRC5D target antibody or antigen-binding fragment thereof comprised within or included in an antigen-binding domain of an extracellular portion of a CAR.

In some of any such embodiments, the anti-GPRC5D target antibody or antigen-binding fragment thereof is within or included in an antigen-binding domain of an extracellular portion of a chimeric antigen receptor (CAR); and/or the anti-idiotype antibody or antigen-binding fragment thereof specifically binds the anti-GPRC5D target antibody or antigen-binding fragment thereof comprised within or included in an antigen-binding domain of an extracellular portion of a CAR. In some of any such embodiments, the scFv is within or included in an extracellular portion of a CAR; and/or the anti-idiotype antibody or antigen-binding fragment thereof binds the scFv comprised within or included in an extracellular portion of a CAR. In some of any such embodiments, the scFv is within or included in an extracellular portion of a CAR; and/or the anti-idiotype antibody or antigen-binding fragment thereof specifically binds the scFv comprised within or included in an extracellular portion of a CAR. In some embodiments, the CAR contains an extracellular domain containing an antigen-binding domain that is or includes the anti-GPRC5D target antibody or antigen-binding fragment thereof, such as an scFv, e.g. set forth in SEQ ID NO:9; a transmembrane domain, and an intracellular domain containing a CD3zeta signaling domain and a costimulatory signaling domain. In some embodiments, the costimulatory signaling domain is an intracellular signaling domain of CD28, such as from a human CD28. In some embodiments, the costimulatory signaling domain is an intracellular signaling domain of 4-1BB, such as from a human 4-1BB. In some of any such embodiments, the CAR further comprises a transmembrane domain linked to the antigen-binding domain via a spacer. In some of any such embodiments, the spacer is an immunoglobulin spacer, optionally wherein the spacer comprises the amino acid sequence set forth in SEQ ID NO: 11. In some of any such embodiments, the spacer comprises the amino acid sequence set forth in SEQ ID NO: 11. In some of any such embodiments, the transmembrane domain comprises a transmembrane portion of CD28, which optionally is human CD28. In some of any such embodiments, the transmembrane domain comprises a transmembrane portion of human CD28.

In some of any such embodiments, the anti-idiotype antibody or antigen-binding fragment thereof does not bind to an epitope in the spacer domain of the CAR. In some of any such embodiments, the anti-idiotype antibody or antigen-binding fragment thereof does not bind or does not specifically bind to CD28 or a portion thereof, which optionally is human CD28. In some of any such embodiments, the anti-idiotype antibody or antigen-binding fragment thereof does not bind or does not specifically bind to human CD28 or a portion thereof.

In some of any such embodiments, the anti-idiotype antibody or antigen-binding fragment thereof does not bind to an epitope in an Fc domain, which optionally is a human IgG1 Fc domain. In some of any such embodiments, the anti-idiotype antibody or antigen-binding fragment thereof does not bind to an epitope in a human IgG1 Fc domain.

In some of any such embodiments, the anti-GPRC5D target antibody or antigen-binding fragment thereof binds to or recognizes human G Protein-Coupled Receptor Class C Group 5 Member D (GPRC5D).

In some of any such embodiments, the anti-idiotype antibody or antigen-binding fragment thereof is an agonist of a CAR comprising the anti-GPRC5D target antibody or antigen-binding fragment thereof.

In some of any such embodiments, the anti-idiotype antibody or antigen-binding fragment thereof is an agonist of the CAR when in solution.

In some of any such embodiments, the anti-idiotype antibody or antigen-binding fragment thereof is an agonist of the CAR when immobilized to a support or a stationary phase, optionally wherein the support or stationary phase is a plate or a bead. In some embodiments, the support is a plate or a bead.

In some of any such embodiments, the anti-idiotype antibody or antigen-binding fragment thereof specifically binds to the anti-GPRC5D target antibody or antigen-binding fragment thereof.

In some of any such embodiments, the anti-idiotype antibody or antigen-binding fragment thereof has a binding affinity (EC50) and/or a dissociation constant to the anti-GPRC5D target antibody or antigen-binding fragment thereof that is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, or 1 nM. In some of any such embodiments, the anti-idiotype antibody or antigen-binding fragment thereof has a dissociation constant to the anti-GPRC5D target antibody or antigen-binding fragment thereof that is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM.

In some of any such embodiments, the anti-idiotype antibody or antigen-binding fragment thereof is humanized. In some of any such embodiments, the anti-idiotype antibody or antigen-binding fragment thereof is recombinant. In some of any such embodiments, the anti-idiotype antibody or antigen-binding fragment thereof is monoclonal.

In some of any such embodiments, the anti-idiotype antibody or antigen-binding fragment thereof is an antigen-binding fragment.

In some of any such embodiments, the antigen-binding fragment is selected from among Fab fragments, F(ab')2 fragments, Fab' fragments, Fv fragments, an scFv, and a single domain antibody.

In some of any such embodiments, the anti-idiotype antibody or antigen-binding fragment thereof comprises at least a portion of an immunoglobulin constant region. In some of any such embodiments, the at least a portion of an immunoglobulin constant region comprises an Fc region or a portion of the Fc comprising the CH2 and CH3 domains. In some of any such embodiments, the constant region is derived from human IgG.

In some of any such embodiments, the anti-idiotype antibody or antigen-binding fragment thereof comprises at least a portion of an immunoglobulin constant region of a heavy chain and/or a light chain. In some of any such embodiments, the anti-idiotype antibody or antigen-binding fragment comprises a heavy chain constant region comprising an Fc region or a portion of the Fc comprising the CH2 and CH3 domains and/or a light chain constant region comprising a CL domain. In some of any such embodiments, the constant region is from IgG, optionally IgG1. In some of any such embodiments, the constant region is from IgG1. In some of any such embodiments, the light chain constant region is from a kappa light chain.

In some of any such embodiments, the anti-idiotype antibody or antigen-binding fragment thereof is an intact antibody or full-length antibody.

Also provided herein, in some embodiments, is a conjugate, comprising the anti-idiotype antibody or antigen-binding fragment thereof of any one of such embodiments and a heterologous molecule or moiety.

In some of any such embodiments, the heterologous molecule or moiety is a label. In some of any such embodiments, the label is selected from a fluorescent dye, a fluorescent protein, a radioisotope, a chromophore, a metal ion, a gold particle, a silver particle, a magnetic particle, a polypeptide, an enzyme, a streptavidin, a biotin, a luminescent compound, and an oligonucleotide. In some of any such embodiments, the heterologous molecule or moiety is a protein, peptide, nucleic acid or small molecule, which optionally is or comprises a toxin or a Strep-Tag. In some of any such embodiments, the heterologous molecule or moiety is or comprises a Strep-Tag.

Also provided herein, in some embodiments, is a nucleic acid molecule(s) encoding the heavy chain and/or the light chain of the anti-idiotype antibody or antigen-binding fragment thereof of any one of such embodiments.

In some of any such embodiments, the nucleic acid molecule(s) comprise: a sequence of nucleotides encoding (i) the heavy chain variable region set forth in SEQ ID NO: 25, (ii) a heavy chain variable region that has at least 90% sequence identity to the amino acid sequence set forth in SEQ ID NO: 25; or (iii) a degenerate sequence of (i) or (ii); and a sequence of nucleotides encoding (iv) the light chain variable region set forth in SEQ ID NO: 26, (v) a light chain variable region that has at least 90% sequence identity to the amino acid sequence set forth in SEQ ID NO: 26; or (vi) a degenerate sequence of (iv) or (v).

In some of any such embodiments, the nucleic acid molecule(s) comprise: a sequence of nucleotides encoding (i) the heavy chain set forth in SEQ ID NO: 27, (ii) a heavy chain that has at least 90% sequence identity to the amino acid sequence set forth in SEQ ID NO: 27; or (iii) a degenerate sequence of (i) or (ii); and a sequence of nucleotides encoding (iv) the light chain set forth in SEQ ID NO: 28, (v) a light chain that has at least 90% sequence identity to the amino acid sequence set forth in SEQ ID NO: 28; or (vi) a degenerate sequence of (iv) or (v).

In some of any such embodiments, the nucleotide sequence encoding the heavy chain and/or light chain comprises a signal sequence. In some of any such embodiments, the nucleic acid molecule(s) comprise one or more nucleotide sequences selected from the group consisting of SEQ ID NOs: 29-32.

Also provided herein, in some embodiments, is a vector, comprising the nucleic acid molecule(s) of any one of such embodiments.

Also provided herein, in some embodiments, is a cell, comprising the anti-idiotype antibody or antigen-binding fragment thereof of any one of such embodiments, the nucleic acid molecule of any one of such embodiments, or the vector of any one of such embodiments.

Also provided herein, in some embodiments, is a method of producing an anti-idiotype antibody or antigen-binding fragment thereof, comprising expressing the heavy and/or light chain encoded by the nucleic acid molecule(s) of any one of such embodiments or the vector of any one of such embodiments in a suitable host cell and recovering or isolating the antibody.

Also provided herein, in some embodiments, is a method of producing an anti-idiotype antibody or antigen-binding fragment thereof, comprising culturing the cell of any one of such embodiments under conditions in which the heavy chain and/or light chain is expressed, and recovering or isolating the antibody.

Also provided herein, in some embodiments, is an anti-idiotype antibody or antigen-binding fragment thereof produced by the method of any one of such embodiments.

Also provided herein, in some embodiments, is a composition comprising the anti-idiotype antibody or antigen-binding fragment thereof of any one of such embodiments, the conjugate of any one of such embodiments, or the cell of any one of such embodiments.

In some of any such embodiments, the composition further comprises a pharmaceutically acceptable excipient.

Also provided herein, in some embodiments, is a kit, comprising one or more of the anti-idiotype antibody or antigen-binding fragment thereof of any one of such embodiments, the conjugate of any one of such embodiments, and the nucleic acid molecule(s) of any one of such embodiments, and, optionally, instructions for use.

In some of any such embodiments, the kit further comprises a reagent or support for immobilizing the anti-idiotype antibody or antigen-binding fragment thereof or the conjugate, wherein said reagent or support is a bead, a column, a microwell, a stick, a filter, a strip or a soluble oligomeric streptavidin mutein reagent.

Also provided herein, in some embodiments, is a method of detecting a target antibody or antigen-binding fragment thereof, comprising: (a) contacting a composition comprising a target antibody or antigen-binding fragment thereof with the anti-idiotype antibody or antigen-binding fragment thereof of any one of such embodiments or the conjugate of any one of such embodiments that specifically binds to the target antibody or antigen-binding fragment thereof, and (b) detecting the anti-idiotype antibody bound to the target antibody or antigen-binding fragment thereof.

In some of any such embodiments, the target antibody or antigen-binding fragment thereof is bound to a cell or expressed on the surface of a cell, and the detecting in (b) comprises detecting cells bound with the anti-idiotype antibody or antigen-binding fragment thereof.

In some of any such embodiments, the cell expresses on its surface a CAR comprising the target antibody or antigen-binding fragment thereof.

Also provided herein, in some embodiments, is a method of detecting a CAR comprising a target antibody or antigen-binding fragment thereof, comprising: (a) contacting a cell expressing a CAR comprising a target antibody or antigen-binding fragment thereof with the anti-idiotype antibody or antigen-binding fragment thereof of any one of such embodiments, or the conjugate of any one of such embodiments, that specifically binds to the target antibody or antigen-binding fragment thereof, and (b) detecting cells bound with the anti-idiotype antibody or antigen-binding fragment thereof. In some of any such embodiments, the anti-idiotype antibody or antigen-binding fragment thereof is directly or indirectly labeled for detection.

Also provided herein, in some embodiments, is a method of selecting cells from a cell population, comprising: (a) contacting a cell population expressing a CAR comprising a target antibody or antigen-binding fragment thereof or a cell bound to a target antibody or antigen-binding fragment thereof with the anti-idiotype antibody or antigen-binding fragment thereof of any one of such embodiments, or the conjugate of any one of such embodiments, that specifically binds to the target antibody or antigen-binding fragment thereof, and (b) selecting cells bound with the anti-idiotype antibody or antigen-binding fragment thereof.

In some of any such embodiments, the cells bound with the anti-idiotype antibody or antigen-binding fragment thereof are selected by affinity-based separation. In some of any such embodiments, the affinity-based separation is immunoaffinity-based separation. In some of any such embodiments, the affinity-based separation is by flow cytometry. In some of any such embodiments, the affinity-based separation is by magnetic activated cell sorting. In some of any such embodiments, the affinity-based separation comprises affinity chromatography. In some of any such embodiments, the anti-idiotype antibody or antigen-binding fragment thereof is reversibly bound or immobilized to a support or a stationary phase.

Also provided herein, in some embodiments, is a method of stimulating cells, comprising incubating an input composition comprising cells expressing a CAR comprising a target antibody or antigen-binding fragment thereof with the anti-idiotype antibody or antigen-binding fragment thereof of any one of such embodiments, or the conjugate of any one of such embodiments, that specifically binds to the target antibody or antigen-binding fragment thereof, thereby generating an output composition comprising stimulated cells.

Also provided herein, in some embodiments, is a method of producing a cell composition, comprising: (a) introducing into cells a nucleic acid molecule(s) encoding a CAR, thereby generating an input composition; and (b) incubating the input composition with the anti-idiotype antibody or antigen-binding fragment thereof of any one of such embodiments, or the conjugate of any one of such embodiments, that specifically binds to an antigen receptor of the CAR, thereby producing the cell composition.

In some of any such embodiments, the introducing in (a) comprises introducing the nucleic acid molecule(s) into the cells by viral transduction, transposition, electroporation, or chemical transfection.

In some of any such embodiments, the introducing in (a) comprises introducing the nucleic acid molecule(s) in the cells by transduction with a viral vector comprising the nucleic acid molecule(s), optionally wherein the viral vector is a retroviral vector or a lentiviral vector. In some embodiments, the viral vector is a retroviral vector or a lentiviral vector.

In some of any such embodiments, the introducing in (a) comprises introducing the nucleic acid molecule(s) in the cells by transposition with a transposon comprising the nucleic acid molecule(s).

In some of any such embodiments, the introducing in (a) comprises introducing the nucleic acid molecule(s) in the cells by electroporation or transfection of a vector comprising the nucleic acid molecule(s).

In some of any such embodiments, the method further comprises a step of activating the cells prior to step (a). In some of any such embodiments, the step of activating the cells comprises contacting the cells with an agonist of CD3 and optionally an agonist of CD28. In some of any such embodiments, the step of activating the cells comprises contacting the cells with a reagent comprising agonistic anti-CD3 and anti-CD28 antibodies.

In some of any such embodiments, the incubation is performed under conditions in which the anti-idiotype antibody or antigen-binding fragment thereof binds to the CAR, thereby inducing or modulating a signal in one or more cells in the input composition. In some of any such embodiments, the cells comprise T cells. In some of any such embodiments, the T cells comprise CD4+ and/or CD8+ T cells.

In some of any such embodiments, the anti-idiotype antibody or antigen-binding fragment thereof is immobilized to a solid support, which optionally comprises or is conjugated to a reagent comprising a plurality of binding sites capable of reversibly binding to the anti-idiotype antibody or antigen-binding fragment thereof. In some of any such embodiments, the anti-idiotype antibody or antigen-binding fragment thereof is immobilized to a soluble reagent, which optionally is or comprises a plurality of binding sites capable of reversibly binding to the anti-idiotype antibody or antigen-binding fragment thereof. In some of any such embodiments, the reagent comprises a streptavidin mutein.

In some of any such embodiments, the incubation is for at least or about at least 5 minutes, 10 minutes, 30 minutes, 60 minutes, 2 hours, 6 hours, 12 hours, 24 hours, 36, 48 hours, 72 hours or 96 hours.

In some of any such embodiments, the input composition comprises less than or less than about 60%, less than or less than about 50%, less than or less than about 40%, less than or less than about 30%, less than or less than about 20% or less than or less than about 10% CAR-expressing cells as a percentage of the total cells in the composition.

In some of any such embodiments, the number of CAR-expressing cells in the output composition is increased by greater than 1.2-fold, 1.5-fold, 2.0-fold, 3.0-fold, 4.0-fold, 5.0-fold, 10-fold or more compared to the number of CAR-expressing cells in the input composition; and/or the percentage of CAR-expressing in the output composition compared to the total cells in the composition is increased by greater than 10%, 20%, 40%, 50%, 60%, 70%, 80% or more.

In some of any such embodiments, prior to the introducing and/or the incubating, the cells are not selected or enriched for CAR-expressing cells.

Also provided herein, in some embodiments, is a method of purifying an anti-idiotype antibody or antigen-binding fragment thereof, comprising: (a) contacting a composition comprising a target antibody or antigen-binding fragment thereof with the anti-idiotype antibody or antigen-binding fragment thereof of any one of such embodiments, or the conjugate of any one of such embodiments, that specifically binds to the target antibody or antigen-binding fragment thereof, and (b) isolating complexes comprising the anti-idiotype antibody or antigen-binding fragment thereof.

In some of any such embodiments, the complexes comprising the anti-idiotype antibody or antigen-binding fragment thereof are isolated by affinity-based separation. In some of any such embodiments, the affinity-based separation is immunoaffinity-based separation. In some of any such embodiments, the affinity-based separation is magnetic-based separation. In some of any such embodiments, the affinity-based separation comprises affinity chromatography.

Also provided herein, in some embodiments, is a method of depleting cells, comprising administering, to a subject, a composition comprising the anti-idiotype antibody or antigen-binding fragment thereof of any one of such embodiments, or the conjugate of any one of such embodiments, that specifically binds to a target antibody or antigen-binding fragment thereof, wherein the subject has been administered a cell expressing a CAR comprising the target antibody or antigen-binding fragment thereof.

In some of any such embodiments, the depletion occurs via antibody-dependent cell-mediated cytotoxicity (ADCC).

In some of any such embodiments, the target antibody or antigen-binding fragment thereof is a single chain fragment.

In some of any such embodiments, the single chain fragment comprises an scFv. In some of any such embodiments, the single chain fragment is a single-chain variable fragment (scFv).

In some of any such embodiments, the target antibody or antigen-binding fragment thereof comprises a VH region comprising the amino acid sequence set forth in SEQ ID NO: 7, and a VL region comprising the amino acid sequence set forth in SEQ ID NO: 8.

In some of any such embodiments, the target antibody or antigen-binding fragment thereof is an scFv and the VH region and the VL region are joined by a flexible linker. In some of any such embodiments, the flexible linker comprises the amino acid sequence set forth in SEQ ID NO: 10, and the scFv comprises the amino acid sequence set forth in SEQ ID NO: 9.

Also provided herein, in some embodiments, is an article of manufacture comprising the anti-idiotype antibody or antigen-binding fragment thereof of any one of such embodiments, or the conjugate of any one of such embodiments, and instructions for using the anti-idiotype antibody or antigen-binding fragment thereof to: detect a target antibody or antigen-binding fragment thereof or a CAR comprising the target antibody or antigen-binding fragment thereof; and/or select or enrich, from a population of cells, engineered cells expressing a CAR comprising the target antibody or antigen-binding fragment thereof; and/or stimulate an input composition comprising cells expressing a CAR comprising the target antibody or antigen-binding fragment thereof.

Also provided herein, in some embodiments, is an article of manufacture comprising: a binding reagent comprising an extracellular domain of a CAR comprising a target antibody or antigen-binding fragment thereof, said extracellular domain or portion thereof comprising the target antibody or antigen-binding fragment thereof; and an anti-idiotype antibody or antigen-binding fragment of any of such embodiments, or the conjugate of any one of such embodiments.

In some of any such embodiments, the binding reagent is a first binding reagent and the article of manufacture further comprises a second binding reagent comprising the extracellular domain or portion thereof of the CAR.

In some of any such embodiments, the extracellular domain of the CAR or portion thereof of the first and second binding reagent is the same.

In some of any such embodiments, the article of manufacture further comprises instructions for using the binding reagent, optionally the first and second binding reagent, for assaying a sample for the presence or absence of a molecule that binds to the binding reagent using an immunoassay, optionally wherein the immunoassay is a bridge or sandwich immunoassay, optionally wherein the sample is from a subject having been administered a cell therapy comprising cells engineered with a CAR comprising a target antibody that is the or antigen-binding fragment thereof.

In some of any such embodiments, the binding reagent, optionally the first and/or second binding reagent, is detectably labeled or capable of producing a detectable signal.

In some of any such embodiments, one of the first and second binding reagent is attached to a solid support of is capable of being attached to a solid support and the other of the first and second binding reagent is detectably labeled or is capable of producing a detectable signal.

In some of any such embodiments, the article of manufacture further comprises a solid support, optionally wherein the one of the first and second binding reagent is linked, directly or indirectly to biotin, and the solid support comprises a streptavidin-coated surface.

In some of any such embodiments, wherein the target antibody or antigen-binding fragment thereof is a single chain fragment. In some of any such embodiments, the single chain fragment comprises an scFv. In some of any such embodiments, the single chain fragment is a single-chain variable fragment (scFv).

In some of any such embodiments, the target antibody or antigen-binding fragment thereof comprises a VH region comprising the amino acid sequence set forth in SEQ ID NO: 7, and a VL region comprising the amino acid sequence set forth in SEQ ID NO: 8.

In some of any such embodiments, the target antibody or antigen-binding fragment thereof is an scFv and the VH region and the VL region are joined by a flexible linker. In some of any such embodiments, the flexible linker comprises the amino acid sequence set forth in SEQ ID NO: 10, and the scFv comprises the amino acid sequence set forth in SEQ ID NO: 9.

DETAILED DESCRIPTION

Figure 1A:
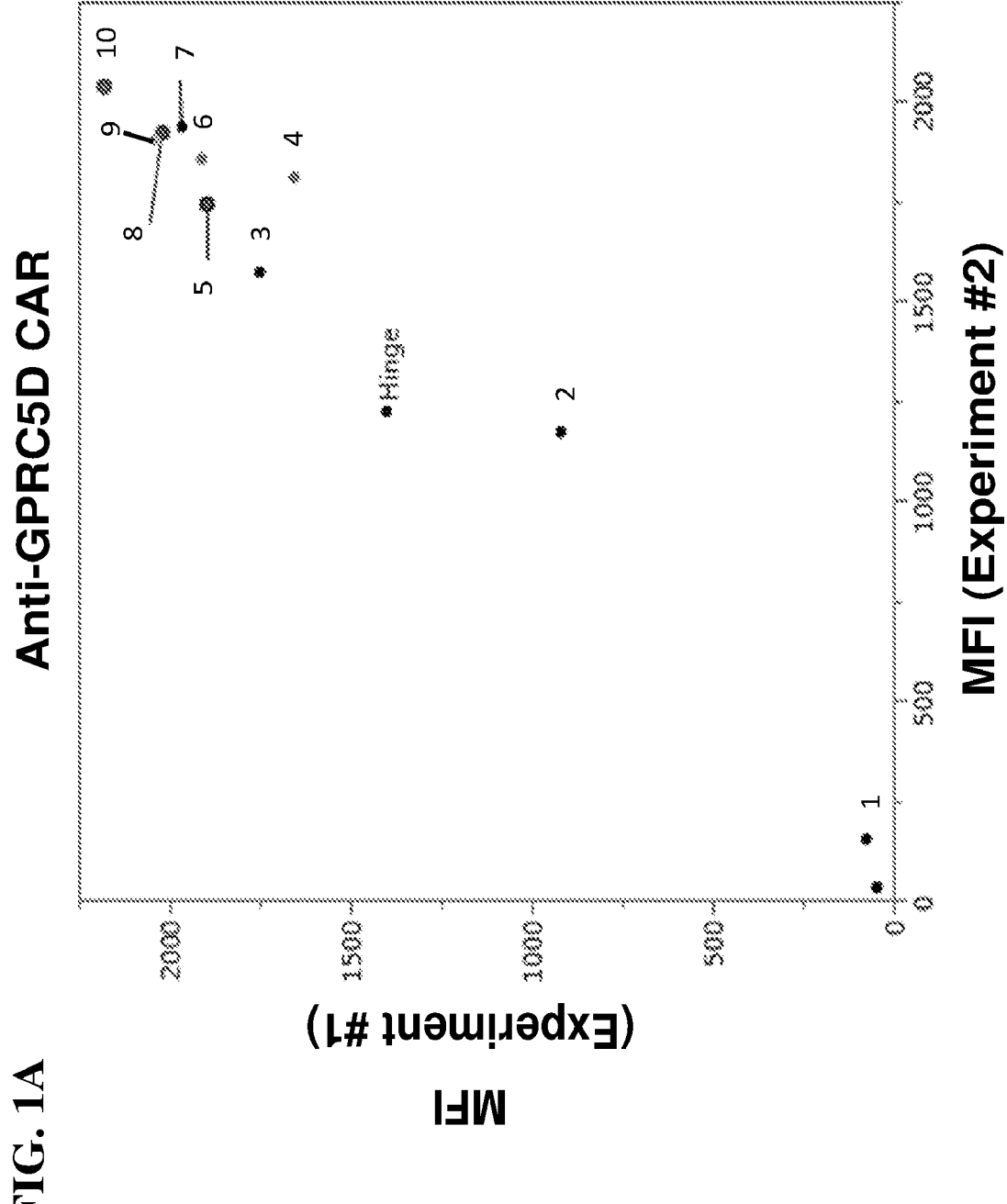
FIGS. 1A and 1B depict the results of assays where anti-idiotype (anti-ID) antibodies were assessed for the ability to specifically bind to T cells engineered with the anti-GPRC5D CAR by incubating the anti-ID antibodies with T cells engineered with the anti-GPRC5D CAR, or a Control CAR, and then detecting the level of binding.

Provided herein are agents such as anti-idiotype antibodies and antigen-binding fragments thereof that bind to or recognize anti-GPRC5D antibody moieties (such as anti-GPRC5D antibody moieties present in recombinant receptors, including chimeric antigen receptors). Also provided are uses and methods of use thereof, and compositions and articles of manufacture including such agents, including for specifically identifying, selecting, and/or stimulating and/or activating cells expressing or including the target antibodies or fragments such as anti-GPRC5D CAR T cells. In some embodiments, the provided antibodies can be used for specific identification and/or selection of various anti-GPRC5D CARs, such as CARs bound to or expressed on a cell surface, and can also be used to specifically activate cells expressing target CARs, such as CAR T cells. In some embodiments, provided are antibodies that are specific to the provided anti-GPRC5D antibody, or an antibody fragment derived therefrom, including antibodies and CARs containing variable regions derived from such antibodies, and/or an antibody containing an idiotope contained therein.

In some embodiments, provided are anti-idiotype antibodies or antigen-binding fragments thereof that are specific to an anti-GPRC5D antibody or an antibody fragment derived therefrom, including anti-GPRC5D antibodies and CARs containing variable regions derived from such anti-GPRC5D antibodies and/or an anti-GPRC5D antibody containing an idiotope contained therein. The provided anti-idiotype antibodies or antigen-binding fragments thereof can be utilized as a reagent for various purposes, including based on ability to detect, identity or select or identify a target antibody present in a recombinant receptor (e.g. CAR); to agonize activity of engineered cells that contains or expresses a recombinant receptor (e.g. CAR) having a extracellular domain containing the target antibody and an intracellular signaling domain; or to antagonize or block binding of a target antibody, e.g. present in a recombinant receptor expressed by an engineered cell, to its target antigen.

In some embodiments, provided are uses and methods of use thereof, and compositions and articles of manufacture including such anti-idiotype antibodies or antigen-binding fragments thereof, including for specifically detecting, identifying, or selecting, engineered cells expressing or including the target antibodies or fragments as part of a recombinant receptor (e.g. CAR) expressed by or on the engineered cells, such as anti-GPRC5D CAR T cells. In some embodiments, provided anti-idiotype antibodies or antigen-binding fragments thereof can be used for specific identification and/or selection of various anti-GPRC5D CARs, such as CARs bound to or expressed on a cell surface.

In some embodiments, provided are uses and methods of use thereof, and compositions and articles of manufacture including such anti-idiotype antibodies or antigen-binding fragments thereof, for agonizing, stimulating or activating engineered cells that contains or expresses a recombinant receptor (e.g. CAR) having a extracellular domain containing the anti-GPRC5D target antibody and an intracellular signaling domain. In such embodiments, among provided anti-idiotype antibodies and antigen-binding fragments thereof are anti-idiotype antibodies and antigen-binding fragments in which binding to the target antibody or fragment contained as part of the extracellular domain of a recombinant receptor (e.g. a CAR) expressed by or on the engineered cell results in agonist activity to stimulate or activate the engineered cell. In some embodiments, binding to the target antibody composed in the recombinant receptor activates the signaling domain of the recombinant receptor to initiate or mediate downstream signaling events leading to activation of transcription factors or other signaling molecules in the cell, proliferation of the engineered cell, production of cytokines, cytotoxic activity or other effector activities. In some embodiments, provided antibodies can be used to specifically stimulate or activate cells expressing target CARs, such as CAR T cells.

In some aspects, the provided anti-idiotype antibodies offer advantages compared to conventional reagents for detecting, identifying, manipulating and/or affecting and/or engineering cells that express a CAR, and in particular a CAR containing an anti-GPRC5D antibody scFv extracellular domain or one containing the recognized idiotype. In certain available methods detection of the presence or absence or amount of CAR or CAR-expressing cells (and/or stimulation or manipulation of the CAR), in a sample, is carried out by assessing the presence or absence or amount of a surrogate molecule, such as one included in the construct encoding the CAR and thus serving as an indirect or surrogate marker for its expression. In certain available methods, detection is carried out using a generic antibody reagent and/or a reagent that is not specific for the particular CAR assessed, e.g., as compared to other CARs that may have similar or identical domains other than the antigen-binding region; for example, such antibodies may include anti-species antibodies recognizing spacer or other domains from the species from which a CAR domain was derived, and/or antibodies recognizing particular components used in spacer regions of the target and also other chimeric receptors. In certain available methods designed to detect the presence or absence of CARs, detection is carried out using an agent recognizing a CAR constant region. In some cases, reagents against a surrogate molecule or marker also may not be suitable for specifically stimulating or inducing activation of engineered cells (e.g. CAR-T cells), either because the surrogate marker or molecule does not contain a signaling domain or because the signaling domain mediates signaling via a different signaling pathway from the CAR. In certain available methods, CAR cells are stimulated through the use of general reagents, such as anti-CD3/CD28 recognizing agents. Certain methods use a recombinant ligand of the CAR (e.g., GPRC5D-Fc). Such methods in certain contexts may not be entirely satisfactory and/or have certain limitations. In some cases, CAR ligands, such as GPRC5D, may not always be entirely effective, e.g., for use in complex flow cytometry panels or if agonist-mediated stimulation is desired using soluble reagents. In some cases, CAR ligands, such as GPRC5D or GPRC5D-Fc, may not always be entirely effective, for example, because the affinity of the ligand for the CAR or its format or structure may not be optimal for certain uses. e.g., for use in complex flow cytometry panels or if agonist-mediated stimulation is desired using soluble reagents. Improved methods and agents are needed, including those providing improved sensitivity and/or selectivity. Provided herein are embodiments meeting such needs.

The provided anti-idiotype antibodies and antigen-binding fragments thereof in some embodiments overcome one or more of these challenges, including challenges related to low binding affinity associated with target antibody ligands and/or non-specific binding associated with antibody reagents directed to target antibody constant regions. The provided anti-idiotype antibodies include antibodies that provide a reagent with both high affinity and specificity for its target antibody or antigen binding fragment thereof. In some embodiments, the provided antibodies exhibit greater specificity and binding affinity for their target antibodies or antigen-binding fragments thereof, such as the provided anti-GPRC5D antibody, or an antigen-binding fragment thereof, compared to GPRC5D-Fc and other reagents currently available for detecting or identifying the CAR.

In some embodiments, provided methods and uses include in vitro or ex vivo methods and uses, including those for detecting or quantifying expression on engineered cells of a recombinant receptor (e.g. CAR) containing the anti-GPRC5D target antibody as part of its extracellular antigen-binding domain, or for assessing or monitoring a functional activity of engineered cells expressing a recombinant receptor (e.g. a CAR). In some embodiments, provided methods and uses include in vivo methods and uses, involving administering the anti-idiotype antibody to a subject that has been or is to be administered engineered cells expressing a recombinant receptor (e.g. CAR) in which the anti-GPRC5D target antibody is composed in the extracellular domain, including in methods for detecting such engineered cells in the subject; for stimulating or activating such engineered cells in vivo in the subject; or in some cases, for ablating or killing the engineered cells in vivo in the subject. Furthermore, in certain embodiments, among anti-idiotype antibodies and antigen-binding fragments thereof provided herein are those selected as agonists or antagonists of chimeric receptors comprising their target antibodies or antigen-binding fragments thereof, allowing for selective detection, isolation, ablation and/or depletion (for example, killing via antibody-dependent cell-mediated cytotoxicity, ADCC), and/or stimulation or activation of cells with such chimeric receptors bound to or expressed on their surface. Provided herein are anti-idiotype antibody agonists that exhibit activity to stimulate, such as activate, a CAR containing an extracellular binding domain derived from a provided anti-GPRC5D antibody, or antigen-binding fragment thereof. In some aspects, such antibodies can be used in methods of stimulating and expanding specific CAR-expressing cells, including in processes for generating and preparing the CAR-expressing cells.

In certain embodiments, among provided anti-idiotype antibodies and antigen-binding fragments thereof provided herein are those selected as agonists of a recombinant receptor, such as CAR, containing the anti-GPRC5D target antibody or antigen-binding fragment thereof in its extracellular domain, allowing for selective stimulation or activation of cells with such recombinant receptors (e.g. CARs) bound to or expressed on their surface. In some embodiments, provided herein are anti-idiotype antibodies that are agonists that exhibit activity to stimulate, such as activate, a CAR containing an extracellular binding domain derived from the anti-GPRC5D antibody or antigen-binding fragment thereof. In some aspects, such antibodies can be used in methods of specifically stimulating or activating CAR-expressing cells. In particular embodiments, the recombinant receptor (e.g. CAR) contains a signaling domain that, when engaged by an agonist anti-idiotype antibody or antigen-binding fragment, is able to induce or activate one or more downstream signaling cascades in the engineered cells resulting in increased activation of transcription factors, alteration of expression of effector genes or activation or inhibition of target protein, phosphorylation or dephosphorylation events in the cells, or one or more effector functions. For example, among provided recombinant receptors containing a target anti-GPRC5D antibody are anti-GPRC5D CARs that contain an intracellular domain with a CD3zeta signaling domain and, in some cases, a costimulatory signaling domain (e.g. 4-1BB signaling domain). In some embodiments, binding of a provided agonist anti-idiotype antibody or antigen-binding fragment to the CAR expressed on T cells results in one or more of NF-κB activation, upregulation of Nur77 expression, induction of inflammatory cytokine production (e.g. IFN-gamma, TNF-alpha), T cell proliferation, and/or cytotoxic activity. For example, as shown in examples herein certain anti-idiotype antibodies or antigen binding fragments exhibit agonist activity to stimulate or activate CAR-T cells containing the target anti-GPRC5D antigen-binding domain, including the ability to induce Nur77 expression (e.g. based on reporter expression in a reporter assay), proliferation and/or production of cytokines. In some embodiments, the methods of stimulation or activation is recombinant receptor (e.g. CAR)-dependent or -specific. In some embodiments, the methods of stimulating or activating the recombinant receptor (e.g. CAR)-engineered cells can be carried out in vitro or ex vivo, such as in methods of specifically stimulating and expanding CAR-expressing cells, including in processes for generating and preparing the CAR-expressing cells. In some embodiments, the methods of stimulation or activation can be carried out in vivo in a subject that has previously received administration of the recombinant receptor (e.g. CAR)-engineered cells, such as to reinvigorate or induce expansion of the engineered cells in vivo in a subject, e.g. at a time at or after the peak number of engineered cells is observed or detected in the subject.

In certain embodiments, among provided anti-idiotype antibodies or antigen-binding fragments thereof provided herein are those that can be used in methods to induce or ablate killing of cells in a subject. In particular aspects of such embodiments, the anti-idiotype antibody is one that contains an Fc region, e.g. is an intact of full-length antibody. In general, the Fc region is responsible for effector functions via binding of Fc to an activating Fc receptor (e.g. FcγRIII), such as expressed on NK cells, which can mediate antibody-dependent cell cytotoxicity (ADCC). In some embodiments, binding to the target antibody of the recombinant receptor (e.g. CAR) expressed on the engineered cells by provided anti-idiotype antibody results in ablation and/or depletion of engineered cells in vivo, for example, by killing via antibody-dependent cell-mediated cytotoxicity, ADCC). In some embodiments, such methods or uses can be carried out in vivo following administration of the anti-idiotype antibody or antigen-binding fragment to a subject, such as at a time after the subject has received administration of the engineered cells. In some embodiments, a provided anti-idiotype antibody may be administered to a subject at a time when activity of the engineered cells (e.g. CAR T-cells) are no longer desired in the subject, for example, if the subject exhibits one or more signs or symptoms of severe toxicity that cannot be otherwise resolved by an anti-inflammatory agent or steroid.

Also provided herein are nucleic acids encoding the provided anti-idiotype antibodies and fragments, and cells, such as recombinant cells, expressing and for production of these anti-idiotype antibodies and fragments. Also provided are methods of making and using the anti-idiotype antibodies and fragments, as well as cells expressing or containing the anti-idiotype antibodies and fragments.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. ANTI-IDIOTYPE ANTIBODIES

Provided in some aspects are binding molecules, such as anti-idiotype antibodies or antigen-binding fragments thereof ("anti-IDs") that bind to or recognize a target anti-GPRC5D antibody moiety.

In some embodiments, provided are anti-idiotype antibodies that bind to or recognize a target anti-GPRC5D antibody that comprises a heavy chain variable (VH) region comprising the amino acid sequence set forth in SEQ ID NO: 7, and a light chain variable (VL) region comprising the amino acid sequence set forth in SEQ ID NO: 8. In some embodiments, provided are anti-idiotype antibodies that bind to or recognize a target anti-GPRC5D antibody that comprises a heavy chain complementarity determining region 1 (CDR-H1) having the amino acid sequence set forth in SEQ ID NO: 1, a CDR-H2 having the amino acid sequence set forth in SEQ ID NO: 2, and a CDR-H3 having the amino acid sequence set forth in SEQ ID NO: 3; and a light chain complementarity determining region 1 (CDR-L1) having the amino acid sequence set forth in SEQ ID NO: 4, a CDR-L2 having the amino acid sequence set forth in SEQ ID NO: 5, and a CDR-L3 having the amino acid sequence set forth in SEQ ID NO: 6. In some embodiments, provided are anti-idiotype antibodies that bind to or recognize a target anti-GPRC5D antibody that is a single chain fragment where the VL region and the VH region of the single chain fragment is joined by a flexible linker comprising the amino acid sequence set forth in SEQ ID NO: 10. In some embodiments, provided are anti-idiotype antibodies that bind to or recognize a target anti-GPRC5D antibody that is a single chain variable fragment (scFv) comprising the amino acid sequence set forth in SEQ ID NO: 9.

In some embodiments, the provided anti-idiotype antibodies include antibodies or antigen-binding fragments thereof that bind to or recognize a variable domain (Fv), such as a single chain Fv (scFv), derived from the target anti-GPRC5D antibody. In some embodiments, the anti-idiotype antibodies bind to or recognize a particular epitope or region of an Fv, generally an epitope or region comprising one or more complementarity determining regions. In some embodiments, the anti-idiotype antibodies bind to or recognize an epitope or region overlapping an Fv paratope.

In some embodiments, the provided anti-idiotype antibodies include antibodies or antigen-binding fragments thereof that specifically bind to a variable domain (Fv), such as a single chain Fv (scFv), derived from the target anti-GPRC5D antibody.

In some embodiments, the provided anti-idiotype antibodies include those that bind to or recognize an anti-GPRC5D moiety that is contained as part of the extracellular domain of a target chimeric antigen receptor (CAR). In some embodiments, the target CAR contains an antigen-binding portion that contains the target antibody molecule or antigen-binding fragment or portion of the target antibody. In some embodiments, the target CAR includes an antigen-binding domain that is an scFv derived from the VH and VL chains of the target antibody. In some embodiments, there is provided an anti-idiotype antibody that binds to or recognizes an anti-GPRC5D CAR that contains an scFv derived from the target antibody. Exemplary features of CARs are described further below.

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The term "anti-idiotype antibody" refers to an antibody, including antigen-binding fragments thereof, that recognizes, is targeted to, and/or binds to an idiotope of an antibody, such as an antigen-binding fragment. The idiotopes of an antibody may include, but are not necessarily limited to, residues within one or more of complementarity determining region(s) (CDRs) of the antibody, variable regions of the antibody, and/or partial portions or portions of such variable regions and/or of such CDRs, and/or any combination of the foregoing. The CDR may be one or more selected from the group consisting of CDR-H1, CDR-H2, CDR-H3, CDR-L1, CDR-L2, and CDR-L3. The variable regions of the antibody may be heavy chain variable regions, light chain variable regions, or a combination of the heavy chain variable regions and the light chain variable regions. The partial fragments or portions of the heavy chain variable regions and/or the light chain variable regions of the antibody may be fragments including 2 or more, 5 or more, or 10 or more contiguous amino acids, for example, from about 2 to about 100, from about 5 to about 100, from about 10 to about 100, from about 2 to about 50, from about 5 to about 50, or from about 10 to about 50 contiguous amino acids within the heavy chain variable regions or the light chain variable regions of the antibody; the idiotope may include multiple non-contiguous stretches of amino acids. The partial fragments of the heavy chain variable regions and the light chain variable regions of the antibody may be fragments including 2 or more, 5 or more, or 10 or more contiguous amino acids, for example, from about 2 to about 100, from about 5 to about 100, from about 10 to about 100, from about 2 to about 50, from about 5 to about 50, or from about 10 to about 50 contiguous amino acids within the variable regions, and in some embodiments contain one or more CDRs or CDR fragments. The CDR fragments may be consecutive or non-consecutive 2 or more, or 5 or more amino acids within the CDR. Therefore, the idiotopes of the antibody may be from about 2 to about 100, from about 5 to about 100, from about 10 to about 100, from about 2 to about 50, from about 5 to about 50, or from about 10 to about 50 contiguous amino acids containing one or more CDR or one or more CDR fragments within the heavy chain variable regions or the light chain variable regions of the antibody. In another embodiment, the idiotopes may be a single amino acid which is located at the variable regions of the antibody, for example, CDR sites.

In some embodiments, the idiotope is any single antigenic determinant or epitope within the variable portion of an antibody. In some cases, it can overlap the actual antigen-binding site of the antibody, and in other cases, it may comprise variable region sequences outside of the antigen-binding site of the antibody. The set of individual idiotopes of an antibody is in some embodiments referred to as the "idiotype" of such antibody.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745." ("Contact" numbering scheme), Lefranc M P et al., "IMGT unique numbering for immunoglobulin and T cell receptor variable domains and Ig superfamily V-like domains," Dev Comp Immunol, 2003 January; 27(1): 55-77 ("IMGT" numbering scheme), and Honegger A and Plückthun A, "Yet another numbering scheme for immunoglobulin variable domains: an automatic modeling and analysis tool," J Mol Biol, 2001 Jun. 8; 309(3): 657-70, ("Aho" numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table 1, below, lists exemplary position boundaries of CDR-L1, CDR-L2, CDR-L3 and CDR-H1, CDR-H2, CDR-H3 as identified by Kabat, Chothia, and Contact schemes, respectively. For CDR-H1, residue numbering is listed using both the Kabat and Chothia numbering schemes. FRs are located between CDRs, for example, with FR-L1 located between CDR-L1 and CDR-L2, and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

| CDR | Kabat | Chothia | Contact |
|---|---|---|---|
| CDR-L1 | L24--L34 | L24--L34 | L30--L36 |
| CDR-L2 | L50--L56 | L50--L56 | L46--L55 |
| CDR-L3 | L89--L97 | L89--L97 | L89--L96 |
| CDR-H1 (Kabat Numbering[1]) | H31--H35B | H26--H32...34 | H30--H35B |
| CDR-H1 (Chothia Numbering[2]) | H31--H35 | H26--H32 | H30--H35 |
| CDR-H2 | H50--H65 | H52--H56 | H47--H58 |
| CDR-H3 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273,927-948

Thus, unless otherwise specified, a "CDR" or "complementary determining region," or individual specified CDRs (e.g., "CDR-H1, CDR-H2), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given $V_H$ or $V_L$ amino acid sequence, it is understood that such a CDR has a sequence of the corresponding CDR (e.g., CDR-H3) within the variable region, as defined by any of the aforementioned schemes. In some embodiments, specified CDR sequences are specified.

Likewise, unless otherwise specified, a FR or individual specified FR(s) (e.g., FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, or Contact method. In other cases, the particular amino acid sequence of a CDR or FR is given.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352: 624-628 (1991).

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all framework regions (FRs) amino acid residues are derived from human FRs. In some embodiments, the humanized forms of a non-human antibody, e.g., a murine antibody, are chimeric antibodies that contain minimal sequences derived from non-human immunoglobulin. In certain embodiments, the humanized antibodies are antibodies from non-human species having one or more complementarily determining regions (CDRs) from the non-human species and a framework region (FR) from a human immunoglobulin molecule. In some embodiments, a humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity. (See, e.g., Queen, U.S. Pat. No. 5,585,089 and Winter, U.S. Pat. No. 5,225,539.) Such chimeric and humanized monoclonal antibodies can be produced by recombinant DNA techniques known in the art.

In certain embodiments, a humanized antibody is a human immunoglobulin (recipient antibody) in which residues from a heavy chain variable region of the recipient are replaced by residues from a heavy chain variable region of a non-human species (donor antibody) such as mouse, rat, rabbit, or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. In some embodiments, a nucleic acid sequences encoding human variable heavy chains and variable light chains are altered to replace one or more CDR sequences of the human (acceptor) sequence by sequence encoding the respective CDR in the nonhuman antibody sequence (donor sequence). In some embodiments, the human acceptor sequence may comprise FR derived from different genes. In particular embodiments, a humanized antibody will contain substantially all of at least one, and typically two, variable domains, in which all or substantially all of the hypervariable loops correspond to those of a non-human immunoglobulin, and all or substantially all of the FRs are those of a human immunoglobulin sequence. In some embodiments, the humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982, 321 and 7,087,409, incorporated by reference herein. In some embodiments, provided herein are humanized anti-idiotype antibodies.

In particular embodiments, an antibody, e.g., an anti-idiotype antibody, is humanized. In certain embodiments, the antibody is humanized by any suitable known means. For example, in some embodiments, a humanized antibody can have one or more amino acid residues introduced into it from a source which is non-human. These non-human amino acid residues are often referred to as "import" residues, which are typically taken from an "import" variable domain. In particular embodiments, humanization can be essentially performed by following the method of Winter and co-workers (Jones et al. (1986) Nature 321:522-525; Riechmann et al. (1988) Nature 332:323-327; Verhoeyen et al. (1988) Science 239:1534-1536), such as by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In certain embodiments, the humanized antibody is a human antibody in which some hypervariable region residues and possibly some FR residues are substituted by residues from analogous sites in rodent antibodies.

Sequences encoding full length antibodies can be subsequently obtained by joining the rendered variable heavy and variable light chain sequences to human constant heavy chain and constant light chain regions. Suitable human constant light chain sequences include kappa and lambda constant light chain sequences. Suitable human constant heavy chain sequences include IgG1, IgG2 and sequences encoding IgG1 mutants which have rendered immune-stimulating properties. Such mutants may have a reduced ability to activate complement and/or antibody dependent cellular cytotoxicity and are described in U.S. Pat. No. 5,624,821; WO 99/58572, U.S. Pat. No. 6,737,056. A suitable constant heavy chain also includes an IgG1 comprising the substitutions E233P, L234V, L235A, A327G, A330S, P331S and a deletion of residue 236. In another embodiment, the full length antibody comprises an IgA, IgD, IgE, IgM, IgY or IgW sequence.

Suitable human donor sequences can be determined by sequence comparison of the peptide sequences encoded by the mouse donor sequences to a group of human sequences, preferably to sequences encoded by human germ line immunoglobulin genes or mature antibody genes. A human sequence with a high sequence homology, preferably with the highest homology determined may serve as the acceptor sequence to for the humanization process.

In addition to the exchange of human CDRs for mouse CDRs, further manipulations in the human donor sequence may be carried out to obtain a sequence encoding a humanized antibody with optimized properties (such as affinity of the antigen).

Furthermore the altered human acceptor antibody variable domain sequences may also be rendered to encode one or more amino acids (according to the Kabat numbering system) of position 4, 35, 38, 43, 44, 46, 58, 62, 64, 65, 66, 67, 68, 69, 73, 85, 98 of the light variable region and 2, 4, 36, 39, 43, 45, 69, 70, 74, 75, 76, 78, 92 of the heavy variable region corresponding to the non-human donor sequence (Carter and Presta, U.S. Pat. No. 6,407,213).

In particular embodiments, it is generally desirable that antibodies be humanized with retention of high affinity for the antigen and other favorable biological properties. To achieve this goal, in some embodiments, the humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and imported sequences so that the desired antibody characteristic, such as increased affinity for the target antigen(s), is achieved. In general, the hypervariable region residues are directly and most substantially involved in influencing antigen binding.

In particular embodiments, choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies. See, e.g., Carter et al. (1992) Proc. Natl. Acad. Sci. USA, 89:4285; Presta et al. (1993) J. Immunol., 151:2623.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

A. Anti-ID Antibodies Against a Target Anti-GPRC5D Antibody

In some embodiments, provided are anti-idiotype antibodies that bind to or recognize a target anti-GPRC5D antibody or an antigen-binding fragment thereof, as described above. In some embodiments, provided are anti-idiotype antibodies that specifically bind to a target anti-GPRC5D antibody, or an antigen-binding fragment thereof, as described above. Exemplary antibodies or antigen-binding fragments thereof are provided below.

In some embodiments, the provided anti-idiotype antibodies binds to or recognizes an antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 7, and a VL region having at least 90%, 91%, 92%, 93%, 94%, 95%, 96%, 97%, 98%, or 99% sequence identity to the amino acid sequence set forth in SEQ ID NO: 8. In some embodiments, the provided anti-idiotype antibodies binds to or recognizes an antibody or antigen-binding fragment thereof that includes a VH region having the amino acid sequence set forth in SEQ ID NO: 7, and a VL region having the amino acid sequence set forth in SEQ ID NO: 8.

In some embodiments, the provided anti-idiotype antibodies binds to or recognizes a target anti-GPRC5D antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 7, and a VL region having at least 90%, 91%, 92%, 93%, 94%, 95%, 96%, 97%, 98%, or 99% sequence identity to the amino acid sequence set forth in SEQ ID NO: 8. In some embodiments, the provided anti-idiotype antibodies binds to or recognizes a target anti-GPRC5D antibody or antigen-binding fragment thereof that includes a VH region having the amino acid sequence set forth in SEQ ID NO: 7, and a VL region having the amino acid sequence set forth in SEQ ID NO: 8.

In some embodiments, the provided anti-idiotype antibodies binds to or recognizes an scFv that includes an amino acid sequence having at least 90%, 91%, 92%, 93%, 94%, 95%, 96%, 97%, 98%, or 99% sequence identity to the amino acid sequence set forth in SEQ ID NO: 9. In some embodiments, the provided anti-idiotype antibodies binds to or recognizes an scFv having the amino acid sequence set forth in SEQ ID NO: 9.

In some embodiments, the provided anti-idiotype antibodies binds to or recognizes a target anti-GPRC5D antibody that is an scFv that includes an amino acid sequence having at least 90%, 91%, 92%, 93%, 94%, 95%, 96%, 97%, 98%, or 99% sequence identity to the amino acid sequence set forth in SEQ ID NO: 9. In some embodiments, the provided anti-idiotype antibodies binds to or recognizes an scFv having the amino acid sequence set forth in SEQ ID NO: 9.

In some embodiments, the provided anti-idiotype antibodies binds to or recognizes an antibody or antigen-binding fragment thereof that includes a CDR-H1 having the amino acid sequence set forth in SEQ ID NO: 1, a CDR-H2 having the amino acid sequence set forth in SEQ ID NO: 2, and a CDR-H3 having the amino acid sequence set forth in SEQ ID NO: 3; and a CDR-L1 having the amino acid sequence set forth in SEQ ID NO: 4, a CDR-L2 having the amino acid sequence set forth in SEQ ID NO: 5, and a CDR-L3 having the amino acid sequence set forth in SEQ ID NO: 6.

In some embodiments, the provided anti-idiotype antibodies binds to or recognizes a target anti-GPRC5D antibody or antigen-binding fragment thereof that includes a CDR-H1 having the amino acid sequence set forth in SEQ ID NO: 1, a CDR-H2 having the amino acid sequence set forth in SEQ ID NO: 2, and a CDR-H3 having the amino acid sequence set forth in SEQ ID NO: 3; and a CDR-L1 having the amino acid sequence set forth in SEQ ID NO: 4, a CDR-L2 having the amino acid sequence set forth in SEQ ID NO: 5, and a CDR-L3 having the amino acid sequence set forth in SEQ ID NO: 6.

In some embodiments, the provided anti-idiotype antibodies binds to or recognizes an antibody or antigen-binding fragment thereof that has the same idiotype as a target anti-GPRC5D antibody comprising a VH region having the amino acid sequence set forth in SEQ ID NO: 7, and a VL region having the amino acid sequence set forth in SEQ ID NO: 8.

In some embodiments, the provided anti-idiotype antibodies competes for binding to a target anti-GPRC5D antibody comprising a VH region having the amino acid sequence set forth in SEQ ID NO: 7, and a VL region having the amino acid sequence set forth in SEQ ID NO: 8, with an antibody or antigen-binding fragment thereof that includes a VH region comprising the amino acid sequence set forth in SEQ ID NO: 25 and a VL region comprising the amino acid sequence set forth in SEQ ID NO: 26.

In some embodiments, the provided anti-idiotype antibodies bind to or recognize an antibody or antigen-binding fragment thereof that competes for binding with a target anti-GPRC5D antibody comprising a VH region having the amino acid sequence set forth in SEQ ID NO: 7, and a VL region having the amino acid sequence set forth in SEQ ID NO: 8.

In some embodiments, the provided anti-idiotype antibodies compete for binding to an anti-GPRC5D target antibody or antigen-binding fragment thereof with a anti-GPRC5D antibody comprising a VH region having the amino acid sequence set forth in SEQ ID NO: 7, and a VL region having the amino acid sequence set forth in SEQ ID NO: 8.

In some embodiments, the provided anti-idiotype antibodies bind to or recognize the antigen-binding domain of the target anti-GPRC5D antibody that is contained within a CAR. In some embodiments, the provided anti-idiotype antibodies bind to or recognize the antigen-binding domain of the target anti-GPRC5D antibody as contained within a CAR. In some embodiments, the CAR is any as described in Section II.

In some embodiments, the provided anti-idiotype antibodies or antigen-binding fragments thereof include a VH region comprising at least 90% sequence identity to the VH region amino acid sequence set forth in SEQ ID NO: 25, such as at least 91%, 92%, 93%, 94%, 95%, 96%, 97%, 98%, or 99% sequence identity thereto; and a VL region comprising at least 90% sequence identity to the VL region amino acid sequence set forth in SEQ ID NO: 26, such as at least 91%, 92%, 93%, 94%, 95%, 96%, 97%, 98%, or 99% sequence identity thereto.

In some embodiments, the provided anti-idiotype antibodies or antigen-binding fragments thereof include a VH region comprising a CDR-H1 comprising the amino acid sequence set forth in SEQ ID NO: 15, a CDR-H2 comprising the amino acid sequence set forth in SEQ ID NO: 16, and a CDR-H3 comprising the amino acid sequence set forth in SEQ ID NO: 17; and a VL region comprising a CDR-L1 comprising the amino acid sequence set forth in SEQ ID NO: 22, a CDR-L2 comprising the amino acid sequence set forth in SEQ ID NO: 23, and a CDR-L3 comprising the amino acid sequence set forth in SEQ ID NO: 24. In some embodiments, the provided anti-idiotype antibodies or antigen-binding fragments thereof include a VH region comprising a CDR-H1 comprising the amino acid sequence set forth in SEQ ID NO: 18, a CDR-H2 comprising the amino acid sequence set forth in SEQ ID NO: 19, and a CDR-H3 comprising the amino acid sequence set forth in SEQ ID NO: 17; and a VL region comprising a CDR-L1 comprising the amino acid sequence set forth in SEQ ID NO: 22, a CDR-L2 comprising the amino acid sequence set forth in SEQ ID NO: 23, and a CDR-L3 comprising the amino acid sequence set forth in SEQ ID NO: 24. In some embodiments, the provided anti-idiotype antibodies or antigen-binding fragments thereof include a VH region comprising a CDR-H1 comprising the amino acid sequence set forth in SEQ ID NO: 20, a CDR-H2 comprising the amino acid sequence set forth in SEQ ID NO: 21, and a CDR-H3 comprising the amino acid sequence set forth in SEQ ID NO: 17; and a VL region comprising a CDR-L1 comprising the amino acid sequence set forth in SEQ ID NO: 22, a CDR-L2 comprising the amino acid sequence set forth in SEQ ID NO: 23, and a CDR-L3 comprising the amino acid sequence set forth in SEQ ID NO: 24.

In some embodiments, provided are anti-idiotype antibodies or antigen-binding fragments thereof that include a CDR-H1, a CDR-H2, and a CDR-H3, respectively, comprising the amino acid sequences of a CDR-H1, a CDR-H2, and a CDR-H3 contained within the VH region amino acid sequence set forth in SEQ ID NO: 25; and a CDR-L1, a CDR-L2, and a CDR-L3, respectively, comprising the amino acid sequences of a CDR-L1, a CDR-L2, and a CDR-L3 contained within the VL region amino acid sequence set forth in SEQ ID NO: 26.

In some of any such embodiments, the VH region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 25. In some embodiments, the VH region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 25. In some embodiments, the VH region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 25.

In some of any such embodiments, the VL region comprises a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 26. In some embodiments, the VL region comprises a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 26. In some embodiments, the VL region comprises a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 26.

In some of any such embodiments, the VH region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 25, and the VL region comprises a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 26. In some embodiments, the VH region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 25, and the VL region comprises a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 26. In some embodiments, the VH region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 25, and the VL region comprises a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 26.

In some of any such embodiments, the VH region has the sequence of amino acids set forth in SEQ ID NO: 25. In some of any such embodiments, the VL region has the sequence of amino acids set forth in SEQ ID NO: 26. In some of any such embodiments, the VH region has the sequence of amino acids set forth in SEQ ID NO: 25, and the VL region has the sequence of amino acids set forth in SEQ ID NO: 26.

In some embodiments, the anti-idiotype antibody that binds to or recognizes the anti-GPRC5D antibody, or an antigen-binding fragment thereof, is a single-chain antibody fragment, such as an scFv or diabody. In some embodiments, the single-chain antibody includes one or more linkers joining two antibody domains or regions, such as a variable heavy chain (VH) region and a variable light chain (VL) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

In some embodiments, the anti-idiotype antibody is an intact antibody or full-length antibody. In some embodiments, the anti-ID may contain at least a portion of an immunoglobulin constant region, such as one or more constant region domains. In some embodiments, the constant regions include a light chain constant region (CL) and/or a heavy chain constant region 1 (CH1). In some embodiments, the anti-ID includes a CH2 and/or CH3 domain, such as an Fc region. In some embodiments, the Fc region is an Fc region of a human IgG, such as IgG1 or IgG4.

In some embodiments, provided are anti-idiotype antibodies or antigen-binding fragments thereof that include a heavy chain constant region contained within the amino acid sequence set forth in SEQ ID NO: 27, and a light chain constant region contained within the amino acid sequence set forth in SEQ ID NO: 28. In some embodiments, provided are anti-idiotype antibodies or antigen-binding fragments thereof that include a heavy chain constant region having at least 90% sequence identity to the heavy chain constant region contained within the amino acid sequence set forth in SEQ ID NO: 27, and a light chain constant region having at least 90% sequence identity to the light chain constant region contained within the amino acid sequence set forth in SEQ ID NO: 28.

In some embodiments, provided are anti-idiotype antibodies or antigen-binding fragments thereof that include a heavy chain comprising an amino acid sequence having at least 90% sequence identity to the amino acid sequence set forth in SEQ ID NO: 27, and a light chain comprising an amino acid sequence having at least 90% sequence identity to the amino acid sequence set forth in SEQ ID NO: 28.

In some embodiments, provided are anti-idiotype antibodies or antigen-binding fragments thereof that include a heavy chain comprising the amino acid sequence set forth in SEQ ID NO: 27, and a light chain comprising the amino acid sequence set forth in SEQ ID NO: 28.

In some embodiments, the anti-idiotype antibody is an antigen-binding fragment. In some embodiments, the antigen-binding fragment is selected from the group consisting of fragment antigen binding (Fab) fragments, F(ab')2 fragments, Fab' fragments, Fv fragments, a single chain variable fragment (scFv) or a single domain antibody.

Accordingly, provided are single-chain antibody fragments, such as scFvs and diabodies, particularly human single-chain fragments, typically comprising linker(s) joining two anti-idiotype antibody domains or regions, such VH and VL domains. The linker typically is a peptide linker, e.g., a flexible and/or soluble peptide linker, such as one rich in glycine and serine.

In some aspects, the linkers rich in glycine and serine (and/or threonine) include at least 80, 85, 90, 91, 92, 93, 94, 95, 96, 97, 98, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length.

In some embodiments, the anti-idiotype antibodies include isolated antibodies. In some embodiments, the anti-ID is humanized, recombinant, and/or monoclonal. In some embodiments, the anti-ID is human.

In some embodiments, the anti-idiotype antibody that binds to or recognizes the target anti-GPRC5D antibody is humanized. In particular embodiments, all or substantially all CDR amino acid residues of the humanized anti-idiotype antibody that binds to or recognizes the target anti-GPRC5D antibody are derived from target anti-GPRC5D antibody non-human CDRs. In some embodiments, the humanized anti-idiotype antibody that binds to or recognizes the target anti-GPRC5D antibody includes at least a portion of an antibody constant region derived from a human antibody.

In certain embodiments, the humanized anti-idiotype antibody that binds to or recognizes the target anti-GPRC5D antibody includes a human immunoglobulin (recipient antibody) in which residues from the heavy chain variable region of the recipient are replaced by residues from a heavy chain variable region of the nonhuman anti-idiotype antibody that binds to or recognizes the target anti-GPRC5D antibody. In some instances, FR residues of the human immunoglobulin are replaced by corresponding non-human residues. In some embodiments, the humanized antibody contains FR derived from different genes. In some embodiments, the humanized anti-idiotype antibody that binds to or recognizes the target anti-GPRC5D antibody contains at least a portion of an immunoglobulin constant region (Fc), typically that of a human immunoglobulin.

In some embodiments, the humanized anti-idiotype antibody that binds to or recognizes the target anti-GPRC5D antibody contains an altered human acceptor antibody variable domain sequences that have been rendered to encode one or more amino acid residues of position 4, 35, 38, 43, 44, 46, 58, 62, 64, 65, 66, 67, 68, 69, 73, 85, 98 (Kabat) of the light variable region and 2, 4, 36, 39, 43, 45, 69, 70, 74, 75, 76, 78, 92 (Kabat) of the heavy variable region corresponding to the non-human donor sequence.

In certain embodiments, the anti-idiotype antibody that binds to or recognizes the target anti-GPRC5D antibody is humanized. In particular embodiments, the humanized anti-idiotype antibody that binds to or recognizes the target anti-GPRC5D antibody contains one or more of a CDR-L1, CDR-L2, CDR-L3 and CDR-H1, CDR-H2, CDR-H3 region of a non-human anti-idiotype antibody that is that binds to or recognizes the target anti-GPRC5D antibody. In some embodiments, some or all of the CDR-L1, CDR-L2, CDR-L3 and CDR-H1, CDR-H2, CDR-H3 region of contain one or more amino acid modifications. In some embodiments, the modifications replacing a nonhuman amino acid residue with a human residue. In particular embodiments, the one or more of the CDR-L1, CDR-L2, CDR-L3 and CDR-H1, CDR-H2, CDR-H3 are inserted into the FR regions of a human antibody. In particular embodiments, the CDR-L1, CDR-L2, CDR-L3 and CDR-H1, CDR-H2, CDR-H3 of the nonhuman anti-idiotype antibody are the CDRs of the VH and VL regions having amino acid sequences set forth in SEQ ID NOs: 25 and 26, respectively. In some embodiments, all of the CDR-L1, CDR-L2, CDR-L3 and CDR-H1, CDR-H2, CDR-H3 of the anti-idiotype antibody that binds to or recognizes the target anti-GPRC5D antibody are inserted into the FRs of the human antibody. In particular embodiments, the CDR and FR regions are the regions as identified by Kabat, Chothia, AbM, and/or and Contact schemes.

In particular embodiments, one or more or all of the CDR-L1, CDR-L2, CDR-L3 and CDR-H1, CDR-H2, CDR-H3 of the nonhuman anti-idiotype antibody that binds to or recognizes the target anti-GPRC5D antibody are inserted into framework regions of a human antibody. In certain embodiments, the human antibody is an IgA, IgD, IgE, IgG, and IgM antibody. In particular embodiments, the human antibody is one of a subclass of human IgA, IgD, IgE, IgG, and IgM, e.g., human $IgG_1$, $IgG_2$, $IgG_3$, $IgG_4$, $IgA_1$, or $IgA_2$. In some embodiments, one or more or all of the CDR-L1, CDR-L2, CDR-L3 and CDR-H1, CDR-H2, CDR-H3 of the nonhuman anti-idiotype antibody that binds to or recognizes the target anti-GPRC5D antibody are inserted into framework regions of an antigen binding region that is from and/or is derived from a human antibody. In certain embodiments, the antigen binding fragment is from and/or is derived from a human IgA, IgD, IgE, IgG, and IgM antibody. The subunit structures and three-dimensional configurations of different classes of human immunoglobulins are well known and described generally in, for example, Abbas et al. Cellular and Mol. Immunology, 4th ed. (W.B. Saunders, Co., 2000). In some embodiments, the human antibody or antigen binding fragment thereof may be part of a larger fusion molecule, formed by covalent or non-covalent association of the human antibody with one or more other proteins or peptides.

In some embodiments, one or more or all of the CDR-L1, CDR-L2, CDR-L3 and CDR-H1, CDR-H2, CDR-H3 of the nonhuman anti-idiotype antibody that binds to or recognizes the target anti-GPRC5D antibody are inserted into framework regions of a human antibody or antigen-binding fragment thereof having all or a portion of an Fc region. In certain embodiments, the humanized anti-idiotype antibody that binds to or recognizes the target anti-GPRC5D antibody contains all or a portion of an Fc region. In some embodiments, the Fc region has one or more modifications, such as an amino acid modification (e.g. a substitution, insertion, or deletion) at one or more amino acid positions. Such modifications can be made, for example, to improve half-life, alter binding to one or more types of Fc receptors, and/or alter effector functions. In some embodiments, modified Fc regions have altered (e.g., decreased) binding to FcαRs, relative to that of an unmodified Fc region. In certain embodiments, the humanized anti-idiotype antibody contains all or a portion of a modified Fc region having an altered (e.g., decreased) binding to Fc receptor relative to that of an unmodified Fc region. Non-limiting examples of Fc modifications that alter its binding to the Fc receptors are described, for example, in U.S. Pat. Nos. 7,217,797 and 7,732,570; and U.S. Application Nos. US 2010/0143254 and 2010/0143254.

In certain embodiments, the binding affinity (EC50) and/or the dissociation constant of any of the provided anti-idiotype antibodies or antigen-binding fragments thereof that bind to or recognize the target anti-GPRC5D antibody or an antigen-binding fragment thereof, is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, or 1 nM, such as between at or about 1 nM and at or about 15 nM, e.g., between at or about 5 and at or about 10 nM. In certain embodiments, the EC50 of any of the provided anti-idiotype antibodies or antigen-binding fragments thereof that bind to or recognize the target anti-GPRC5D antibody or an antigen-binding fragment thereof, is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, or 1 nM, such as between at or about 1 nM and at or about 15 nM, e.g., between at or about 5 and at or about 10 nM. In certain embodiments, the dissociation constant of any of the provided anti-idiotype antibodies or antigen-binding fragments thereof that bind to or recognize the target anti-GPRC5D antibody or an antigen-binding fragment thereof, is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, or 1 nM, such as between at or about 1 nM and at or about 15 nM, e.g., between at or about 5 and at or about 10 nM. In certain embodiments, the extent of binding of any of the provided anti-idiotype antibodies or antigen-binding fragments thereof that bind to or recognize the target anti-GPRC5D antibody or an antigen-binding fragment thereof to a moiety unrelated to the target anti-GPRC5D moiety is less than, at, or about 10% of the binding of the antibody to the target anti-GPRC5D moiety as measured, e.g., by a radioimmunoassay (RIA). In some embodiments, any of the provided anti-idiotype antibodies or antigen-binding fragments thereof that bind to or recognize the target anti-GPRC5D antibody or an antigen-binding fragment thereof is an agonist of a CAR containing the antigen-binding domain of the target anti-GPRC5D antibody when immobilized on a support, such as a bead or a plate.

Also provided are nucleic acids encoding the provided anti-idiotype antibodies or antigen-binding fragments thereof that bind to or recognize the target anti-GPRC5D antibody or an antigen-binding fragment thereof. Among the provided nucleic acids are those encoding the anti-idiotype antibodies described herein. The nucleic acids may include those encompassing natural and/or non-naturally occurring nucleotides and bases, e.g., including those with backbone modifications. In some embodiments, the nucleic acid molecule(s) encoding anti-idiotype antibodies and/or portions, e.g., chains, thereof comprise a sequence of nucleotides that encode the VH region and comprises the sequence of nucleotides set forth in SEQ ID NO: 29, and a sequence of nucleotides that encode the VL region and comprises the sequence of nucleotides set forth in SEQ ID NO: 30. In some embodiments, the nucleic acid molecule(s) encoding anti-idiotype antibodies and/or portions, e.g., chains, thereof comprise a sequence of nucleotides that encode the heavy chain and comprises the sequence of nucleotides set forth in SEQ ID NO: 31, and a sequence of nucleotides that encode the light chain and comprises the sequence of nucleotides set forth in SEQ ID NO: 32.

Also provided are vectors containing the nucleic acids, host cells containing the vectors, e.g., for producing the antibodies. Also provided are methods for producing the antibodies. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, a method of making the anti-idiotype antibody is provided, wherein the method comprises culturing a host cell comprising a nucleic acid encoding the antibody, as provided above, under conditions suitable for expression of the antibody, and optionally recovering the antibody from the host cell (or host cell culture medium).

Exemplary nucleic acids and vectors include those having the sequences set forth in one or more of SEQ ID NOs: 29-32, and CDR-encoding portions thereof, as well as sequences containing at least at or about 90, 91, 92, 93, 94, 95, 96, 97, 98, or 99% identity thereto. The nucleic acid may encode an amino acid sequence comprising the $V_L$ and/or an amino acid sequence comprising the $V_H$ of the anti-idiotype antibody (e.g., the light and/or heavy chains of the antibody).

B. Exemplary Features

Anti-idiotype antibodies provided herein may be identified, screened for, or characterized for their physical/chemical properties and/or biological activities by various known assays. In one aspect, the anti-idiotype antibody is tested for its antigen binding activity, e.g., by known methods such as ELISA, Western blotting, and/or flow cytometric assays, including cell-based binding assays, for example, assessing binding of the anti-idiotype antibody (e.g., conjugated to a fluorescent marker or tagged) to a cell presenting the target anti-GPRC5D antibody moiety, in some cases compared to results using cells that do not express the target anti-GPRC5D antibody moiety. Binding affinity may be measured as Kd or EC50.

In some embodiments of any of the provided anti-idiotype antibodies, e.g. any of the provided antibodies in Section A above, the target anti-GPRC5D antibody moiety is a target anti-GPRC5D antibody as provided in Section A above.

In some embodiments, an anti-idiotype antibody or antigen binding fragment that binds or recognizes the target anti-GPRC5D moiety is one that specifically binds or preferentially binds (used interchangeably) the target anti-GPRC5D moiety. In some embodiments, an anti-idiotype antibody or antigen binding fragment that binds or recognizes the target anti-GPRC5D antibody is one that specifically binds or preferentially binds (used interchangeably) the target anti-GPRC5D antibody. In some embodiments, the anti-idiotype antibodies and antigen-binding fragments thereof that specifically bind to the target anti-GPRC5D antibody include antibodies having specific epitopic specificity. In some embodiments, an antibody that is said to specifically bind an antigen is when it preferentially recognizes its target antigen in a complex mixture of proteins and/or macromolecules. In some embodiments, an antibody is said to specifically bind or preferentially bind an antigen when the equilibrium dissociation constant is $<10^{-7}$ or $10^{-8}$ M. In some embodiments, the equilibrium dissociation constant may be $<10^{-9}$ M or $<10^{-10}$ M. In further embodiments, the equilibrium dissociation constant may be $<10^{-11}$ M or less. In some embodiments, an antibody specifically binds or preferentially binds to a target if it binds with greater affinity, avidity, more readily, and/or with greater duration than it binds to other substances. For instance, an anti-idiotype antibody or antigen-binding fragment specifically or preferentially binds a target anti-GPRC5D antibody if it reacts or associates more frequently, more rapidly, with greater duration and/or with greater affinity with the target anti-GPRC5D antibody, e.g. contained in a CAR, than it does with a non-target antibody, e.g. contained in a CAR. It is understood that specific binding or preferential binding does not necessarily require (although it can include) exclusive binding. Methods to determine such specific or preferential binding include immunoassays and other binding assays.

A variety of assays are known for assessing binding affinity and/or determining whether an antibody specifically binds to a particular binding partner. It is within the level of a skilled artisan to determine the binding affinity of an antibody, such as by using any of a number of binding assays that are well known in the art. Various binding assays are known and include, but are not limited to, for example, ELISA $K_D$, KinExA, flow cytometry, and/or surface plasmon resonance devices), including those described herein. Such methods include, but are not limited to, methods involving BIAcore®, Octet®, or flow cytometry. For example, in some embodiments, a BIAcore® instrument can be used to determine the binding kinetics and constants of a complex between two proteins using surface plasmon resonance (SPR) analysis (see, e.g, Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent). SPR measures changes in the concentration of molecules at a sensor surface as molecules bind to or dissociate from the surface. The change in the SPR signal is directly proportional to the change in mass concentration close to the surface, thereby allowing measurement of binding kinetics between two molecules. The dissociation constant for the complex can be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy, flow cytometry, sequencing and other methods for detection of binding of proteins.

In particular embodiments, the antibodies and antigen-binding fragments thereof disclosed herein preferentially bind to the target anti-GPRC5D antibody compared to a non-target antibody, such that the binding affinity of the antibodies for the target anti-GPRC5D antibody is at least 5 fold, at least 10 fold, at least 100 fold, or at least 1000 fold greater than the binding affinity of the antibodies for non-target antibodies. The non-target antibody includes antibodies against different antigens (e.g. other than GPRC5D), or can include antibodies against GPRC5D that contain one or more different CDRs than the target anti-GPRC5D antibody or bind to a different epitope or binding site of GPRC5D.

In some embodiments, the anti-idiotype antibody specifically binds with minimal cross-reactivity to other antibodies. In some embodiments, the anti-idiotype antibody does not cross-react with an antibody moiety against a different antigen from the target anti-GPRC5D antibody moiety. In some embodiments, the anti-idiotype antibody does not cross-react with an anti-GPRC5D antibody moiety different from the target anti-GPRC5D antibody moiety.

In some embodiments, the anti-idiotype antibody does cross-react with an anti-GPRC5D antibody moiety different from the target anti-GPRC5D antibody moiety.

In some embodiments, the anti-idiotype antibody binds to or recognizes a target anti-GPRC5D antibody moiety that is part of a fusion protein, such as a recombinant receptor. In some embodiments, the anti-idiotype antibody does not bind to any epitope in the fusion protein outside of the target anti-GPRC5D antibody moiety. For example, in some embodiments, the target anti-GPRC5D antibody moiety is, or is part of, the antigen-binding domain of a chimeric antigen receptor (CAR), and the anti-idiotype antibody does not bind any epitope outside of the antigen-binding domain. In some embodiments, the CAR antigen-binding domain comprises or consists of an scFv.

In some embodiments, the anti-idiotype antibody binds to or recognizes a target anti-GPRC5D antibody moiety that is an scFv contained in a CAR. In some embodiments, the anti-idiotype antibody binds to or recognizes an epitope overlapping one or more complementarity determining regions (CDRs) of the target anti-GPRC5D scFv. In some embodiments, the anti-idiotype antibody does not bind any epitopes in the CAR outside of the scFv; in some embodiments, it does not bind to a reference antibody. In some embodiments, the reference antibody binds to or recognizes the same antigen as the target antibody, e.g., to the GPRC5D and/or comprises one or more variable heavy and/or variable light framework region(s) having at least 90, 95, 96, 97, 98, or 99% identity to the corresponding framework region(s) of the target antibody (in some aspects, the one or more framework regions comprise an FR1, FR2, FR3, and/or FR4 of the heavy and/or the light chain); and/or contains the same heavy and/or light chain v-gene (or v-gene usage) as the target antibody and/or is derived from the same v-gene sequence as the target antibody. In some aspects, the reference antibody is the target anti-GPRC5D antibody.

In some embodiments, the CAR comprising a target anti-GPRC5D antibody moiety that is an scFv comprises a spacer linking the scFv to its transmembrane domain, and the anti-idiotype antibody does not bind any epitope in the spacer. In some embodiments, the spacer is a sequence derived from CD28, such as an extracellular portion from CD28. In some embodiments, the spacer comprises the amino acid sequence of SEQ ID NO: 11. In some embodiments, the anti-idiotype antibody does not bind any epitope in an Fc domain, such as the Fc domain of IgG1. In some embodiments, the Fc domain is an IgG1 Fc domain lacking the hinge region.

In some embodiments, the anti-idiotype antibody binds to or recognizes a target anti-GPRC5D scFv (e.g., set forth in SEQ ID NO:9) contained in the extracellular antigen-binding domain of a target CAR.

In some embodiments, the anti-idiotype antibody does not cross-react with a different CAR. In some embodiments, the anti-idiotype antibody does not cross-react with a different anti-GPRC5D CAR. In some embodiments, the anti-idiotype antibody does not cross-react with an anti-GPRC5D antibody moiety, e.g., of a reference antibody, having one or more different idiotopes compared to the target anti-GPRC5D scFv. In some embodiments, the anti-idiotype antibody binds to or recognizes a target anti-GPRC5D scFv of a CAR derived from the target anti-GPRC5D antibody. In some embodiments, the target anti-GPRC5D antibody moiety is derived from a target anti-GPRC5D antibody comprising a VH region comprising the amino acid sequence of SEQ ID NO: 7, and a VL region comprising the amino acid sequence of SEQ ID NO: 8, and the anti-idiotype antibody does not cross-react with a CAR containing an anti-GPRC5D antibody moiety derived from a different anti-GPRC5D antibody.

In some embodiments, the anti-idiotype antibody is an agonist of the CAR. An anti-idiotype antibody or antigen-binding fragment thereof is said to be "an agonist" of a CAR containing in its extracellular antigen-binding domain a target anti-GPRC5D antibody or antigen-binding fragment thereof when binding of the anti-idiotype antibody or antigen-binding fragment thereof to the anti-GPRC5D target antibody increases an activity of cells (e.g. T cells) expressing the CAR, e.g., increased Nur77 expression, increased proliferation, increased cytokine production (e.g. IFN-gamma or TNFalpha), and/or increased cytotoxic activity, or other effector activity of the cells. For instance, in some embodiments, binding of the anti-idiotype antibody or antigen-binding fragment thereof to the anti-GPRC5D target antibody contained in the extracellular antigen-binding domain of the CAR is able to stimulate or activate the CAR to thereby induce or mediate one or more activities of cells expressing the CAR.

In some embodiments, the anti-idiotype antibody is an agonist of the CAR when in solution, such as when the anti-idiotype antibody is soluble or is not immobilized on a support, such as a bead or a plate. In some embodiments, any of the provided anti-idiotype antibodies or antigen-binding fragments thereof is an agonist of a CAR containing in its extracellular antigen-binding domain the target anti-GPRC5D antibody when the anti-idiotype antibody is in solution, such as when the anti-idiotype antibody is soluble or is not immobilized on a support, such as a bead or a plate. In some embodiments, any of the provided anti-idiotype antibodies or antigen-binding fragments thereof that bind to or recognize the target anti-GPRC5D antibody, or an antigen-binding fragment thereof, is an agonist of a CAR containing in its extracellular antigen-binding domain the target anti-GPRC5D antibody when the anti-idiotype antibody is in solution, such as when the anti-idiotype antibody is soluble or is not immobilized on a support, such as a bead or a plate.

In some embodiments, the anti-idiotype antibody is an agonist of the CAR. In some embodiments, the anti-idiotype antibody is an agonist of the CAR when immobilized on a support, such as a bead or a plate. In some embodiments, any of the provided anti-idiotype antibodies or antigen-binding fragments thereof is an agonist of a CAR containing the antigen-binding domain of the target antibody when immobilized on a support, such as a bead or a plate. In some embodiments, any of the provided anti-idiotype antibodies or antigen-binding fragments thereof that bind to or recognize the target anti-GPRC5D antibody, or an antigen-binding fragment thereof, is an agonist of a CAR containing the antigen-binding domain of the target anti-GPRC5D antibody when immobilized on a support, such as a bead or a plate. An anti-idiotype antibody or antigen-binding fragment thereof is said to be "an agonist" of a CAR containing a target antibody or antigen-binding fragment thereof when the anti-idiotype antibody or antigen-binding fragment thereof is capable of increasing an activity of the CAR, e.g., T-cell stimulation of cells engineered to express the CAR, by binding to, or otherwise associating with, the CAR.

In some embodiments, an activity of cells includes one or more functions or phenotypes of cells, e.g. T cells, engineered with the recombinant receptor (e.g. CAR). In particular embodiments, the cells are target anti-GPRC5D CAR-expressing T cells and the activity includes one or more functions or phenotypes of the T cells. In some embodiments, assays for functional activity of T cells include, but are not limited to, cytokine production (e.g. by ELISPOT or ELISA), intracellular cytokine staining, cellular proliferation, or cytotoxic lymphocyte (CTL) assay. In some embodiments, proliferative responses of the T cells can be measured, e.g. by incorporation of $^3$H-thymidine, BrdU (5-Bromo-2'-Deoxyuridine) or 2'-deoxy-5-ethynyluridine (EdU) into their DNA or dye dilution assays, using dyes such as carboxyfluorescein diacetate succinimmunomodulatory compoundyl ester (CFSE), CellTrace™ Violet, or membrane dye PKH26.

In some embodiments, assessing the functional activity of cells e.g., T cells, includes measuring cytokine production from T cells after contacting target anti-GPRC5D CAR-expressing T cells with the anti-idiotype antibody or antigen-binding fragment thereof. In some cases, such measured cytokines can include, without limitation, interleukin-2 (IL-2), interferon-gamma (IFNγ), interleukin-4 (IL-4), TNF-alpha (TNFα), interleukin-6 (IL-6), interleukin-10 (IL-10), interleukin-12 (IL-12), granulocyte-macrophage colony-stimulating factor (GM-CSF), CD107a, and/or TGF-beta (TGFβ). Assays to measure cytokines are well known in the art, and include but are not limited to, ELISA, intracellular cytokine staining, cytometric bead array, RT-PCR, ELIS-POT, flow cytometry and bio-assays in which cells responsive to the relevant cytokine are tested for responsiveness (e.g. proliferation) in the presence of a test sample.

In some embodiments, assessing a functional activity of cells, e.g. T cells, includes assessing cell phenotypes, e.g., expression of particular cell surface markers, after contacting target anti-GPRC5D CAR-expressing T cells with the anti-idiotype antibody or antigen-binding fragment thereof. In some embodiments, the T cells, e.g., T cells administered for T cell therapy, are assessed for expression of T cell activation markers, T cell exhaustion markers, and/or T cell differentiation markers. T cell activation markers, T cell exhaustion markers, and/or T cell differentiation markers for assessment include any markers known in the art for particular subsets of T cells, e.g., CD25, CD38, human leukocyte antigen-DR (HLA-DR), CD69, CD44, CD137, KLRG1, CD62$^{low}$, CCR7$^{low}$, CD71, CD2, CD54, CD58, CD244, CD160, programmed cell death protein 1 (PD-1), lymphocyte activation gene 3 protein (LAG-3), T-cell immunoglobulin domain and mucin domain protein 3 (TIM-3), cytotoxic T lymphocyte antigen-4 (CTLA-4), band T lymphocyte attenuator (BTLA) and/or T-cell immunoglobulin and immunoreceptor tyrosine-based inhibitory motif domain (TIGIT) (see, e.g., Liu et al., Cell Death and Disease (2015) 6, e1792). In some embodiments, the assessed cell surface marker is CD25, PD-1 and/or TIM-3. In some embodiments, the assessed cell surface marker is CD25.

In some embodiments, any of the provided anti-idiotype antibodies or antigen-binding fragments thereof that bind to or recognize the target anti-GPRC5D antibody, or an antigen-binding fragment thereof is not blocked by exposure to soluble GPRC5D or by GPRC5D-Fc.

In some embodiments, binding of any of the provided anti-idiotype antibodies or antigen-binding fragments thereof to the target anti-GPRC5D antibody is not blocked by exposure to soluble GPRC5D or by GPRC5D-Fc. In some embodiments, the degree of binding (e.g. percent cells positive, mean fluorescent intensity or other parameter as a measure of binding) is substantially the same when the anti-idiotype antibody or antigen-binding fragment thereof is contacted with the target anti-GPRC5D antibody, or a cell engineered with a recombinant receptor (e.g. CAR) containing in its extracellular binding domain the target anti-GPRC5D antibody, in the presence of soluble GPRC5D or GPRC5D-Fc as compared to the absence of the soluble GPRC5D or GPRC5D-Fc. In some embodiment, binding that is substantially the same means that the degree of binding in the presence of soluble GPRC5D or GPRC5D-Fc (e.g. percent cells positive, mean fluorescent intensity or other parameter as a measure of binding) is retained, such as is no less than 85%, 90%, 92%, 95%, 97% or 100%, of the binding in the absence of the soluble GPRC5D or GPRC5D-Fc.

In some embodiments, the anti-idiotype antibody is an antagonist of the CAR. In some embodiments, binding any of the provided anti-idiotype antibodies or antigen-binding fragments thereof to the target anti-GPRC5D antibody is blocked by exposure to soluble GPRC5D or by GPRC5D-Fc. In some embodiments, the degree of binding (e.g. percent cells positive, mean fluorescent intensity or other parameter as a measure of binding) is decreased or reduced when the anti-idiotype antibody or antigen-binding fragment thereof is contacted with the target anti-GPRC5D antibody, or a cell engineered with a recombinant receptor (e.g. CAR) containing in its extracellular binding domain the target anti-GPRC5D antibody, in the presence of soluble GPRC5D or GPRC5D-Fc as compared to the absence of the soluble GPRC5D or GPRC5D-Fc. In some embodiments, binding that is decreased or reduced means that the degree of binding in the presence of the soluble GPRC5D or GPRC5D-Fc (e.g. percent cells positive, mean fluorescent intensity or other parameter as a measure of binding) is reduced, such as is less than 60%, 50%, 40%, 30%, 20%, 10% or less of the binding in the absence of the soluble GPRC5D or GPRC5D-Fc.

In some embodiments, the provided anti-idiotype antibodies are capable of binding a target anti-GPRC5D moiety, such as the target anti-GPRC5D antibody, with at least a certain affinity, as measured by any of a number of known methods. In some embodiments, the affinity is represented by an equilibrium dissociation constant ($K_D$); in some embodiments, the affinity is represented by $EC_{50}$. In certain embodiments, the binding affinity (EC50) and/or the dissociation constant of the anti-idiotype antibody to the anti-GPRC5D moiety is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, such as between at or about 1 nM and at or about 15 nM, e.g., between at or about 5 and at or about 10 nM. In certain embodiments, the EC50 of the anti-idiotype antibody to the anti-GPRC5D moiety is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, such as between at or about 1 nM and at or about 15 nM, e.g., between at or about 5 and at or about 10 nM. In certain embodiments, the dissociation constant of the anti-idiotype antibody to the anti-GPRC5D antibody is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, such as between at or about 1 nM and at or about 15 nM, e.g., between at or about 5 and at or about 10 nM. In one embodiment, the extent of binding of an anti-idiotype antibody to a moiety unrelated to the target anti-GPRC5D moiety is less than, at, or about 10% of the binding of the antibody to the target anti-GPRC5D moiety as measured, e.g., by a radioimmunoassay (RIA). In one embodiment, the extent of binding of an anti-idiotype antibody to a moiety unrelated to the target anti-GPRC5D moiety is less than, at, or about 40%, 30%, 20%, or 10% of the binding of the antibody to the target anti-GPRC5D moiety as measured, e.g., by a radioimmunoassay (RIA).

In some embodiments, any of the provided anti-idiotype antibodies or antigen-binding fragments thereof this not blocked by exposure to soluble GPRC5D or by GPRC5D-Fc. In some embodiments, any of the provided anti-idiotype antibodies or antigen-binding fragments thereof that bind to or recognize the target anti-GPRC5D antibody, or an antigen-binding fragment thereof, is not blocked by exposure to soluble GPRC5D or by GPRC5D-Fc.

C. Methods of Producing the Antibodies

Also provided are methods of making an anti-idiotype antibody, such as of any of the provided embodiments. In some embodiments, for recombinant production of the anti-idiotype antibody, nucleic acid encoding an antibody, e.g., as described above, may be isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Accordingly, provided herein are methods of producing an anti-idiotype antibody or antigen-binding fragment thereof, such as any of the embodiments provided herein, comprising expressing the heavy chain and/or light chain encoded by a nucleic acid molecule(s) or vector as provided herein in a suitable host cell, and recovering or isolating the antibody.

In addition to prokaryotes, eukaryotic microbes such as filamentous fungi or yeast are suitable cloning or expression hosts for antibody-encoding vectors, including fungi and yeast strains whose glycosylation pathways have been modified to mimic or approximate those in human cells, resulting in the production of an antibody with a partially or fully human glycosylation pattern. See Gemgross, Nat. Biotech. 22: 1409-1414 (2004), and Li et al., Nat. Biotech. 24: 210-215 (2006).

Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells; and NSO cells. In some embodiments, the antibody heavy chains and/or light chains may be expressed in yeast. See, e.g., U.S. Publication No. US 2006/0270045 A1. In some embodiments, a particular eukaryotic host cell is selected based on its ability to make desired post-translational modifications to the heavy chains and/or light chains. For example, in some embodiments, CHO cells produce polypeptides that have a higher level of sialylation than the same polypeptide produced in 293 cells.

In some embodiments, the anti-idiotype antibody is produced in a cell-free system. Exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

The provided embodiments further include vectors and host cells and other expression systems for expressing and producing the antibodies and other binding proteins, including eukaryotic and prokaryotic host cells, including bacteria, filamentous fungi, and yeast, as well as mammalian cells such as human cells, as well as cell-free expression systems.

Host cells comprising any of the nucleic acids or vectors described herein are also provided. In some embodiments, a host cell that expresses an anti-idiotype antibody or antigen binding fragment described herein is provided. The provided anti-idiotype antibody or antigen binding fragment expressed in host cells can be purified by any suitable method. Such methods include, but are not limited to, the use of affinity matrices or hydrophobic interaction chromatography. Suitable affinity ligands include the target anti-GPRC5D antibody, or agents that bind Fc regions. For example, a Protein A, Protein G, Protein A/G, or an antibody affinity column may be used to bind the Fc region and to purify an anti-idiotype antibody that comprises an Fc region.

Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies.

The anti-idiotype antibodies or antibody moieties can be humanized antibodies or human antibodies. A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided anti-idiotype antibodies or antibody moieties are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

D. Immunoconjugates

In some embodiments, the anti-idiotype antibody is or is part of an immunoconjugate (anti-idiotype antibody immunoconjugate), in which the anti-idiotype antibody is conjugated to one or more heterologous molecule(s), such as, but not limited to, a cytotoxic or an imaging agent. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents (e.g., maytansinoids, taxanes, methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins. In some embodiments, the antibody is conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

Among the anti-idiotype antibody immunoconjugates are antibody-drug conjugates (ADCs), in which an anti-idiotype antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714, 586, 5,739,116, 5,767,285, 5,770,701, 5,770,710, 5,773,001, and 5,877,296; Hinman et al., *Cancer Res.* 53: 3336-3342 (1993); and Lode et al., *Cancer Res.* 58: 2925-2928 (1998)); an anthracycline such as daunomycin or doxorubicin (see Kratz et al., *Current Med. Chem.* 13: 477-523 (2006); Jeffrey et al., *Bioorganic & Med. Chem. Letters* 16: 358-362 (2006); Torgov et al., *Bioconj. Chem.* 16: 717-721 (2005); Nagy et al., *Proc. Natl. Acad. Sci. USA* 97: 829-834 (2000); Dubowchik et al., *Bioorg. & Med. Chem. Letters* 12: 1529-1532 (2002); King et al., *J Med. Chem.* 45: 4336-4343 (2002); and U.S. Pat. No. 6,630,579)); methotrexate; vindesine; a taxane such as docetaxel, paclitaxel, larotaxel, tesetaxel, and ortataxel; a trichothecene; and CC1065.

Also among the anti-idiotype antibody immunoconjugates are those in which the antibody is conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

Also among the anti-idiotype antibody immunoconjugates are those in which the anti-idiotype antibody is conjugated to a radioactive atom to form a radioconjugate. Exemplary radioactive isotopes include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

Conjugates of an anti-idiotype antibody and cytotoxic agent may be made using any of a number of known protein coupling agents, e.g., linkers, (see Vitetta et al., *Science* 238: 1098 (1987)), WO94/11026. The linker may be a "cleavable linker" facilitating release of a cytotoxic drug in the cell, such as acid-labile linkers, peptidase-sensitive linkers, photolabile linkers, dimethyl linkers, and disulfide-containing linkers (Chari et al., *Cancer Res.* 52: 127-131 (1992); U.S. Pat. No. 5,208,020).

Also provided are anti-idiotype antibody immunoconjugates comprising an anti-idiotype antibody attached to a label, e.g., a detectable label, which can generate a detectable signal, indirectly or directly. These anti-idiotype antibody immunoconjugates can be used for research or diagnostic applications. The label is preferably capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example $^{99}$Tc or $^{123}$I, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

Examples of detectable labels include but are not limited to radionucleotides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, 0-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin, coumarin, Alexa488, Oregon green 488, rhodamine green, Alexa 532, Cy3, Bodipy 588/586, Alexa586, TAMRA, Rox, Alexa 594, Texas red, Bodipy 630/650, Cy5, Alexa647, IR Dye 680, IR Dye 680, IR Dye 700 DX, Cy5.5, Alexa 750, IR Dye 800CW, IR Dye 800, Atto 532, and Atto 465.

In some embodiments, the anti-idiotype antibody immunoconjugate is detectable indirectly. For example, a secondary antibody that is specific for the anti-idiotype antibody immunoconjugate and contains a detectable label can be used to detect the anti-idiotype antibody immunoconjugate.

E. Variants

In certain embodiments, the anti-idiotype antibodies include one or more amino acid variations, e.g., substitutions, deletions, insertions, and/or mutations, compared to the sequence of an anti-idiotype antibody described herein. Exemplary variants include those designed to improve the binding affinity and/or other biological properties of the anti-idiotype antibody. Amino acid sequence variants of an anti-idiotype antibody may be prepared by introducing appropriate modifications into the nucleotide sequence encoding the anti-idiotype antibody, or by peptide synthesis. Such modifications include, for example, deletions from, and/or insertions into and/or substitutions of residues within the amino acid sequences of the anti-idiotype antibody. Any combination of deletion, insertion, and substitution can be made to arrive at the final construct, provided that the final construct possesses the desired characteristics, e.g., antigen-binding.

In certain embodiments, the anti-idiotype antibodies include one or more amino acid substitutions, e.g., as compared to an anti-idiotype antibody sequence described herein. Sites of interest for substitutional mutagenesis include the CDRs and FRs. Amino acid substitutions may be introduced into an anti-idiotype antibody of interest and the products screened for a desired activity, e.g., retained/improved antigen binding, decreased immunogenicity, improved half-life, and/or improved effector function, such as the ability to promote antibody-dependent cellular cytotoxicity (ADCC) or complement-dependent cytotoxicity (CDC). In some embodiments, the variant anti-idiotype antibody exhibits retained or improved binding to a target anti-GPRC5D antibody or fragment thereof. For example, in some embodiments, the variant anti-idiotype antibody exhibits an increase in binding affinity to the target anti-GPRC5D antibody of at least about 10% (such as at least about any of 20, 30, 40, 50, 60, 70, 80, 90, 100, 200, 300, 400, 500, 1000% or more) as compared to the unmodified anti-idiotype antibody.

In some embodiments, one or more residues within a CDR of a parent antibody (e.g. a humanized or human antibody) is/are substituted. In some embodiments, the substitution is made to revert a sequence or position in the sequence to a germline sequence, such as an antibody sequence found in the germline (e.g., human germline), for example, to reduce the likelihood of immunogenicity, e.g., upon administration to a human individual.

In some embodiments, alterations are made in CDR "hotspots," residues encoded by codons that undergo mutation at high frequency during the somatic maturation process (see, e.g., Chowdhury, Methods Mol. Biol. 207: 179-196 (2008)), and/or residues that contact antigen, with the resulting variant $V_H$ or $V_L$ being tested for binding affinity. Affinity maturation by constructing and reselecting from secondary libraries has been described, e.g., in Hoogenboom et al. in Methods in Molecular Biology 178: 1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant $V_H$ and $V_L$ sequences provided above, each CDR either is unaltered, or contains no more than one, two or three amino acid substitutions.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

Modifications

In certain embodiments, the antibody is altered to increase or decrease the extent to which the antibody is glycosylated, for example, by removing or inserting one or more glycosylation sites by altering the amino acid sequence and/or by modifying the oligosaccharide(s) attached to the glycosylation sites, e.g., using certain cell lines.

Exemplary modifications, variants, and cell lines are described, e.g., in Patent Publication Nos. US 2003/0157108, US 2004/0093621, US 2003/0157108; WO 2000/61739; WO 2001/29246; US 2003/0115614; US 2002/

0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336: 1239-1249 (2004); Yamane-Ohnuki et al. Biotech. Bioeng. 87: 614 (2004). Ripka et al. Arch. Biochem. Biophys. 249: 533-545 (1986); US Pat Appl No US 2003/0157108 A1, Presta, L; and WO 2004/056312 A1, Yamane-Ohnuki et al. Biotech. Bioeng. 87: 614 (2004); Kanda, Y. et al., Biotechnol. Bioeng., 94(4): 680-688 (2006); and WO2003/085107); WO 2003/011878 (Jean-Mairet et al.); U.S. Pat. No. 6,602,684 (Umana et al.); and US 2005/0123546 (Umana et al.); WO 1997/30087 (Patel et al.); WO 1998/58964 (Raju, S.); and WO 1999/22764 (Raju, S.).

Among the modified antibodies are those having one or more amino acid modifications in the Fc region, such as those having a human Fc region sequence or other portion of a constant region (e.g., a human IgG1, IgG2, IgG3 or IgG4 Fc region) comprising an amino acid modification (e.g. a substitution) at one or more amino acid positions.

Such modifications can be made, e.g., to improve half-life, alter binding to one or more types of Fc receptors, and/or alter effector functions.

Also among the variants are cysteine engineered antibodies such as "thioMAbs" and other cysteine engineered variants, in which one or more residues of an antibody are substituted with cysteine residues, in order to generate reactive thiol groups at accessible sites, e.g., for use in conjugation of agents and linker-agents, to produce immunoconjugates. Cysteine engineered antibodies are described, e.g., in U.S. Pat. Nos. 7,855,275 and 7,521,541.

In some embodiments, the antibodies are modified to contain additional nonproteinaceous moieties, including water soluble polymers. Exemplary polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

II. CHIMERIC ANTIGEN RECEPTORS (CARS) AND GENETICALLY ENGINEERED CELLS

In some embodiments, the provided anti-idiotypic antibodies bind to or recognize an antigen-binding portion of a chimeric antigen receptor (CAR), such as an anti-GPRC5D CAR containing an antigen-binding portion derived from the target anti-GPRC5D antibody, as described herein. In some embodiments, the provided anti-idiotype antibodies bind to such CARs expressed on a cell, such as cells used in connection with adoptive cell therapy. In some embodiments, the cells include one or more nucleic acids introduced via genetic engineering, and thereby express the recombinant or genetically engineered CAR products of such nucleic acids. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods. In some embodiments, the provided anti-idiotypic antibodies can be used in methods to modulate one or more of these activities, including to activate, stimulate and/or expand engineered cells expressing the target CAR.

In some embodiments, the cells include one or more nucleic acids introduced via genetic engineering in accord with the provided methods, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types. In particular embodiments, the nucleic acids contain a gene that encodes a CAR.

In some embodiments, the provided methods may be carried out simultaneously, sequentially or concurrently with one or more processing steps for manufacturing or preparing genetically engineered cells. The processing steps of the methods may include any one or more of a number of cell processing steps, alone or in combination. In particular embodiments, the processing steps include transduction or transfection of the cells with one or more nucleic acids, e.g., a heterologous polynucleotide comprising a gene encoding a recombinant receptor. In certain embodiments, cells are transduced with viral vector particles containing a retroviral vector, such as one encoding a recombinant product for expression in the cells. In certain embodiments, the cells are transfected with one or more non-viral nucleic acids, e.g., an episomal plasmid or a transposon. The methods may further and/or alternatively include other processing steps, such as steps for the isolation, separation, selection, washing, suspension, dilution, concentration, and/or formulation of the cells. In some cases, the methods also can include an ex vivo step for cultivation, stimulation or expansion of cells (e.g., stimulation of the cells, for example, to induce their proliferation and/or activation), which, in some cases, can be carried out in accord with the provided methods. In some embodiments, the methods include isolating cells from the subject, preparing, processing, culturing, and/or engineering them, and re-introducing them into the same subject, before or after cryopreservation.

In some embodiments, the method includes processing steps carried out in an order in which: cells, e.g., primary cells, are first isolated, such as selected or separated, from a biological sample; selected cells are incubated with viral vector particles for transduction; and transduced cells are formulated in a composition. In some cases, transduced cells are activated, expanded or propagated ex vivo, such as by stimulation in the presence of a stimulation reagent, such as in accord with the provided methods. In some embodiments, the method can include one or more processing steps from among washing, suspending, diluting and/or concentrating cells, which can occur prior to, during, or simultaneous with or subsequent to one or more of the isolation, such as separation or selection, transduction, stimulation, and/or formulation steps.

In particular embodiments, the cells to be transfected or transduced are not isolated, selected, or enriched prior to contact with the one or more nucleic acids. In some embodiments, the cells are not selected prior to contacting the cells with the one or more nucleic acids. In some embodiments, the cells to be transfected or transduced are not enriched prior to contacting the cells with the one or more nucleic acids.

In some embodiments, one or more of the cell processing steps in connection with preparing, processing and/or incubating cells in connection with the provided method, including in connection with preparing a composition containing genetically engineered cells, can be carried out in the internal cavity of a centrifugal chamber, such as a substantially rigid chamber that is generally cylindrical in shape and rotatable around an axis of rotation, which can provide certain advantages compared to other available methods. In some embodiments, all processing steps are carried out in the same centrifugal chamber. In some embodiments, one or more processing steps are carried out in different centrifugal chambers, such as multiple centrifugal chambers of the same type. Such methods include any of those as described in International Publication Number WO2016/073602.

Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Depending on the particular process (e.g., dilution, wash, transduction, formulation), it is within the level of a skilled artisan to choose a particular kit that is appropriate for the process. Exemplary kits for use with such systems include, but are not limited to, single-use kits sold by BioSafe SA under product names CS-430.1, CS-490.1, CS-600.1 or CS-900.2.

In some embodiments, the system is included with and/or placed into association with other instrumentation, including instrumentation to operate, automate, control and/or monitor aspects of the various processing steps performed in the system. This instrumentation in some embodiments is contained within a cabinet. In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced or transfected and the vector particles, e.g., viral vector particles or non-viral plasmids, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or compositions during the methods. The containers can be connected at one or more positions in the system, such as at a position corresponding to an input line, diluent line, wash line, waste line and/or output line.

In some embodiments, the system, such as a closed system, is sterile. In some embodiments, all connections of components of the system, such as between tubing line and a container via a connector, are made under sterile conditions. In some embodiments, connections are made under laminar flow. In some embodiments, connections are made using a sterile connection device that produces sterile connections, such as sterile welds, between a tubing and a container. In some embodiments, a sterile connection device effects connection under thermal condition high enough to maintain sterility, such as temperatures of at least 200° C., such as at least 260° C. or 300° C.

In some embodiments, the system may be disposable, such as a single-use kit. In some embodiments, a single-use kit can be utilized in a plurality of cycles of a process or processes, such as at least 2, 3, 4, 5 or more times, for example, in processes that occur in a continuous or a semi-continuous manner. In some embodiments, the system, such as a single-use kit, is employed for processing of cells from a single patient. In aspects of the methods, the processes need not be performed in the same closed system, such as in the same centrifugal chamber, but can be performed under a different closed system, such as in a different centrifugal chamber; in some embodiments, such different centrifugal chambers are at the respective points in the methods placed in association with the same system, such as placed in association with the same centrifuge. In some embodiments, all processing steps are performed in a closed system, in which all or a subset of each one or more processing step is performed in the same or a different centrifugal chamber.

A. Target Chimeric Antigen Receptors (CARs)

In some embodiments, the provided anti-idiotypic antibodies bind or recognize the extracellular domain of a target CAR that contains an antigen binding domain of an antibody or antibody fragment that provides specificity for a desired antigen (e.g., tumor antigen) and which is operably linked or connected to an intracellular signaling domain. In some embodiments, the CAR contains an antigen binding domain that is the antigen binding domain of a target antibody or antigen-binding fragment thereof as provided herein. In some embodiments, the provided anti-idiotype antibodies bind or recognize the extracellular domain of a target CAR that contains an antigen binding domain of a target anti-GPRC5D antibody or antibody fragment that provides specificity for a GPRC5D antigen (e.g., expressed on a tumor) that is operably linked or connected to an intracellular signaling domain. In some embodiments, the CAR contains an antigen binding domain that is the antigen binding domain of an anti-GPRC5D target antibody or antigen-binding fragment thereof as provided herein, such as described in Section I. In some embodiments, the antigen binding domain includes the target anti-GPRC5D antibody or an antibody fragment of portion derived from the target anti-GPRC5D antibody, as described herein. Accordingly, in some embodiments, provided herein are anti-idiotypic antibodies or antigen-binding fragments thereof that bind or recognize the extracellular domain of a target CAR that contains a target antibody or antigen-binding fragment thereof, such as the target anti-GPRC5D antibody as described herein, e.g., in Section I, or an antigen-binding fragment thereof. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions.

In some embodiments, engineered cells, such as T cells, are provided that express a CAR with specificity for a particular antigen (or marker or ligand), such as an antigen expressed on the surface of a particular cell type. In some embodiments, the antigen is a polypeptide. In some embodiments, it is a carbohydrate or other molecule. In some embodiments, the antigen is selectively expressed or over-expressed on cells of the disease or condition, e.g., the tumor or pathogenic cells, as compared to normal or non-targeted cells or tissues. In other embodiments, the antigen is expressed on normal cells and/or is expressed on the engineered cells.

In particular embodiments, the recombinant receptor, such as a chimeric receptor, contains an intracellular signaling region, which includes a cytoplasmic signaling domain (also interchangeably called an intracellular signaling domain), such as a cytoplasmic (intracellular) region capable of inducing a primary activation signal in a T cell, for example, a cytoplasmic signaling domain of a T cell receptor (TCR) component (e.g. a cytoplasmic signaling domain of a zeta chain of a CD3-zeta (CD3) chain or a functional variant or signaling portion thereof) that comprises an immunoreceptor tyrosine-based activation motif (ITAM).

In some embodiments, the chimeric receptor further contains an extracellular ligand-binding domain that binds to or recognizes a ligand (e.g. antigen). In some embodiments, the chimeric receptor is a CAR that contains an extracellular antigen-recognition domain that binds to or recognizes an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 March 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some embodiments, the antibody or antigen-binding portion thereof is expressed on cells as part of a CAR. In some embodiments, the extracellular antigen-binding domain is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, the CAR contains an antibody or an antigen-binding fragment (e.g. scFv) that binds to or recognizes GPRC5D, such as an intact antigen, expressed on the surface of a cell. In some embodiments, the antibody or antigen-binding fragment (scFv) includes CDRs contained in the target anti-GPRC5D antibody, as described herein.

In some embodiments, the antigen is GPRC5D and is bound by an anti-GPRC5D antibody, such as the target anti-GPRC5D antibody or an antigen-binding fragment derived from the target anti-GPRC5D antibody.

In some embodiments, the antigen-binding proteins, antibodies and antigen binding fragments thereof recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; variable heavy chain (VH) regions, single-chain antibody molecules such as scFvs and single-domain VH single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

The chimeric receptors, such as CARs, generally include an extracellular antigen binding domain, such as a portion of an antibody molecule (e.g. the target anti-GPRC5D antibody, as described herein), generally a variable heavy (VH) chain region and/or variable light (VL) chain region of the antibody, e.g., an scFv antibody fragment.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv. In some embodiments, the scFv is derived from the target anti-GPRC5D antibody and comprises the sequence of amino acids set forth in SEQ ID NO: 9.

In some embodiments, the recombinant receptor such as the CAR, such as the antibody portion thereof, further includes a spacer, which may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. In some embodiments, the spacer has the sequence set forth in SEQ ID NO: 11. In some embodiments, the spacer includes a sequence of a hinge region, a $C_H2$ and a $C_H3$ region. In some embodiments, one of more of the hinge, $C_H2$ and $C_H3$ is derived all or in part from IgG4 or IgG2. In some cases, the hinge, $C_H2$ and $C_H3$ is derived from IgG4. In some aspects, one or more of the hinge, $C_H2$ and $C_H3$ is chimeric and contains sequence derived from IgG4 and IgG2. In some examples, the spacer contains an IgG4/2 chimeric hinge, an IgG2/4 $C_H2$, and an IgG4 $C_H3$ region. In some embodiments, the encoded spacer is or contains (i) the sequence set forth in SEQ ID NO: 11; (ii) a functional variant of SEQ ID NO: 11 that has at least 95%, 96%, 97%, 98% or 99% sequence identity to SEQ ID NO: 11; or (iii) a contiguous portion of (i) or (ii) that is at least 125 amino acids in length. In some embodiments, the encoded spacer is or includes the sequence set forth in SEQ ID NO: 11. Exemplary spacers include, but are not limited to, those described in Hudecek et al. (2013) *Clin. Cancer Res.,* 19: 3153, international patent application publication number WO2014031687, U.S. Pat. No. 8,822,647, published app. No. US2014/0271635, WO 2019/090003 (PCT/US2018/058811), or WO 2016/090320 (PCT/US2015/064112), the contents of which are hereby incorporated by reference.

In some embodiments, the antigen receptor comprises an intracellular domain linked directly or indirectly to the extracellular domain. In some embodiments, the chimeric antigen receptor includes a transmembrane domain linking the extracellular domain and the intracellular signaling domain. In some embodiments, the transmembrane domain is fused to the extracellular domain. In some embodiments, the intracellular signaling domain comprises an ITAM. For example, in some aspects, the antigen recognition domain (e.g. extracellular domain) generally is linked to one or more intracellular signaling components, such as signaling components that mimic activation through an antigen receptor complex, such as a TCR complex, in the case of a CAR, and/or signal via another cell surface receptor. In some embodiments, the chimeric receptor comprises a transmembrane domain linked or fused between the extracellular domain (e.g. scFv) and intracellular signaling domain. Thus, in some embodiments, the antigen-binding component (e.g., antibody) is linked to one or more transmembrane and intracellular signaling domains.

In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154. Alternatively, the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28.

In some embodiments, the extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

The receptor, e.g., the CAR, generally includes at least one intracellular signaling component or components. In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from CD3 zeta chain, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor $\gamma$, CD8, CD4, CD25, or CD16. For example, in some aspects, the CAR or other chimeric receptor includes a chimeric molecule between CD3-zeta (CD3-$\zeta$) or Fc receptor $\gamma$ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some embodiments, the chimeric antigen receptor contains an intracellular domain of a T cell costimulatory molecule. In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the antigen receptor further includes a marker and/or cells expressing the CAR or other antigen receptor further includes a surrogate marker, such as a cell surface marker, which may be used to confirm transduction or engineering of the cell to express the receptor. In some aspects, the marker includes all or part (e.g., truncated form) of CD34, a NGFR, or epidermal growth factor receptor, such as truncated version of such a cell surface receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. In embodiments, the tEGFR contains the amino acid sequence set forth in SEQ ID NO: 33. In some embodiments, the tEGFR contains an amino acid sequence with or with about 75%, 76%, 77%, 78%, 79%, 80%, 81%, 82%8, 83%, 84%, 85%, 86%, 87%, 88%, 89%, 90%, 91%, 92%, 93%, 94%, 95%, 96%, 97%, 98%, 99%, or greater than 99% sequence identify to the sequences set forth in SEQ ID NO: 33.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing the antibody or fragment described herein, e.g., a target antibody or antigen-binding fragment thereof, such as the target anti-GPRC5D antibody, or an antigen-binding fragment thereof. In some aspects, the chimeric antigen receptor includes an extracellular portion containing the antibody or fragment described herein and an intracellular signaling domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain disposed between the extracellular domain and the intracellular signaling region.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 4-1BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97% 98%, 99% or more sequence identity to SEQ ID NO: 12.

In some embodiments, the chimeric antigen receptor contains an intracellular domain of a T cell costimulatory molecule. In some aspects, the T cell costimulatory molecule is CD28 or 4-1BB.

In some embodiments, the intracellular signaling region comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 34 or 35 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 34 or 35. In some embodiments, the intracellular region comprises an intracellular costimulatory signaling domain of 4-1BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 13 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13.

In some embodiments, the intracellular signaling region comprises a human CD3 chain, optionally a CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or U.S. Pat. No. 8,911,993. In some embodiments, the intracellular signaling region comprises the sequence of amino acids set forth in SEQ ID NO: 14 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 14.

In some aspects, the spacer contains only a hinge region of an IgG, such as only a hinge of IgG4 or IgG1, such as the hinge only spacer set forth in SEQ ID NO: 11. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO: 37. In some embodiments, the spacer is an Ig hinge, e.g., an IgG4 hinge, linked to a $C_H3$ domain only, such as set forth in SEQ ID NO: 36. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, a single promoter may direct expression of an RNA that contains, in a single open reading frame (ORF), two or three genes (e.g. encoding the molecule involved in modulating a metabolic pathway and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. Genetic Vaccines and Ther. 2:13 (2004) and deFelipe et al. *Traffic* 5:616-626 (2004)). Many 2A elements are known in the art. Examples of 2A sequences that can be used in the methods and nucleic acids disclosed herein, without limitation, 2A sequences from the foot-and-mouth disease virus (F2A, e.g., SEQ ID NO: 43), equine rhinitis A virus (E2A, e.g., SEQ ID NO: 41), Thosea asigna virus (T2A, e.g., SEQ ID NO: 38 or 45), and porcine teschovirus-1 (P2A, e.g., SEQ ID NO: 39 or 40) as described in U.S. Patent Publication No. 20070116690.

The recombinant receptors, such as CARs, expressed by the cells administered to the subject generally recognize or bind to a molecule that is expressed in, associated with, and/or specific for the disease or condition or cells thereof being treated. Upon binding, e.g., specific binding, to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that binds to an antigen expressed by a cell or tissue of the disease or condition or associated with the disease or condition. The receptor may be another receptor such as an immunoinhibitory or costimulatory signal-promoting receptor, such as a CCR or iCAR or non-signaling receptor, e.g., for use in depletion or elimination of cells using the antibodies.

B. Genetically Engineered Cells and Methods of Producing Cells

Among the cells expressing the chimeric antigen receptors are engineered cells. The genetic engineering generally involves introduction of a nucleic acid encoding the recombinant or engineered component into a composition containing the cells, such as by retroviral transduction, transfection, or transformation. Various methods for the introduction of genetically engineered components, e.g., recombinant receptors, e.g., CARs, are well known and may be used. Exemplary methods include those for transfer of nucleic acids encoding the receptors, including via viral, e.g., retroviral or lentiviral, transduction, transposons, and electroporation.

1. Vectors and Methods for Genetic Engineering

Also provided are one or more polynucleotides (e.g., nucleic acid molecules) encoding chimeric antigen receptors (CARs), vectors for genetically engineering cells to express such CARs and methods for producing the engineered cells. In some embodiments, the vector contains the nucleic acid encoding the CAR. In some cases, the vector is a viral vector, such as a retroviral vector, e.g., a lentiviral vector or a gammaretroviral vector.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7: 980-990; Miller, A. D. (1990) Human Gene Therapy 1: 5-14; Scarpa et al. (1991) Virology 180: 849-852; Burns et al. (1993) Proc. Natl. Acad. Sci. USA 90: 8033-8037; and Boris-Lawrie and Temin (1993) Cur. Opin. Genet. Develop. 3: 102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion, e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the anti-CD3/anti-CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907: 645-66 or Barrett et al., Chimeric Antigen Receptor Therapy for Cancer Annual Review of Medicine Vol. 65: 333-347 (2014). In some embodiments, the cells are stimulated with a provided anti-idiotype antibody in accord with the provided methods.

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11: 6 (1991); and Riddell et al., *Human Gene Therapy* 3: 319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

2. Cells and Preparation of Cells for Genetic Engineering

Provided herein are cells, including engineered cells that contain a chimeric antigen receptor (CAR). Also provided are population of such cells and compositions containing such cells. Among the compositions are input compositions containing cells in which one or more cells is known or likely or will express a recombinant receptor capable of being recognized or bound by a binding molecule present on one or more particles to which the cells are incubated or contacted. Also among the compositions are compositions produced by the provided methods, including output compositions in which is contained stimulated or expanded cells, including compositions enriched for cells containing a recombinant receptor bound or recognized by the binding molecule of the particle, such as in which cells expressing the recombinant receptor, e.g. chimeric receptor, make up at least 50, 60, 70, 80, 90, 91, 92, 93, 94, 95, 96, 97, 98, 99, or more percent of the total cells in the composition or cells of a certain type such as T cells or CD8+ or CD4+ cells. Thus, provided are genetically engineered cells expressing the recombinant receptors e.g., CARs.

Among the compositions are pharmaceutical compositions and formulations for administration, such as for adoptive cell therapy. Also provided are methods for engineering, producing or generating such cells, therapeutic methods for administering the cells and compositions to subjects, e.g., patients, and methods for detecting, selecting, isolating or separating such cells.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs).

The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, prior to the selection and/or enrichment of cells, the sample or the cells in the sample can be rested or held prior to further processing steps. In some embodiments, the sample is maintained at or held at a temperature of from or from about 2° C. to 8° C. for up to 48 hours, such as for up to 12 hours, 24 hours or 36 hours. In certain embodiments, the cells are not selected and/or enriched prior to contacting the cells with the one or more nucleic acids. In some embodiments, the sample or the cells can be rested or held prior to contacting or incubating the cells with one or more nucleic acids. In certain embodiments, the sample is maintained at or held at a temperature of from or from about 2° C. to 8° C. for up to 48 hours, such as for up to 12 hours, 24 hours or 36 hours prior to contacting or incubating the cells with one or more nucleic acids.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, CD3+, CD28+ T cells can be positively selected using CD3/CD28 conjugated magnetic beads (e.g., DYNABEADS® M-450 CD3/CD28 T Cell Expander). In particular embodiments, cells are contacted with anti-CD3/anti-CD28 conjugated magnetic beads (e.g., DYNA-BEADS® M-450 CD3/CD28 T Cell Expander) to expand CD3+, CD28+ T cells prior to contacting the cells with the one or more nucleic acids. In certain embodiments, the cells are not contacted with anti-CD3/anti-CD28 conjugated magnetic beads prior to contacting the cells with the one or more nucleic acids.

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate CD4+ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1: 72-82; Wang et al. (2012) *J Immunother.* 35(9): 689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-$ $CD8^+$ and/or $CD62L^+$ $CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8$^+$ cell population or subpopulation, also is used to generate the CD4$^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4$^+$ cells, where both the negative and positive fractions are retained. The negative fraction then is subjected to negative selection based on expression of CD14 and CD45RA, and positive selection based on a marker characteristic of central memory T cells, such as CD62L or CCR7, where the positive and negative selections are carried out in either order.

CD4$^+$ T helper cells are sorted into naïve, central memory, and effector cells by identifying cell populations that have cell surface antigens. CD4$^+$ lymphocytes can be obtained by standard methods. In some embodiments, naive CD4$^+$ T lymphocytes are CD45RO$^-$, CD45RA$^+$, CD62L$^+$, CD4$^+$ T cells. In some embodiments, central memory CD4$^+$ cells are CD62L$^+$ and CD45RO$^+$. In some embodiments, effector CD4$^+$ cells are CD62L$^-$ and CD45RO$^-$.

In one example, to enrich for CD4$^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher® Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynabeads™ or MACS® beads). The magnetically responsive material, e.g., particle, generally is directly or indirectly attached to a binding partner, e.g., an antibody, that binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which bind to such antibodies or binding partners, which are attached to the magnetic particle or bead, bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS®) (Miltenyi Biotec, Auburn, CA). Magnetic Activated Cell Sorting (MACS®) systems are capable of high-purity selection of cells having magnetized particles attached thereto. In certain embodiments, MACS® operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1. In one example, the system is a system as described in International Publication Number WO2016/073602.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS® system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS® system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS® Prodigy system (Miltenyi Biotec). The CliniMACS® Prodigy system in some aspects is equipped with a cell processing unity that permits automated washing and fractionation of cells by centrifugation. The CliniMACS® Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS® Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) *Blood.* 1: 72-82, and Wang et al. (2012) *J Immunother.* 35(9): 689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5): 355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) *Blood.* 1: 72-82, and/or Wang et al. (2012) *J Immunother.* 35(9): 689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

III. COMPOSITIONS

Also provided are compositions including the binding molecules, such as anti-idiotype antibodies or antigen-binding fragments thereof, as provided herein, including pharmaceutical compositions and formulations. Also provided are compositions including the anti-idiotype antibodies or antigen-binding fragments thereof, as provided herein, including pharmaceutical compositions and formulations. The compositions and formulations generally include one or more optional acceptable carriers or excipients.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell, binding molecule, and/or antibody, and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.0010% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

In some aspects, the composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.00010% to about 2% by weight of the total composition. Carriers are described, e.g., by Remington's Pharmaceutical Sciences 16th edition, Osol, A. Ed. (1980). Acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Formulations of the antibodies can include lyophilized formulations and aqueous solutions.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the binding molecule in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The compositions can also be lyophilized. The compositions can contain auxiliary substances such as wetting, dispersing, or emulsifying agents (e.g., methylcellulose), pH buffering agents, gelling or viscosity enhancing additives, preservatives, colors, and the like. Standard texts may in some aspects be consulted to prepare suitable preparations.

The formulations to be used for in vivo administration are generally sterile. Sterility may be readily accomplished, e.g., by filtration through sterile filtration membranes.

IV. METHODS AND USES

In some embodiments, provided herein are methods involving the use of one or more anti-idiotype antibodies. In some aspects, provided herein are methods for measuring or detecting a target antibody, such as a CAR or a cell expressing a CAR, and methods for modifying the activity of the target antibody, such as the activity of a CAR or the activity of a cell expressing a CAR. In some aspects, provided herein are methods for measuring or detecting a target antibody, such as a CAR or a cell expressing a CAR. In certain embodiments, the one or more anti-idiotype antibodies bind, detect, identify, purify, select, and/or quantify the CAR and/or cells expressing the CAR. In some aspects, also provided herein are methods for modifying the activity of the target antibody, such as the activity of a CAR or the activity of a cell expressing a CAR. In some embodiments, the methods provided herein provide one or more steps of contacting and/or incubating the one or more anti-idiotype antibodies with a cell or a sample containing or thought to be containing cells that express a chimeric antigen receptor (CAR). In some embodiments, the anti-idiotype antibody is treated, incubated, and/or contacted with the composition or sample under conditions that allow for the formation of a complex between the anti-idiotype antibody and the target antibody, e.g., the CAR. In some aspects, the complex may be utilized for the purposes of detecting, isolating, and/or measuring the CAR. In some embodiments, the formation of the complex modifies the activity of the target antibody, e.g., the CAR, such as by stimulating receptor signaling activity, or in some embodiments, antagonizing the activity of the target antibody, e.g., the CAR, by preventing the association of the CAR with an antigen. In some embodiments, the CAR is a CAR expressing the target anti-GPRC5D antibody, or an antigen-binding fragment thereof, as described herein, e.g., in Section I.

A. Detection/Isolation Methods

In some embodiments, there are provided methods involving use of one or more of the anti-idiotype antibodies, and/or molecules (such as conjugates and complexes) containing one or more of such anti-idiotype antibodies, for detecting, binding, selecting, and/or isolating an antibody, e.g., a target antibody. In certain embodiments, the methods provide one or more steps of contacting, incubating, and/or exposing the one or more anti-idiotype antibodies to a sample and/or composition.

In some embodiments, the methods include (a) contacting a composition comprising a target antibody or antigen-binding fragment thereof (e.g., the target anti-GPRC5D antibody, or an antigen-binding fragment thereof) with an anti-idiotype antibody or antigen-binding fragment thereof provided herein, or an anti-idiotype antibody immunoconjugate provided herein, that binds to or recognizes the target antibody or antigen-binding fragment thereof, and (b) detecting the anti-idiotype antibody or antigen-binding fragment thereof bound to the target antibody or antigen-binding fragment thereof.

In some embodiments, the methods include (a) contacting a cell expressing a CAR comprising a target antibody or antigen-binding fragment thereof (e.g., the target anti-GPRC5D antibody, or an antigen-binding fragment thereof) with an anti-idiotype antibody or antigen-binding fragment thereof provided herein, or an anti-idiotype antibody immunoconjugate provided herein, that binds to or recognizes the target antibody or antigen-binding fragment thereof, and (b) detecting the anti-idiotype antibody or antigen-binding fragment thereof bound to the target antibody or antigen-binding fragment thereof.

In some embodiments, the methods include (a) contacting a cell population expressing a CAR comprising a target antibody or antigen-binding fragment thereof (e.g., the target anti-GPRC5D antibody, or an antigen-binding fragment thereof) or a cell bound to a target antibody or antigen-binding fragment thereof (e.g., the target anti-GPRC5D antibody, or an antigen-binding fragment thereof) with an anti-idiotype antibody or antigen-binding fragment thereof provided herein, or an anti-idiotype antibody immunoconjugate provided herein, that binds to or recognizes the target antibody or antigen-binding fragment thereof, and (b) selecting cells bound with the anti-idiotype antibody or antigen-binding fragment thereof.

In some embodiments, the sample and/or composition has, is likely to have, and/or is suspected of having a target antibody and/or antigen binding fragment thereof that is bound by and/or recognized by the one or more anti-idiotype antibodies. In certain embodiments, the antibody or antigen binding fragment thereof that is bound by or recognized by the one or more anti-idiotype antibodies contains one or more fusion domains and/or is a fusion protein. In certain embodiments, the target antibody and/or antigen binding fragment thereof is a CAR. In certain embodiments, the anti-idiotype antibody, binds to and/or recognizes an anti-GPRC5D antibody (e.g., the target anti-GPRC5D antibody), or an antigen-binding fragment thereof, including a chimeric molecule or conjugate including a CAR, containing such anti-GPRC5D antibody (e.g., antibody fragment). In certain embodiments, the anti-idiotype antibody, binds to and/or recognizes more than one anti-GPRC5D antibody (e.g., the target anti-GPRC5D antibody), or an antigen-binding fragment thereof, including a chimeric molecule or conjugate including a CAR, containing such anti-GPRC5D antibody (e.g., antibody fragment).

In some embodiments, the anti-GPRC5D target antibody or antigen-binding fragment is bound to a cell or expressed on the surface of a cell. In some embodiments, the anti-GPRC5D target antibody or antigen-binding fragment is contained in a chimeric antigen receptor (CAR), such as a CAR expressed on the surface of a cell. In some embodiments, the cell is a stem cell, e.g., an iPSC, or an immune cell. In some embodiments, the immune cell is a T cell. The T cell can include a CD4+ T cell or a CD8+ T cell, or any subset thereof. For instance, the T cell can be a naïve T ($T_N$) cell, effector T cell ($T_{EFF}$), memory T cell, tumor-infiltrating lymphocyte (TIL), immature T cell, mature T cell, helper T cells, cytotoxic T cell, mucosa-associated invariant T (MAIT) cell, naturally occurring and adaptive regulatory T (Treg) cell, helper T cell, such as a TH1 cell, TH2 cell, TH3 cell, TH17 cell, TH9 cell, TH22 cell, follicular helper T cell, alpha/beta T cell, and/or a delta/gamma T cells. In some embodiments, the cell is from a tissue, e.g., heart, vasculature, salivary glands, esophagus, stomach, liver, gallbladder, pancreas, intestines, colon, rectum, hypothalamus, pituitary gland, pineal gland, thyroid, parathyroid, adrenal gland, kidney, ureter, bladder, urethra, lymphatic system, skin, muscle, brain, spinal cord, nerves, ovaries, uterus, testes, prostate, pharynx, larynx, trachea, bronchi, lungs, diaphragm, bone, cartilage, ligaments, or tendons.

In some embodiments, the cell is a T cell isolated or selected from a sample from a subject (e.g. human subject) and engineered to express the target CAR containing in its extracellular antigen-binding domain the anti-GPRC5D target antibody. For instance, in some embodiments, a composition of CAR-expressing T cells can be produced by a process that includes isolating or selecting T cells (e.g. CD3+, or CD4+ and/or CD8+ T cells) from an apheresis or leukapheresis sample from a subject (e.g. human subject), activating the isolated to selected T cells (e.g. with anti-CD3/anti-CD28 reagent, such as anti-CD3/anti-CD28 beads (e.g. Dynabeads), and then transducing the activated cells with a vector encoding the target anti-GPRC5D CAR containing in its extracellular antigen-binding domain the anti-GPRC5D target antibody. In some cases, the transduced T cells may be further incubated or cultured in the presence of one or more stimulatory reagents (e.g. recombinant IL-2, IL-7 and/or IL-15) under conditions for proliferation or expansion of the CAR-expressing T cells. In some embodiments, provided methods can include contacting a composition of T cells containing target anti-GPRC5D CAR-expressing T cells with a provided anti-idiotype antibody or antigen-binding fragment and detecting or selecting T cells bound with the anti-idiotype antibody or antigen-binding fragment. In some embodiments, the provided methods can be used to quantify or determine the number of target anti-GPRC5D CAR-expressing T cells in the composition of T cells as a percentage or number compared to the total cells or total T cells in the composition.

In particular embodiments, target antibody, e.g., the CAR is not bound or contained within a cell, for example, in some embodiments, the target antibody is secreted. In certain embodiments, the antibody has been detached, removed, and/or lysed from the surface of a cell.

The methods in some embodiments include incubating, treating, and/or contacting a sample and/or a composition containing or suspected of containing the target antibody with the anti-idiotype antibody. In certain embodiments, the incubating is under conditions permissive for binding of the anti-idiotype antibody to the target antibody present in the composition, for example to form a complex containing the anti-idiotype antibody and the target antibody.

The methods in some embodiments include incubating, treating, and/or contacting a sample and/or a composition containing or suspected of containing the target anti-GPRC5D antibody, or a target anti-GPRC5D CAR containing the target antibody, with the anti-idiotype antibody. For instance, the sample or composition can include a composition of cells, such as T cells, known or suspected of containing cells expressing the target anti-GPRC5D CAR. In certain embodiments, the incubating is under conditions permissive for binding of the anti-idiotype antibody to the target anti-GPRC5D antibody present in the composition, for example to form a complex containing the anti-idiotype antibody and the target anti-GPRC5D antibody.

In some embodiments, the sample and/or composition contains or is suspected of containing the target antibody, e.g., a CAR. In certain embodiments, the sample and/or composition contains or is suspected of containing cells that express the target antibody, e.g., a CAR. In particular embodiments, the cells are T cells that express a CAR having an extracellular antigen-binding domain containing the target anti-GPRC5D antibody. In some embodiments the T cells are CD3+ T cells. In some embodiments, the T cells are CD8+ T cells. In some embodiments, the T cells are CD4+ T cells. In some embodiments, the composition contains T cells expressing a targeting anti-GPRC5D CAR that includes CD4+ and CD8+ T cells. In some embodiments, the sample or composition is a sample of T cells produced or engineered with the target anti-GPRC5D CAR ex vivo, for example, from T cells isolated from a biological sample from the subject (e.g. apheresis or leukapheresis sample). In some embodiments, the sample or composition is a sample known or suspected of containing target anti-GPRC5D CAR-expressing T cells obtained directly from a sample from a subject, for example, a subject that had been previously administered a dose of a therapeutic composition containing target anti-GPRC5D CAR-expressing Tcells. In certain embodiments, the sample is a biological sample. In particular embodiments, the sample is a serum sample or a blood sample. In some embodiments, the biological sample contains one or more immune cells. In some embodiments, the biological sample is or is derived from a tissue, such as connective tissue, muscle tissue, nervous tissue, or epithelial tissue. In particular embodiments, the biological sample is or is derived from heart, vasculature, salivary glands, esophagus, stomach, liver, gallbladder, pancreas, intestines, colon, rectum, hypothalamus, pituitary gland, pineal gland, thyroid, parathyroid, adrenal gland, kidney, ureter, bladder, urethra, lymphatic system, skin, muscle, brain, spinal cord, nerves, ovaries, uterus, testes, prostate, pharynx, larynx, trachea, bronchi, lungs, diaphragm, bone, cartilage, ligaments, or tendons. In particular embodiments, the biological sample is taken, collected, and/or obtained from a human subject. In certain embodiments, the sample contains cells that are live and/or intact. In some embodiments, the sample is or contains a homogenate and/or cells that have been disrupted and/or lysed. In some embodiments, the biological sample contains proteins and/or antibodies that have been isolated from blood, serum, and/or a tissue.

In particular embodiments, the anti-idiotype antibody forms or is capable of forming a complex with a target antibody, e.g., a CAR. In particular embodiments, the anti-idiotype antibody forms or is capable of forming a complex with a target antibody, e.g., contained in a CAR. In particular embodiments, the complex is detected, measured, quantified, and/or assessed, for example, to allow for the detection, identification, measurement, and/or quantification of the target antibody, for example in a composition or a sample. In certain embodiments, the methods include detecting whether a complex is formed between the anti-idiotype antibody and the target antibody in the sample, and/or detecting the presence or absence or level of such binding. In some embodiments, the complex contains a detectable label. In particular embodiments, the anti-idiotype antibody is an immunoconjugate that contains a detectable label. In certain embodiments, the anti-idiotype antibody contains, is conjugated with, bound to, and/or attached to the detectable label. In some embodiments, the complex contains an antibody that binds to and/or recognizes the anti-idiotype antibody, e.g., a secondary antibody, that in conjugated with, bound to, and/or attached to a detectable label.

In some embodiments, methods for detecting, quantifying, detecting, and/or assessing a target antibody, for example in a sample or composition, includes detecting a complex of the target antibody and the anti-idiotype antibody. In some embodiments, the complex contains a detectable label. In some embodiments, the antibodies provided herein can be conjugated directly or indirectly to a moiety that is capable of detection. In some examples, one or more of the antibodies are modified to permit detection of binding. For example, antibodies can be conjugated to a detectable molecule that permits either direct detection or detection via secondary agents. In some embodiments, the label is a detectable label (e.g., a fluorescent dye label). In some embodiments, the label is an affinity label (e.g., a biotin label). Methods for directly or indirectly attaching label to an antibody are well known in the art. Labels and labeling kits are commercially available such as from Invitrogen Corp, Carlsbad, Calif. In some embodiments, the label is compatible for use in a detection assay. In some embodiments, the label is compatible for use in a diagnostic assay. Labels contemplated herein include, but are not limited to, fluorescent dyes, fluorescent proteins, radioisotopes, chromophores, metal ions, gold particles (e.g., colloidal gold particles), silver particles, particles with strong light scattering properties, magnetic particles (e.g., magnetic bead particles such as Dynabeads® magnetic beads), polypeptides (e.g., FLAG™ tag, human influenza hemagglutinin (HA) tag, etc.), enzymes such as peroxidase (e.g., horseradish peroxidase) or a phosphatase (e.g., alkaline phosphatase), streptavidin, biotin, luminescent compounds (e.g., chemiluminescent substrates), oligonucleotides, members of a specific binding pair (e.g., a ligands and its receptor) and other labels well known in the art that are used for visualizing or detecting an antibody when directly or indirectly attached to said antibody. In some embodiments, the label is a horseradish peroxidase, which can be detecting by adding an appropriate substrate that produces a color change in the presence of horseradish peroxidase. In some embodiments, the label is a colloidal gold particles, which can be detecting by detecting a color change in the solution due to aggregation of the gold particles. Other methods for detecting gold particle labeled antibodies are well known in the art (see Dykman et al. (2011) Acta Naturae. 3(2):34-55). In some examples, the antibodies can be detected using a secondary reagent, such as by a secondary antibody reagent that binds to the primary antibodies as provided herein and that is coupled to a detectable protein, such as a fluorescent probe or detectable enzyme, such as horseradish peroxidase.

In certain embodiments, the complex is probed and/or contacted with a detectable label. In some embodiments, the complex is detected by any suitable method or means, such as but not limited to flow cytometry, immunocytochemistry, immunohistochemistry, western blot analysis, and ELISA. In some embodiments, the cells bound with the anti-idiotype antibody or antigen-binding fragment thereof are selected by affinity-based separation, e.g., immunoaffinity-based separation. In some embodiments, the affinity-based separation is by flow cytometry. In some embodiments, the affinity-based separation is by magnetic activated cell sorting. In some embodiments, the affinity-based separation is by affinity chromatography. In some embodiments, the affinity-based separation is by affinity chromatography and the anti-idiotype antibody or antigen-binding fragment thereof is reversibly bound or immobilized to a support or a stationary phase.

In some embodiments, the sample or composition is mixed with the anti-idiotype antibody or antigen-binding fragment in the presence of or on or in a solid support or a device comprising a solid support. In some embodiments, the sample or composition is mixed with the one or more anti-idiotype antibody or antigen-binding fragment to produce a mixture and the mixture is subsequently applied to a solid support or a device comprising a solid support. In some of the embodiments herein, the anti-idiotype antibody or antigen-binding fragment is directly or indirectly attached to the solid support. In some embodiments, the contacting includes incubation of the sample or composition and the anti-idiotype antibody or antigen-binding fragment. The one or more incubations can be for a time that is suitable to allow the sample to contact the one or more antibody such as for at least or at least about 30 seconds, 1 minute, 5 minutes, 10 minutes, 15 minutes, 20 minutes, 30 minutes, 45 minutes, 1 hour, 2 hours, 3 hours, 6 hours, or 12 hours or more but no more than about 24 hours after contacting a sample with the one or more antibody as described herein. In some embodiments, the contacting occurs at a temperature of from or from about 0° C. to about 50° C., such as typically 2° C. to 8° C. or 23° C. to 28° C. or 37° C. to 42° C. In some embodiments, methods can include one or more washing steps after the contacting or incubating under conditions to retain bound anti-idiotype antibody or antigen-binding fragment on the solid support and/or to separate the complex away from portions of the sample not part of the complex.

In some embodiments, the contacted is carried out under conditions to form a complex comprising the antibody or antigen-binding fragment bound to the anti-GPRC5D target antibody, e.g. contained in a CAR expressed by a cell in the composition. In some embodiments, detection of binding can be achieved by detection techniques commonly known in the art for detecting the binding between a protein target and binding agent (e.g. an antibody) such as, but not limited to, spectrophotometry, high performance liquid chromatography (HPLC), immunoassays such as enzyme-linked immunosorbent assay (ELISA), western blot, automated imaging, immunohistochemistry, flow cytometry, high-throughput screening of an array such as a microarray or nanoarray and surface plasmon resonance. In some embodiments, the antibodies provided herein can detect an anti-GPRC5D target antibody, e.g. contained in a CAR expressed by a cell in the composition, using any binding assay or immunoassay known to one of skill in the art including, but not limited to, enzyme linked immunosorbent assay (ELISA) or other similar immunoassay, including a sandwich ELISA or competitive ELISA; immunohistochemistry (IHC); flow cytometry, or western blot.

In some embodiments, the provided methods for detecting, quantifying, and/or assessing a target antibody, for example in a sample or composition, are performed using a cartridge-based flow method (see, e.g., WO 2011/128893, WO 2014/097286, WO 2014/097287, US 2014/0170678, US 2015/0330971, the contents of which are incorporated by reference in their entireties). In some embodiments, the cartridge-based flow method is performed using a microfluidic device, for instance a device including a microfluidics cartridge and a cartridge handling unit. In certain aspects, use of a cartridge-based flow method obviates the need for special cleaning, maintenance, or use of sheath fluid in the cartridge handling unit. In some embodiments, such methods can be used as part of manufacturing, analytic, and/or quality control methods, e.g., in association with the generation of cell therapies expressing recombinant polypeptides, e.g., CARs, containing an antibody or fragment thereof recognized by the anti-idiotype antibody provided herein. In some embodiments, such methods can be used for testing purposes, including to detect, assay, and/or confirm expression of the engineered receptor, e.g., in cells engineered for use in therapy in an individual. In some embodiments, such methods are used to determine the dose of CAR-T cells to be administered to an individual. In certain embodiments, the cell compositions can be tested at any stage in the process of generating CAR expressing T cells. In particular embodiments, a sample of cells may be collected from a cell composition at any stage of the process and stored, e.g., by cryofreezing and/or cryopreservation, for later testing and/or analysis. The compositions tested may be pharmaceutical compositions e.g., including those containing the cells and a pharmaceutically acceptable recipient and/or cryopreservative agent.

In some embodiments, the cartridge-based flow method is an automated method (e.g., one requiring minimal operator input). In certain aspects, the automated method reduces costs associated with operators and/or expensive equipment. In certain aspects, the automated method is easier to perform and faster than those using traditional assays, e.g., flow cytometry assays. In certain aspects, the automated method reduces the processing time of a sample, for instance down to about 30 to 40 minutes per sample. In some embodiments, the automated method is more consistent and robust than those performed using traditional assays.

In some embodiments, the microfluidic device is a benchtop instrument. In certain aspects, the smaller footprint of the microfluidic device allows for deployment of the device directly in cell processing or testing rooms. In certain aspects, the amount of samples that would need to be moved between rooms and/or labs is reduced, thereby reducing chain of identity and/or chain of custody concerns associated with transferring samples.

In some embodiments, the microfluidic cartridge contains a sample composition chamber. In some embodiments, the microfluidic cartridge contains a blister compartment. In some embodiments, the microfluidic cartridge contains a treatment compartment adapted for fluid mixing, said treatment compartment in fluid communication with the sample composition chamber and the blister. In some embodiments, the microfluidic cartridge contains an evaluation chamber including a reading zone, wherein the evaluation chamber is in fluid communication with the treatment chamber. In some embodiments, the reading zone allows for analysis of the sample as it passes through the reading zone.

In some embodiments, the sample is placed inside the sample composition chamber. In some embodiments, the blister contains an anti-idiotype antibody or antigen-binding fragment thereof provided herein. In some embodiments, the anti-idiotype antibody or antigen-binding fragment thereof is conjugated to a detectable label, e.g., a fluorescent tag. In some embodiments, the microfluidic cartridge is inserted into the cartridge handling unit. In some embodiments, the cartridge handling unit contacts and/or mixes the sample with the anti-idiotype antibody or antigen-binding fragment thereof in the treatment compartment. In some embodiments, the contacting and/or mixing leads to formation of a complex of the target antibody, e.g., CAR, and the anti-idiotype antibody or antigen-binding fragment thereof.

In other embodiments, the sample is added to a tube containing a dried-down anti-idiotype antibody or antigen-binding fragment thereof. In some embodiments, the anti-idiotype antibody or antigen-binding fragment thereof is conjugated to a detectable label, e.g., a fluorescent tag. In some embodiments, the tube further contains other dried-down reagents, e.g., other labelled antibodies, dyes, or lysing agents. In some embodiments, the tube is vortexed for mixing and/or rehydration of the dried-down reagents. In some embodiments, the sample after mixing is placed inside the sample composition chamber. In some embodiments, the microfluidic cartridge is inserted into the cartridge handling unit.

In some embodiments, the cartridge handling unit flows individual cells of the sample through the reading zone. In some embodiments, the cartridge handling unit measures fluorescent signals from the anti-idiotype antibody or antigen-binding fragment thereof bound to the target antibody, e.g. CAR. In some embodiments, the fluorescent signals are measured using an optoelectronic unit. In some embodiments, the fluorescent signals are analyzed using spectral analysis.

In some embodiments, the target antibody or antigen-binding fragment is bound to a cell or expressed on the surface of a cell. In particular embodiments, target antibody, e.g., the CAR is not bound or contained within a cell, for example, in some embodiments, the target antibody is secreted. In certain embodiments, the antibody has been detached, removed, and/or lysed from the surface of a cell.

In some embodiments, the target antibody or antigen-binding fragment is contained in a chimeric antigen receptor (CAR), such as a CAR expressed on the surface of a cell. In some embodiments, the cell is a stem cell, e.g., an iPSC, or an immune cell. In some embodiments, the immune cell is a T cell, e.g., a CD4+ T cell, a CD8+ T cell, naïve T ($T_N$) cell, effector T cell ($T_{EFF}$), memory T cell, tumor-infiltrating lymphocyte (TIL), immature T cell, mature T cell, helper T cells, cytotoxic T cell, mucosa-associated invariant T (MAIT) cell, naturally occurring and adaptive regulatory T (Treg) cell, helper T cell, such as a TH1 cell, TH2 cell, TH3 cell, TH17 cell, TH9 cell, TH22 cell, follicular helper T cell, alpha/beta T cell, and/or a delta/gamma T cells. In some embodiments, the cell is from a tissue, e.g., heart, vasculature, salivary glands, esophagus, stomach, liver, gallbladder, pancreas, intestines, colon, rectum, hypothalamus, pituitary gland, pineal gland, thyroid, parathyroid, adrenal gland, kidney, ureter, bladder, urethra, lymphatic system, skin, muscle, brain, spinal cord, nerves, ovaries, uterus, testes, prostate, pharynx, larynx, trachea, bronchi, lungs, diaphragm, bone, cartilage, ligaments, or tendons.

In some of any such embodiments, the target antibody is an anti-GPRC5D antibody. In some of any such embodiments, the anti-GPRC5D antibody is the target anti-GPRC5D antibody, e.g., as described in section I.

In some of any such embodiments, the anti-idiotype antibody or antigen-binding fragment thereof is an anti-idiotype antibody or antigen-binding fragment thereof that binds to or recognizes the target anti-GPRC5D antibody, such as any such anti-idiotype antibody or antigen-binding fragment thereof as described herein, e.g., in Section I.

B. Use in Cell Stimulation

In some embodiments, the provided anti-idiotype antibodies or antigen-binding fragments thereof are agonists and/or exhibit specific activity to stimulate cells expressing a target antibody including conjugates or chimeric receptors containing the same, such as an anti-GPRC5D antibody (e.g., the target anti-GPRC5D antibody), or an antigen-binding fragment thereof. In some embodiments, provided are methods involving use of the provided anti-idiotype antibodies, and molecules (such as conjugates and complexes) containing one or more of such anti-idiotype antibodies, for stimulation or activation of CAR-expressing or other chimeric receptor-expressing cells, such as T cells. In some aspects, the CAR or other receptor comprises the target antibody, such as an anti-GPRC5D antibody (e.g., the target anti-GPRC5D antibody), or an antigen-binding fragment thereof.

In some embodiments, the methods can be used in connection with methods of preparing genetically engineered T cells, such as in methods of expanding genetically engineered T cells or other cells into which a nucleic acid molecule encoding the chimeric receptor such as the CAR comprising the target antibody has been introduced, e.g., by transfection, transduction, or a non-viral means of nucleic acid transfer, such as transposon-based approaches. In some aspects, the target antibody is an anti-GPRC5D antibody (e.g., the target anti-GPRC5D antibody), or an antigen-binding fragment thereof. In particular embodiments, the target antibody is or contains a CAR, e.g., an anti-GPRC5D CAR. In particular embodiments, the anti-GPRC5D CAR contains an scFv that is from and/or is derived from an anti-GPRC5D antibody, such as the target anti-GPRC5D antibody.

The methods in some embodiments include incubating a sample comprising T cells transduced with a CAR with the anti-idiotype antibody. In certain embodiments, the methods further include detecting whether the CAR T cells are activated or stimulated, such as by assessing the viability, proliferation, and/or expression of activation markers in the CAR T cells. In some embodiments, the target antibody is an anti-GPRC5D antibody. In some embodiments, the target antibody is or is derived from the target anti-GPRC5D antibody, or an antigen-binding fragment thereof.

In some embodiments, there is provided a method of simulating cells, comprising incubating an input composition comprising cells expressing a CAR comprising a target antibody, such as the target anti-GPRC5D antibody, or an antigen-binding fragment thereof, with an anti-idiotype antibody or antigen-binding fragment thereof described herein that binds to or recognizes the target antibody, thereby generating an output composition comprising stimulated cells. In some embodiments, the incubation is performed under conditions in which the anti-idiotype antibody or antigen-binding fragment thereof binds to the CAR, thereby inducing or modulating a signal in one or more cells in the input composition. In some embodiments, the cells comprise T cells. In some embodiments, the T cells comprise CD4+ and/or CD8+ T cells.

In some embodiments, provided herein is a method of stimulating or expanding cells that express a CAR, by incubating an input composition containing cells expressing a CAR with an anti-ID antibody that binds to and/or recognizes the CAR. In some embodiments, binding between the anti-ID antibody and the CAR induces expansion of the cells expressing the CAR, thereby producing an output composition comprising expanded cells.

In some embodiments, provided herein is a method of purifying an anti-idiotype antibody or antigen-binding fragment thereof, comprising: (a) contacting a composition comprising a target antibody or antigen-binding fragment thereof with an anti-idiotype antibody or antigen-binding fragment thereof provided herein, or an immunoconjugate as provided herein, that binds to or recognizes the target antibody or antigen-binding fragment thereof, and (b) isolating complexes comprising the anti-idiotype antibody or antigen-binding fragment thereof. In some embodiments, the complexes comprising the anti-idiotype antibody or antigen-binding fragment thereof are isolated by affinity-based separation. In some embodiments, the affinity-based separation is immunoaffinity-based separation. In some of any such embodiments, the affinity-based separation is magnetic-based separation. In some of any such embodiments, the affinity-based separation is affinity chromatography.

In some embodiments, anti-idiotype antibody is contacted to or incubated with an input composition of one or more cells to generate an output composition. In certain embodiments, the input cells and/or the input composition is a composition and/or a plurality of cells that are, or are desired to be, treated, incubated, or contacted under conditions that will produce one or more changes to at least a portion of the cells of the input composition, thereby converting the input composition into an output composition. In some embodiments, the input cells are a composition of immune cells, for example, a composition of T cells that contain cells expressing a CAR. In particular embodiments, at least a portion of the cells in the input composition are activated, expanded, and/or enriched in the generated output composition by practice of the provided methods.

In certain embodiments, the anti-idiotype antibody expands or enriches the CAR expressing cells of an input composition. In some embodiments, the input composition comprises eukaryotic cells, such as mammalian cells. In certain embodiments, the input composition contains human cells. In some embodiments, the input composition contains cells that are derived from the blood, bone marrow, lymph, or lymphoid organs. In particular embodiments, the input composition contains cells of the immune system, i.e., cells of innate or adaptive immunity, e.g., myeloid or lymphoid cells, including lymphocytes, typically T cells and/or NK cells. In some embodiments, the input composition contains stem cells, such as multipotent and pluripotent stem cells, including induced pluripotent stem cells (iPSCs). In particular embodiments, the input composition contains $CD3^+$ cells. In certain embodiments, the input composition contains $CD4^+$ cells. In some embodiments, the input composition contains $CD8^+$ cells. In some embodiments, the input composition is a composition of CD4+ cells. In particular embodiments, the input composition is a composition of CD8+ cells.

In some embodiments, the methods and agents are capable of stimulating T cells deficient in or that have downregulated one or more natural signaling molecules such as one or more costimulatory receptors or antigen receptors or cytokine receptors but that express the chimeric receptor, e.g., the CAR, recognized by the anti-Id antibody. In some embodiments, cells of the input composition are low or negative for surface expression of CD28 or other costimulatory molecule or other signaling molecule. Thus in some embodiments, the provided agents and methods have certain advantages compared to certain other activation or stimulatory agents or methods that which may require or depend upon surface expression of CD28 or other endogenous signaling molecule, to provide the desired signal and/or the full extent of such signal, e.g., to provide costimulatory signal and/or to achieve full activation/In some embodiments, the provided agents and methods are advantageous in such regards compared to anti-CD3/anti-CD28 reagents (e.g. beads); in some aspects, the provided anti-ID antibodies are advantageous in being able to stimulate or achieve a desired effect such as activation or proliferation of cells that are low or negative for CD28 or other natural signaling molecule. In some aspects, signaling through the CAR by stimulation with an anti-ID antibody results in both a primary and secondary (costimulatory) signal via the CAR using only the single reagent. In some embodiments, the input composition comprises CD3+ cells that express low levels of CD28 or other endogenous signaling molecule. In some embodiments, the input composition comprises CD3+ cells that are CD28 negative or are negative for other endogenous signaling molecule. In some embodiments, the anti-ID antibody stimulates activation and/or expansion of cells expressing low levels of CD28 or cells that are CD28 negative. In some embodiments, the cells are contacted with anti-idiotype antibody or antigen-binding fragment that is immobilized or bound to a solid support. In some embodiments, the solid support is a bead. In some embodiments, the solid support is the surface of a well or plate, e.g., a cell culture plate. In some examples, the anti-ID antibody is soluble. In certain embodiments, the cells are not contacted with anti-CD3/anti-CD28 conjugated reagents prior to contacting the cells with the anti-idiotype antibody or antigen-binding fragment.

In certain embodiments, the anti-idiotype antibody is applied to, contacted to, or incubated with an input composition of cells that have been transduced or transfected with a nucleotide encoding a CAR. In particular embodiments, incubating, treating, and/or contacting input cells with the anti-idiotype antibody results in an expansion and/or enrichment of cells expressing the CAR. In particular embodiments, incubating, treating, and/or contacting input cells with the anti-idiotype antibody does not result in an expansion and/or enrichment of cells that do not express the CAR. In particular embodiments, incubating, treating, and/or contacting input cells with the anti-idiotype antibody results in an expansion and/or enrichment of cells that do not express the CAR that is at least 50%, at least 75%, at least 85%, at least 90%, at least 95%, at least 99%, at least 99.9% or at least 99.99% less than the expansion and/or enrichment of cells that express the CAR. In some embodiments, the anti-idiotype antibodies provided herein are used to expand CAR expressing cells of an input composition that experienced a low transduction and/or transfection efficiency, and/or that contains a low amount CAR expressing cells. In certain embodiments, the anti-idiotype antibody selectively expands and/or enriches cells that express a CAR.

Some embodiments contemplate that the anti-idiotype antibody is more effective for expanding and/or enriching cells of an input composition with a low transduction or transfection efficiency and/or have a low amount of cells that express the CAR than by expanding and/or enriching the cells by polyclonal stimulation, e.g., anti-CD3 and/or anti-CD28 antibody stimulation. In particular embodiments, polyclonal stimulation results in expansion of cells that express and cells that do not express the CAR in the input composition, and therefore, in some embodiments, may fail to enrich CAR expressing cells, particular when the input composition has a low number of CAR expressing cells. In contrast, in some embodiments, incubation with an anti-idiotype antibody results in a selective expansion of CAR expressing cells and will therefore, in certain embodiments, result in selective expansion and/or enrichment of the CAR expressing cells. In some embodiments, incubating, contacting, and/or treating input cells with the anti-idiotype antibody results in a greater enrichment and/or expansion of CAR expressing cells than by polyclonal stimulation.

In particular embodiments, the anti-idiotype antibody is incubated with, applied to, and/or contacted with input cells that were transfected and/or transduced with a lower amount of viral particles, ratio of copies of the viral vector particles to cells, and/or infectious units (IU), than input cells that are expanded and/or enriched by polyclonal stimulation. For example, in some embodiments, the input composition that is incubated with the anti-idiotype antibody is generated from cells that were transduced with or with at least 0.5, 1, 2, 3, 4, 5, 10, 15, 20, 30, 40, 50, or 60 fewer IU per cell than the input composition that is expanded and/or enriched by polyclonal stimulation. In some embodiments, the input composition that is incubated with the anti-idiotype antibody is generated from cells that were transduced with a titer of viral vector particles with or with at least $1 \times 10^5$ IU/mL, $5 \times 10^5$ IU/mL, $1 \times 10^6$ IU/mL, $5 \times 10^6$ IU/mL, $6 \times 10^6$ IU/mL, $7 \times 10^6$ IU/mL, $8 \times 10^6$ IU/mL, $9 \times 10^6$ IU/mL, or $1 \times 10^7$ IU/mL less than the input composition that is expanded and/or enriched by polyclonal stimulation.

In particular embodiments, transducing cells with a high IU/cell will lead to high transduction efficiency but, in some embodiments, may also lead to transfected cells with a high vector copy number (VCN), which can present safety risks and may not meet regulatory standards. In particular embodiments, lowering the IU/cell that cells are transduced with will reduce transduction efficiency but will lower VCN. In particular embodiments, increasing the IU/cell that cells are transduced with will increase transduction efficiency but will also increase VCN.

In some embodiments, an input composition contains a population of cells that have been transduced or transfected, or cells that are derived from cells that have been transduced or transfected, with one or more nucleic acids encoding a CAR, that is bound by or recognized by the anti-idiotype antibody. In some embodiments, the input composition contains less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, or less than 1% of the cells are CAR expressing cells. In particular embodiments, the cells from the input composition have been transfected or transduced as described in Section II. In certain embodiments, the input cells contains a population of cells that have been transduced or transfected, or cells that are derived from cells that have been transduced or transfected, with one or more nucleic acids encoding an anti-GPRC5D CAR, such as an anti-GPRC5D CAR that contains an scFv that is from and/or is derived from an anti-GPRC5D antibody such as the target anti-GPRC5D antibody.

In particular embodiments, the incubation, contacting, or treatment of cells from the input composition with the anti-idiotype antibody is performed under conditions for stimulation, expansion, and/or activation of cells which conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the cells of the input composition have been transfected or transduced with one nucleic acid comprising a gene encoding a CAR and the cells are contacted, incubated, or treated with the anti-idiotype antibody that binds to or recognizes the recombinant receptor. In some embodiments, the cells of the input composition are treated, incubated, or contacted with the anti-idiotype antibody after the cells transduced or transfected nucleic acid encoding a CAR. In particular embodiments, the cells of the input composition are treated, incubated, or contacted with the anti-idiotype antibody immediately, within about 1 minute, within about 5 minutes, within about 30 minutes, within about 1 hour, within about 2 hours, within about 4 hours, within about 6 hours, within about 8 hours, within about 12 hours, within about 24 hours, within about 2 days, within about 3 days, within about 4 days, within about 5 days, within about 6 days, within about 1 week, within about 2 weeks, within about 3 weeks, within about 4 weeks, within about 5 weeks, or within about 6 weeks after the cells of the input composition have been transduced or transfected.

In some embodiments, cells of the input composition are treated, incubated, and/or contacted with soluble anti-idiotype antibody, contacted with an antibody that is not cross-linked and/or contacted with an antibody that is not bound or attached to a solid support.

In some embodiments, the methods result in proliferation, activation, stimulation, cytokine release, or other functional outcome such as upregulation of an activation marker or cytokine release or production, of cells expressing the chimeric receptor such as the CAR recognized by the anti-Id antibody. In some aspects, such proliferation or other functional response or readout is induced in such cells to a degree that is similar to or greater than that induced by incubation of the cells with an agent and/or conditions that stimulates proliferation of T cells, such as anti-CD3/CD28 beads and/or crosslinked anti-CD3. In some aspects, the methods do not involve crosslinking of the anti-idiotype antibody. In some aspects of any of the embodiments, the anti-idiotype agents are capable of inducing the specified proliferation or functional outcome or degree thereof, without crosslinking of the anti-idiotype antibody. In some aspects, anti-idiotype agents herein are advantageous in their ability to stimulate or cause a particular functional outcome of T cells or other immune cells expressing the target receptor, without the need to crosslink the anti-Id antibody or use a secondary agent. In some aspects, the result is achieved with soluble or plate-bound form of the anti-idiotype antibody. In some aspects, the result is achieved with the anti-idiotype antibody coupled to a bead.

In particular embodiments, the cells of the input composition are treated, incubated, and/or contacted with between 10 pg/ml and 100 μg/ml, between 1 pg/ml and 1 ng/ml, between 1 ng/ml and 1 pg/l between 100 ng/ml and 1.0 pg/ml, between 1 ng/ml and 100 ng/ml, between 10 ng/ml and 1.0 pg/ml, between 100 ng/ml and 10 pg/ml, between 250 ng/ml and 10 μg/ml, between 250 pg/ml and 1 ng/ml, between 1 μg/ml and 10 μg/ml, between 250 ng and about 2.5 pg/ml, or between 1 μg/ml and 10 μg/ml.

In some embodiments, the anti-idiotype antibody or antigen-binding fragment thereof is immobilized to a solid support, which optionally comprises or is conjugated to a reagent comprising a plurality of binding sites capable of reversibly binding to the anti-idiotype antibody or antigen-binding fragment thereof. In some embodiments, the solid support is a surface of a plate or a well. In some embodiments, the anti-idiotype antibody or antigen-binding fragment thereof is immobilized to a soluble reagent, which optionally is or comprises a plurality of binding sites capable of reversibly binding to the anti-idiotype antibody or antigen-binding fragment thereof. In some embodiments, the reagent comprises a streptavidin mutein. In one exemplary embodiment, the anti-idiotypic antibody comprises a streptavidin-binding peptide or other streptavidin binding moiety capable of binding to a streptavidin or streptavidin mutein molecule present on or immobilized on the soluble reagent, which, in some cases, can be dissociated in the presence of a competition substance, such as biotin. Exemplary of such systems include those described in PCT published patent application No. WO2015/158868.

In particular embodiments, the cells of the input composition are treated, incubated, and/or contacted with anti-idiotype antibody that is attached, bound, coated, and/or conjugated to a solid surface or support, e.g., a plate or a well. In certain embodiments, the anti-idiotype antibody has been attached, bound, coated, and/or conjugated to the solid surface or support by incubating the solid surface or support with a concentration of the anti-idiotype antibody. In particular embodiments, the solid surface or support is incubated with between 10 ng/ml and 100 μg/ml, between 100 ng/ml and 1.0 pg/ml, between 250 ng/ml and 10 μg/ml, between 250 ng/ml and 1 pg/ml, between 1 μg/ml and 10 μg/ml, between 250 ng and 2.5 pg/ml, or between 1 μg/ml and 10 μg/ml the anti-idiotype antibody. In some embodiments, the solid surface or support is incubated with between 250 ng/ml and 10 μg/ml. In certain embodiments, the solid surface or support is incubated with or with about 0.25 pg/ml, 0.5 pg/ml, 1.0 pg/ml, 1.25 pg/ml, 2 μg/ml, 2.5 μg/ml, 5 μg/ml or 10 μg/ml the anti-idiotype antibody.

In some embodiments, the incubation is for at least or about at least 5 minutes, 10 minutes, 30 minutes, 60 minutes, 2 hours, 6 hours, 12 hours, 24 hours, 36, 48 hours, 72 hours or 96 hours. In some embodiments, the input composition comprises less than or less than about 60%, less than or less than about 50%, less than or less than about 40%, less than or less than about 30%, less than or less than about 20% or less than or less than about 10% CAR-expressing cells as a percentage of the total cells in the composition. In some embodiments, the number of CAR-expressing cells in the output composition is increased by greater than 1.2-fold, 1.5-fold, 2.0-fold, 3.0-fold, 4.0-fold, 5.0-fold, 10-fold or more compared to the number of CAR-expressing cells in the input composition; and/or the percentage of CAR-expressing in the output composition compared to the total cells in the composition is increased by greater than 10%, 20%, 40%, 50%, 60%, 70%, 80% or more. In some embodiments, prior to incubating, the cells are not selected or enriched for CAR-expressing cells.

In certain embodiments, the anti-idiotype antibody are contacted or incubated with cells from the input composition, e.g. comprising cells that express a CAR, for an amount of time to expand one or more cells of the input composition, such as to expand cells of the input composition that express the recombinant receptor. In particular embodiments, the cells from the input composition are contacted, incubated, or treated with the anti-idiotype antibody for at least about 12 hours, at least about 24 hours, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, or at least about 4 weeks. In particular embodiments, the cells from the input composition are contacted, incubated, or treated with the anti-idiotype antibody for less than about 1 day, less than about 2 days, less than about 3 days, less than about 4 days, less than about 5 days, less than about 6 days, or less than or about 12 days. In some embodiments, the cells from the input composition are contacted, incubated, or treated with the anti-idiotype antibody for between about 1 day and about 14 days, between about 3 days, and 7 days, or for between 4 days and 6 days.

In particular embodiments, cells from an input composition, e.g. comprising cells that express a CAR, are incubated, contacted, or treated with anti-idiotype antibody at temperatures greater than room temperature to expand the cells of the input composition that express the recombinant receptor. In some embodiments, the treatment, incubation, or contacting is performed at a temperature greater than about 25° C., such as generally greater than or greater than about 32° C., 35° C. or 37° C. In some embodiments, the treatment, contacting, or incubation is performed at a temperature of at or about 37° C.±2° C., such as at a temperature of at or about 37° C.

In some embodiments, at least 50%, at least 55%, at least 60%, at least 65%, at least 70%, at least 75%, at least 80%, at least 85%, at least 90%, at least 95%, at least 97%, at least 99%, at least 99.9%, about 100%, or 100% of the cells of the output composition express the CAR.

In particular embodiments, the number of cells that express the CAR in the output composition that was incubated, treated, and/or contacted with the anti-idiotype antibody is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, at least 100%, at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold greater than the number of cells that express the CAR in the input composition.

In particular embodiments, the percentage of cells that express the CAR in the output composition that was incubated, treated, and/or contacted with the anti-idiotype antibody is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, at least 100%, at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold greater than the number of cells that express the CAR in the input composition.

In some embodiments, the number of cells that express the CAR in the output composition that was incubated, treated, and/or contacted with the anti-idiotype antibody is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, at least 100%, at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold greater than the number of cells of an output composition that received polyclonal stimulation, incubation with anti-CD3 and anti-CD28 antibodies.

In certain embodiments, the percentage of cells that express the CAR in the output composition that was incubated, treated, and/or contacted with the anti-idiotype antibody is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, at least 100%, at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold greater than the number of cells of an output composition that received polyclonal stimulation, incubation with anti-CD3 and anti-CD28 antibodies.

In some embodiments, the cells that express the CAR in the output composition that was incubated, treated, and/or contacted with the anti-idiotype antibody contain at least a 1%, at least a 5%, at least a 10%, at least a 15%, at least a 20%, at least a 25%, at least a 30%, at least a 35%, at least a 40%, at least a 45%, at least a 50%, at least a 55%, at least a 60%, at least a 65%, at least 70%, at least 75%, at least 80%, at least 85%, at least 95%, or at least a 99% lower VCN than cells of an output composition that received polyclonal stimulation, e.g., incubation with anti-CD3 and anti-CD28 antibodies. In some embodiments, the average VCN of CAR expressing cells of the output no more than at or about 10, 5, 4, 2.5, 1.5, or 1.

In some embodiments, such methods can be used as part of the manufacturing, analytic, and/or quality control methods, e.g., in association with the generation of cell therapies expressing recombinant polypeptides containing an antibody or fragment thereof recognized by the anti-idiotype antibody, such as the CAR T cells, for testing purpose, including to test expression and/or potency of the engineered receptor, e.g., in cells engineered for use in therapy in an individual. In certain embodiments, the cell compositions may be tested at any stage in the process of generating CAR expressing T cells. In particular embodiments, a sample of cells may be collected from a cell composition at any stage of the process and stored, e.g., by cryofreezing and/or cryopreservation, for later testing and/or analysis. The compositions tested may be pharmaceutical compositions e.g., including those containing the cells and a pharmaceutically acceptable recipient and/or cryopreservative agent.

In some embodiments, the anti-idiotype antibody stimulates cells expressing a target antibody, e.g., a CAR, in vivo. Particular embodiments contemplate that CAR-T cell therapies are effective in the treatment of cancer and other diseases and disorders. However, in certain contexts, available approaches to CAR-T cell therapy may not always be entirely satisfactory. For example, in some embodiments, the exposure and persistence of CAR expressing cells in the subject is reduced or declines over time. Yet, observations indicate that, in some cases, increased exposure of the CAR expressing cells may improve efficacy and therapeutic outcomes in CAR-T cell therapy. Thus, in some embodiments, the anti-idiotype antibody is administered to boost, augment and/or increase persistence and/or expansion of CAR expressing cells.

In certain embodiments, the anti-idiotype antibody is administered to a subject, such as a subject who has previously been administered a therapeutic cell composition containing CAR expressing cells. In some embodiments, administering the anti-idiotype antibody to a subject promotes re-expansion of the CAR expressing cells in the subject, which, in some cases, may reach or exceed the initial peak level of expansion prior to the administration of the anti-idiotype antibody. In some embodiments, the anti-idiotype antibody is administered to modulate expansion and/or persistence of the CAR expressing cells at times when the levels of the CAR expressing cells have declined or are not detectable. In some embodiments, CAR expressing cells that re re-expanded by the anti-idiotype antibody exhibit increased potency in a subject to which it is administered, for example, as compared to the potency prior to administration of the anti-idiotype antibody.

In certain embodiments, administration of the anti-idiotype antibody increases or enhances persistence of the CAR expressing cells in the subject. In some embodiments, the CAR expressing cells are detectable in the subject at or at least 7 days, 14 days, 21 days, 28 days, 35 days, 42 days, 49 days, 56 days, 63 days, 2 months, 3 months, 4 months, 5 months, 6 months, or more than 6 months following the administration of the anti-idiotype antibody. In some aspects, increased exposure of the subject to the cells includes expansion and/or increased expansion of the cells.

In some embodiments, the CAR-expressing cells expand in the subject following administration of the anti-idiotype antibody. In particular embodiments, administering the anti-idiotype antibody results in a maximum concentration in the blood or serum or other bodily fluid or organ or tissue of the subject, of at least 100, 500, 1000, 1500, 2000, 5000, 10,000 or 15,000 copies of a nucleic acid encoding the CAR per microgram of DNA, or at least 0.1, 0.2, 0.3, 0.4, 0.5, 0.6, 0.7, 0.8, or 0.9 CAR-expressing cells per microliter. In some embodiments, the cells expressing the CAR are detected as at least 10, 20, 30, 40, 50, or 60% of total PBMCs in the blood of the subject, and/or at such a level for at least 1, 2, 3, 4, 5, 6, 7, 8, 9, 10, 11, 12, 24, 36, 48, or 52 weeks following the administration of the anti-idiotype antibody or for 1, 2, 3, 4, or 5, or more years following administration of the anti-idiotype antibody. In some aspects, administering the anti-idiotype antibody results in at least a 2-fold, at least a 4-fold, at least a 10-fold, or at least a 20-fold increase in copies of nucleic acid encoding the recombinant receptor, e.g., CAR, per microgram of DNA, e.g., in the serum, plasma, blood or tissue, e.g., tumor sample, of the subject. In particular embodiments, administering the anti-idiotype antibody results in at least a 2-fold, at least a 4-fold, at least a 10-fold, or at least a 20-fold increase in the number of circulating CAR expressing cells in the subject.

In some aspects, at least about $1\times10^2$, at least about $1\times10^3$, at least about $1\times10^4$, at least about $1\times10^5$, or at least about $1\times10^6$ or at least about $5\times10^6$ or at least about $1\times10^7$ or at least about $5\times10^7$ or at least about $1\times10^8$ CAR-expressing cells and/or at least 10, 25, 50, 100, 200, 300, 400, or 500, or 1000 CAR expressing cells per microliter, e.g., at least 10 per microliter, are detectable or are present in the subject or fluid, plasma, serum, tissue, or compartment thereof, such as in the blood, e.g., peripheral blood, or disease site following administration of the anti-idiotype antibody. In some embodiments, such a number or concentration of cells is detectable in the subject for at least about 20 days, at least about 40 days, or at least about 60 days, or at least about 3, 4, 5, 6, 7, 8, 9, 10, 11, or 12 months, or at least 2 or 3 years, following administration of the anti-idiotype antibody.

Various delivery systems are known and can be used to administer the anti-idiotype antibody. In certain embodiments, the anti-idiotype antibody is administered by encapsulation in and/or attachment to liposomes, microparticles, and microcapsules. Methods of administering the anti-idiotype antibody include but are not limited to intradermal, intramuscular, intraperitoneal, intravenous, subcutaneous, intranasal, epidural, and oral routes. The anti-idiotype antibody may be administered by any convenient route, for example by infusion, by bolus injection, by absorption through epithelial or mucocutaneous linings (e.g., oral, rectal and intestinal mucosa, etc.), and may be administered together with other biologically active agents. Administration can be systemic or local. Pulmonary administration can also be employed, e.g., by use of an inhaler or nebulizer, and formulation with an aerosolizing agent. In certain embodiments, the anti-idiotype antibody is delivered in a vesicle, in particular a liposome (Langer, 1990, Science 249:1527-1533), for example a cationic liposome (WO 98140052).

In some embodiments, there is provided a method of producing a cell composition, comprising introducing into cells a nucleic acid molecule encoding a CAR, thereby generating an input composition, and incubating the input composition with an anti-idiotype antibody or antigen-binding fragment thereof that binds to or recognizes the antigen-binding domain of the CAR, thereby producing the cell composition. In some embodiments, the anti-idiotype antibody or antigen-binding fragment thereof is an immunoconjugate as provided herein that includes the anti-idiotype antibody or antigen-binding fragment thereof. In some embodiments, the CAR comprises a target antibody or antigen-binding fragment thereof that binds to or recognizes GPRC5D. In some embodiments, the target antibody is the target anti-GPRC5D antibody, or an antigen-binding fragment thereof. In some embodiments, the anti-idiotype antibody or antigen-binding fragment thereof is an anti-idiotype antibody or antigen-binding fragment thereof described herein. In some embodiments, the anti-idiotype antibody or antigen-binding fragment thereof is an agonist of the CAR. In some embodiments, the anti-idiotype antibody or antigen-binding fragment thereof is an antagonist of the CAR. In some embodiments, the introducing comprises introducing the nucleic acid molecule into the cells by viral transduction, transposition, electroporation, or chemical transfection. In some embodiments, the introducing comprises introducing the nucleic acid molecule in the cells by transduction with a retroviral vector comprising the nucleic acid molecule, by transduction with a lentiviral vector comprising the nucleic acid molecule, by transposition with a transposon comprising the nucleic acid molecule, or by electroporation or transfection of a vector comprising the nucleic acid molecule.

In some embodiments, the method further comprises a step of stimulating or activating the cells prior to introducing the nucleic acid molecule encoding the CAR. In some embodiments, activating the cells comprises contacting the cells with an agonist of CD3 and optionally an agonist of CD28. In some embodiments, activating the cells comprising contacting the cells with a reagent comprising agonistic anti-CD3 and anti-CD28 antibodies. In some such embodiments, during at least a portion of the contacting with an anti-CD3/anti-CD28 and/or during at least a portion of introducing the nucleic acid encoding the CAR, the method includes incubating or contacting the cells with the anti-idiotypic antibody or antigen-binding In some embodiments, the incubation is performed under conditions in which the anti-idiotype antibody or antigen-binding fragment thereof binds to the CAR, thereby inducing or modulating a signal in one or more cells in the input composition. In some embodiments, the cells comprise T cells.

In some such embodiments, the T cells comprise CD4+ and/or CD8+ T cells. In some embodiments, the anti-idiotype antibody or antigen-binding fragment thereof is immobilized to a solid support, which optionally comprises or is conjugated to a reagent comprising a plurality of binding sites capable of reversibly binding to the anti-idiotype antibody or antigen-binding fragment thereof. In some embodiments, the anti-idiotype antibody or antigen-binding fragment thereof is immobilized to a soluble reagent, which optionally is or comprises a plurality of binding sites capable of reversibly binding to the anti-idiotype antibody or antigen-binding fragment thereof. In some embodiments, the reagent comprises a streptavidin mutein. In one exemplary embodiment, the anti-idiotypic antibody comprises a streptavidin-binding peptide or other streptavidin binding moiety capable of binding to a streptavidin or streptavidin mutein molecule present on or immobilized on the soluble reagent, which, in some cases, can be dissociated in the presence of a competition substance, such as biotin. Exemplary of such systems include those described in PCT published patent application No. WO2015/158868. In some embodiments, the incubation is for at least or about at least 5 minutes, 10 minutes, 30 minutes, 60 minutes, 2 hours, 6 hours, 12 hours, 24 hours, 36, 48 hours, 72 hours or 96 hours. In some embodiments, the input composition comprises less than or less than about 60%, less than or less than about 50%, less than or less than about 40%, less than or less than about 30%, less than or less than about 20% or less than or less than about 10% CAR-expressing cells as a percentage of the total cells in the composition. In some embodiments, the number of CAR-expressing cells in the output composition is increased by greater than 1.2-fold, 1.5-fold, 2.0-fold, 3.0-fold, 4.0-fold, 5.0-fold, 10-fold or more compared to the number of CAR-expressing cells in the input composition; and/or the percentage of CAR-expressing in the output composition compared to the total cells in the composition is increased by greater than 10%, 20%, 40%, 50%, 60%, 70%, 80% or more. In some embodiments, prior to incubating, the cells are not selected or enriched for CAR-expressing cells.

In some embodiments, there is provided a method of monitoring activity of a CAR comprising a target antibody, such as the target anti-GPRC5D antibody, or an antigen-binding fragment thereof, including the steps of incubating a sample comprising T cells transduced with the CAR with an agonistic anti-idiotype antibody or antigen-binding fragment thereof that targets or binds the CAR; and/or determining the presence, absence or amount of activation, stimulation and/or expansion of the CAR T cells, thereby monitoring the activity of the CAR-T cells. In some embodiments, such methods can be used for validating the CAR, in which case the method can include c) validating the CAR based on the level of activation, stimulation and/or expansion of CAR-T cells.

In some embodiments, activation, stimulation and/or expansion of CAR T cells is assessed by determining the viability, proliferation, and/or expression of T cell activation markers in the CAR T cells following a period of incubation with the anti-idiotype antibody. In some embodiments, viability of CAR T cells is assessed by calculating the percent of living versus total T cells transduced with the CAR following incubation with the anti-idiotype antibody. In some embodiments, proliferation of CAR T cells is assessed by dye dilution of a dye used to stain the CAR T cells prior to incubation with the anti-idiotype antibody. In some embodiments, expression of T cell activation markers is assessed by flow cytometry with staining for antibodies recognizing the T cell activation markers. In some embodiments, the T cell activation markers are selected from the group consisting of CD25, CD26, CD27, CD28, CD30, CD69, CD71, CD134, CD137, and CD154. In some embodiments, the period of incubation is from about 1 to about 10 days (such as about any of 1, 2, 3, 4, 5, 6, 7, 8, 9, or 10 days, including any ranges between these values).

In some embodiments, there is provided a method of monitoring a preparation of CAR T cells, wherein the CAR comprises a target antibody, such as the target anti-GPRC5D antibody, or an antigen-binding fragment thereof, comprising a) incubating a portion of the preparation with an agonistic anti-idiotype antibody or antigen-binding fragment thereof that targets or binds the CAR; and b) determining the presence, absence or amount of activation, stimulation and/or expansion of the CAR T cells. In some embodiments, the preparation of CAR-T cells can be cells produced or manufactured under particular conditions desirable to be tested. In some embodiments, the monitoring is carried out in connection with a release assay, such as for validating the cells prior to administration to a subject. In some aspects, the method further includes c) validating the preparation based on the level of activation of the CAR T cells. In some embodiments, activation of CAR T cells in the preparation is assessed by determining the viability, proliferation, and/or expression of T cell activation markers in the CAR T cells following a period of incubation with the anti-idiotype antibody. In some embodiments, viability of CAR T cells is assessed by calculating the percent of living versus total T cells transduced with the CAR following incubation with the anti-idiotype antibody. In some embodiments, proliferation of CAR T cells is assessed by dye dilution of a dye used to stain the CAR T cells prior to incubation with the anti-idiotype antibody. In some embodiments, expression of T cell activation markers is assessed by flow cytometry with staining for antibodies recognizing the T cell activation markers. In some embodiments, the T cell activation markers are selected from the group consisting of CD25, CD26, CD27, CD28, CD30, CD69, CD71, CD134, CD137, and CD154. In some embodiments, the period of incubation is from about 1 to about 10 days (such as about any of 1, 2, 3, 4, 5, 6, 7, 8, 9, or 10 days, including any ranges between these values).

In some embodiments, the target antibody is an anti-GPRC5D antibody. In some of any such embodiments, the anti-GPRC5D antibody is the target anti-GPRC5D antibody, e.g., as described in Section I.A.

In some of any such embodiments, the anti-idiotype antibody or antigen-binding fragment thereof is an anti-idiotype antibody or antigen-binding fragment thereof that binds to or recognizes the target anti-GPRC5D antibody, such as any such anti-idiotype antibody or antigen-binding fragment thereof as described herein, e.g., in Section I.A.

C. Use in Cell Inactivation/Depletion

In some embodiments, the provided anti-idiotype antibodies or antigen-binding fragments thereof are antagonists and/or exhibit specific activity to inhibit, ablate, and/or deplete (for example, kill via antibody-dependent cell-mediated cytotoxicity, ADCC) cells expressing a target antibody, such as an anti-GPRC5D antibody (e.g., the target anti-GPRC5D antibody), or an antigen-binding fragment thereof. Also provided are methods involving use of the provided anti-idiotype antibodies, and molecules (such as conjugates and complexes) containing one or more of such anti-idiotype antibodies, for inactivation, ablation, and/or depletion of CAR T cells, wherein the CAR comprises a target antibody, such as an anti-GPRC5D antibody (e.g., the target anti-GPRC5D antibody), or an antigen-binding fragment thereof.

The methods in some embodiments include treating, contacting, and/or incubating a composition and/or a sample comprising T cells transduced with a CAR with the anti-idiotype antibody. In certain embodiments, the methods further include detecting whether the CAR T cells are inactivated, such as by assessing the viability, proliferation, and/or expression of activation markers in the CAR T cells. In some embodiments, the methods are in association with a therapy comprising administration of CAR T cells. The methods in some embodiments include administering the anti-idiotype antibody to an individual. In one embodiment, an anti-idiotype antibody or conjugate is used to ablate and/or deplete (such as kill) CAR T cells in an individual. In some embodiments, the target antibody is an anti-GPRC5D antibody. In some embodiments, the target antibody is or is derived from the target anti-GPRC5D antibody, or an antigen-binding fragment thereof.

In some embodiments, the anti-idiotype antibody is administered to deplete, reduce, and/or decrease the number of CAR expressing cells in a subject. In particular embodiments, administration of the anti-idiotype antibody depletes, reduces, and/or decreases the amount of CAR expressing cells, e.g., circulating CAR-T cells, by at least 25%, at least 50%, at least 60%, at least 70%, at least 80%, at least 90%, at least 95%, at least 99%, at least 99.9%, 100% or about 100%. In certain embodiments, the depletion, reduction, and/or decrease is in relation to an amount of CAR expressing cells in the subject prior to the administration of the anti-idiotype antibody. In particular embodiments, the depletion, reduction, and/or decrease is in relation to an amount of CAR expressing cells in a subject that is not administered the anti-idiotype antibody. In some embodiments, CAR expressing cells are not detectable in the subject following administration of the anti-idiotype antibody. In particular embodiments, the anti-idiotype antibody is a human or humanized antibody.

In some embodiments, there is provided a method of inactivating CAR T cells, wherein the CAR comprises a target antibody, such as the target anti-GPRC5D antibody, or an antigen-binding fragment thereof, comprising incubating a sample comprising the CAR T cells with an antagonistic anti-idiotype antibody or antigen-binding fragment thereof targeting the CAR, thereby inactivating the CAR T cells in the sample. In some embodiments, the anti-idiotype antibody is used in an amount sufficient to attenuate the activation of the CAR T cells in the sample. In some embodiments, the anti-idiotype antibody is used in an amount sufficient to substantially inactivate the CAR T cells in the sample. In some embodiments, incubation with the anti-idiotype antibody results in ablation and/or depletion of CAR T cells in the sample. In some embodiments, the anti-idiotype antibody is used in an amount sufficient to result in clearance of the CAR T cells in the sample.

In some embodiments, the anti-idiotype antibody is administered to deplete, reduce, and/or decrease the activity of the CAR and/or the CAR expressing cells in a subject. In particular embodiments, administration of the anti-idiotype antibody reduces and/or decreases stimulation and/or activation of the CAR and/or the CAR expressing cell by at least 25%, at least 50%, at least 60%, at least 70%, at least 80%, at least 90%, at least 95%, at least 99%, at least 99.9%, 100% or about 100%. In certain embodiments, the reduction and/or decrease is in relation to the stimulation and/or activity of the CAR and/or CAR expressing cells in the subject prior to the administration of the anti-idiotype antibody. In particular embodiments, the reduction and/or decrease is in relation to stimulation and/or activity of the CAR and/or CAR expressing cells in a subject that is not administered the anti-idiotype antibody. In some embodiments, the activity and/or stimulation refers to one or more aspects of CAR receptor or CAR T cell activity and may be assessed by any suitable known means, including by any means provided herein. In some embodiments, activity and/or stimulation of the CAR and/or CAR expressing cells are not detectable in the subject following administration of the anti-idiotype antibody. In particular embodiments, the anti-idiotype antibody is a human or humanized antibody.

In some embodiments, the anti-idiotype antibody is administered to prevent, reduce, and/or decrease the binding and/or the ability of the CAR and/or the CAR expressing cells to bind to the antigen. In particular embodiments, administration of the anti-idiotype antibody reduces and/or decreases antigen binding of the CAR and/or the CAR expressing cell by at least 25%, at least 50%, at least 60%, at least 70%, at least 80%, at least 90%, at least 95%, at least 99%, at least 99.9%, 100% or about 100%. In certain embodiments, the reduction and/or decrease is in relation to the antigen binding and/or the ability of the CAR and/or CAR expressing cells to bind to the antigen in the subject prior to the administration of the anti-idiotype antibody. In particular embodiments, the reduction, and/or decrease is in relation to antigen binding and/or the ability to bind the antigen of the CAR and/or CAR expressing cells in a subject that is not administered the anti-idiotype antibody. In particular embodiments, the anti-idiotype antibody is a human or humanized antibody.

In some embodiments, there is provided a method of ablating and/or depleting (such as killing) CAR T cells, wherein the CAR comprises a target antibody, such as the target anti-GPRC5D antibody, or an antigen-binding fragment thereof, comprising incubating a sample comprising the CAR T cells with an anti-idiotype antibody or antigen-binding fragment thereof targeting the CAR, thereby ablating and/or depleting CAR T cells in the sample. In some embodiments, the ablating and/or depleting is by antibody-dependent cell-mediated cytotoxicity (ADCC). In some embodiments, the anti-idiotype antibody is used in an amount sufficient to result in ablation and/or depletion of substantially all of the CAR T cells in the sample.

In some embodiments, there is provided a method of adjusting a CAR T cell therapy in an individual, wherein the CAR comprises a target antibody, such as the target anti-GPRC5D antibody, or an antigen-binding fragment thereof, comprising administering an antagonistic anti-idiotype antibody or antigen-binding fragment thereof targeting the CAR to the individual, thereby inactivating the CAR T cells. In some embodiments, the anti-idiotype antibody is administered in an amount sufficient to attenuate the activation of the CAR T cells in the individual. In some embodiments, the anti-idiotype antibody is administered in an amount sufficient to substantially inactivate the CAR T cells in the individual. In some embodiments, administration of the anti-idiotype antibody results in ablation and/or depletion of CAR T cells in the individual. In some embodiments, the anti-idiotype antibody is administered in an amount sufficient to result in clearance of the CAR T cells in the individual.

In some embodiments, there is provided a method of adjusting a CAR T cell therapy in an individual, wherein the CAR comprises a target antibody, such as the target anti-GPRC5D antibody, or an antigen-binding fragment thereof, comprising administering an anti-idiotype antibody immunoconjugate targeting the CAR to the individual, wherein the anti-idiotype antibody immunoconjugate comprises a cytotoxic agent. In some embodiments, the anti-idiotype antibody immunoconjugate is administered in an amount sufficient to attenuate the CAR T cell therapy in the individual. In some embodiments, the anti-idiotype antibody immunoconjugate is administered in an amount sufficient to substantially stop the CAR T cell therapy in the individual. In some embodiments, the anti-idiotype antibody immunoconjugate is administered in an amount sufficient to result in clearance of the CAR T cells in the individual. In some embodiments, the cytotoxic agent is selected from the group consisting of chemotherapeutic agents or drugs, growth inhibitory agents, toxins (e.g., protein toxins, enzymatically active toxins of bacterial, fungal, plant, or animal origin, or fragments thereof), and radioactive isotopes.

In some embodiments, there is provided a method of depleting cells, comprising administering, to a subject, a composition comprising an anti-idiotype antibody or antigen-binding fragment thereof as provided herein, or an immunoconjugate as provided herein, that binds to or recognizes a target antibody or antigen-binding fragment thereof (e.g., the target anti-GPRC5D antibody), wherein the subject has been administered a cell expressing a CAR comprising the target antibody or antigen-binding fragment thereof. In some embodiments, the depletion occurs via antibody-mediated cytotoxicity (ADCC).

In some embodiments, the target antibody is an anti-GPRC5D antibody. In some of any such embodiments, the anti-GPRC5D antibody is the target anti-GPRC5D antibody, e.g., as described in section I.A.

In some of any such embodiments, the anti-idiotype antibody or antigen-binding fragment thereof is an anti-idiotype antibody or antigen-binding fragment thereof that binds to or recognizes the target anti-GPRC5D antibody, such as any such anti-idiotype antibody or antigen-binding fragment thereof as described herein, e.g., in section I.A.

D. Use in Binding Assay or Method

Provided herein are methods for assessing the presence or absence of a molecule in a sample that binds to a chimeric antigen receptor (CAR), such as the extracellular domain of a CAR or to a portion thereof containing the antigen-binding domain. In some embodiments, the methods can be used to assess the presence or absence of a humoral response or antibody response in a subject to an administered cell therapy comprising a chimeric antigen receptor (CAR). In some embodiments, the chimeric antigen receptor comprises a target antibody that is the target anti-GPRC5D antibody or an antigen-binding fragment thereof. In some embodiments, an anti-idiotype antibody or antigen-binding fragment thereof that binds to or recognizes the extracellular domain of the CAR, such as any described herein, can be used as a positive control in the method.

In particular embodiments, the method includes contacting a sample with an anti-idiotype antibody or antigen-binding fragment thereof that binds to or recognizes the extracellular domain of the CAR at a concentration of between 10 ng/ml and 100 μg/ml, between 100 ng/ml and 1.0 pg/ml, between 250 ng/ml and 10 μg/ml, between 250 ng/ml and 1 pg/ml, between 1 μg/ml and 10 μg/ml, between 250 ng and 2.5 pg/ml, or between 1 μg/ml and 10 μg/ml of the anti-idiotype antibody. In some embodiments, the concentration of the anti-idiotype antibody between 250 ng/ml and 10 μg/ml. In certain embodiments, the concentration of the anti-idiotype antibody is about 0.1 pg/ml, 0.25 pg/ml, 0.5 pg/ml, 1.0 pg/ml, 1.25 pg/ml, 2 μg/ml, 2.5 pg/ml, or 5 μg/ml of the anti-idiotype antibody.

In some aspects, adoptive cell therapy may be associated with development of an immune response in the subject to the cells and/or construct administered. For example, in some cases, exposure to a chimeric receptor may be limited by host immune responses against the recombinant receptors expressed by the administered cells, which may prematurely eliminate the cells. It is observed that even in certain subjects having B cell malignancies, who often are immunocompromised, immune responses can be detected that are specific for regions of receptors expressed by cells administered in adoptive cell therapy. For example, subjects, e.g. human subjects, administered cells genetically engineered with a CAR can develop a specific immune response to an immunogenic region of the chimeric region, including regions that may contain non-human sequences (e.g. murine scFv) and or to a region containing the junction between two domains or portions of the chimeric receptor, e.g. the transmembrane and costimulatory domain of the CAR.

In some embodiments, there are provided methods that involve contacting or incubating a binding reagent with a sample from a subject having been administered a cell therapy comprising cell engineered with a chimeric antigen receptor in which the binding reagent is a protein that includes the extracellular domain of the CAR or a portion thereof containing the target antibody or the antigen-binding fragment thereof. In some embodiments, the methods further include detecting whether a complex is formed between the binding reagent and a molecule, e.g. binding molecule, such as an antibody, present in the sample, and/or detecting the presence or absence or level of such binding. In certain embodiments, the contacting or incubating is under conditions permissive for binding of the binding reagent to a molecule present in the sample from the subject. In certain aspects, the method can be further carried out on a positive control sample containing an anti-idiotypic antibody or antigen-binding fragment thereof that binds to or recognizes the CAR, such as any as described. In some embodiments, determining the presence, absence or level of binding of the molecule to the binding reagent can include comparison of the binding or detection to the binding or detection of the positive control sample to the binding reagent.

In some embodiments, the cell therapy is or comprises genetically engineered cells expressing an anti-GPRC5D CAR comprising a target antibody that is the target anti-GPRC5D antibody or an antigen-binding fragment thereof, wherein the binding reagent comprises the extracellular domain of the CAR or a portion thereof comprising the target anti-GPRC5D antibody or the antigen-binding fragment thereof. In some embodiments, the positive control includes an anti-idiotypic antibody as described in subsection I.A.

In some embodiments, the methods include detecting whether a complex is formed between the binding reagent and a molecule, e.g. binding molecule, such as an antibody, present in the sample, and/or detecting the presence or absence or level of such binding. In certain embodiments, the contacting or incubating is under conditions permissive for binding of the binding reagent to a molecule present in the sample from the subject. In some aspects, the complex is detected by an immunoassay, optionally a sandwich or bridge assay. For examples, the immunoassay is an enzyme-linked immunosorbent assay (ELISA), chemiluminescent, electrochemiluminescent, surface plasmon resonance (SPR)-based biosensor (e.g., BIAcore™) flow cytometry, or Western blot. In some embodiments, the immunoassay is or includes meso scale discovery.

In some aspects, the immunoassay is a sandwich assay or a bridge assay. In a sandwich or bridge assay, the binding reagent is a first binding reagent and detecting the presence or absence of a molecule or a complex comprising a molecule includes contacting the complex formed between the first binding reagent and molecule with a second binding reagent in which the second binding reagent is an agent that is able to bind to the same or similar molecule as the first binding reagent. In some embodiments, the second binding reagent comprises the extracellular domain of the CAR or a portion thereof. In some aspects, the extracellular domain of the CAR or portion thereof of the first binding agent and the second binding agent is the same or substantially the same.

In some embodiments, the binding reagent, such as the first and/or second binding reagent, is detectably labeled or is capable of producing a detectable signal. The binding reagent, such as the first and/or second binding reagent, is linked, directly or indirectly, to a detectable label. In some embodiments, the detectable label is or includes a fluorescent label, a chemiluminescent label, an electroluminescent label, a colorimetric label, a bioluminescent label or a radiolabel. In some embodiments, the binding reagent, such as the first and/or second binding reagent is linked, directly or indirectly, to a SULFO-Tag. In some embodiments, at least one of the first and second binding reagent is detectably labeled or is capable of producing a detectable signal and the other of the first and second binding reagent is attached or immobilized to a solid support. In some aspects, the first binding reagent is attached or immobilized to a solid support or capable of being attached or immobilized to a solid support. Methods for directly or indirectly attaching an binding reagent to a solid support are well known in the art. Methods of attachment generally include non-specific adsorption of the binding reagent to the solid support or covalent attachment of the binding reagent, typically through a free amine group, to a chemically reactive group on the solid support, such as an activated carboxyl, hydroxyl, or aldehyde group. Methods of attachment also include indirect attachment of the binding reagent to the solid support such as by coating the solid support with a capture reagent, such as streptavidin, and adding affinity labeled binding reagents, such as biotin-labeled reagents, to the solid support so that the interaction between the affinity label (e.g., biotin) and capture reagent (e.g., streptavidin) link the binding reagent to the solid support. In some embodiments, the first binding reagent is linked, directly or indirectly, to a biotin. In some examples, the first soluble reagent is bound to a solid support coated with streptavidin. In some embodiments, the second binding reagent is linked, directly or indirectly, to a detectably label, optionally a SULFO-Tag.

In particular embodiments, the sample is contacted with a first binding reagent that is attached, bound, coated, and/or conjugated to a solid surface or support, e.g., a plate or a well. In certain embodiments, the first binding reagent has been attached, bound, coated, and/or conjugated to the solid surface or support by indirect attachment of the binding reagent to the solid support such as by coating the solid support with a capture reagent, such as streptavidin, and adding affinity labeled binding reagents, such as biotin-labeled reagents, to the solid support so that the interaction between the affinity label (e.g., biotin) and capture reagent (e.g., streptavidin) link the binding reagent to the solid support. In some embodiments, the sample is contacted with a second binding reagent that is linked, directly or indirectly, to a SULFO-Tag. In particular embodiments, the first and/or second binding reagent is used at a concentration of between 10 ng/ml and 100 µg/ml, between 100 ng/ml and 1.0 pg/ml, between 250 ng/ml and 10 µg/ml, between 250 ng/ml and 1 pg/ml, between 1 µg/ml and 10 µg/ml, between 250 ng and 2.5 pg/ml, or between 1 µg/ml and 10 µg/ml the anti-idiotype antibody. In some embodiments, the solid surface or support is incubated with between 250 ng/ml and 10 µg/ml. In certain embodiments, the solid surface or support is incubated with or with about 0.25 pg/ml, 0.5 pg/ml, 1.0 pg/ml, 1.25 pg/ml, 2 µg/ml, 2.5 pg/ml, 5 µg/ml, or 10 µg/ml.

In some embodiments, the sample from a subject having been administered a cell therapy comprising cell engineered with a chimeric antigen receptor is or comprises any bodily fluid sample from the subject. In some aspects, the sample is or comprises whole blood, serum or plasma. In some embodiments, the sample is obtained from the subject within or about within 1 hour to 1 year after initiation of administration of the cell therapy or dose of cells, such as within or about within 6 hours, 12 hours, 24 hours, one week, two weeks, three weeks, one month, two months, three months, four months, five months, six months, seven months, eight months, nine months, ten months, eleven months or twelve months. In some aspects, the sample is obtained from the subject from or from about 1 month to 6 months of initiation of administration of the cell therapy, such as 2 months to 6 months or 2 months to 4 months, for example, about or approximately 2 months, 3 months, 4 months, 5 months or 6 months after initiation of administration of the cell therapy.

In some embodiments, the target antibody is an anti-GPRC5D antibody. In some of any such embodiments, the anti-GPRC5D antibody is the target anti-GPRC5D antibody, e.g., as described in Section I.A.

In some of any such embodiments, the anti-idiotype antibody or antigen-binding fragment thereof is an anti-idiotype antibody or antigen-binding fragment thereof that binds to or recognizes the target anti-GPRC5D antibody, such as any such anti-idiotype antibody or antigen-binding fragment thereof as described herein, e.g., in Section I.A.

V. ARTICLES OF MANUFACTURE OR KITS

Also provided are articles of manufacture or kits containing the provided anti-idiotype antibodies and/or compositions. In some embodiments, provided are articles of manufacture comprising an anti-idiotype antibody or an antigen-binding fragment thereof. In some cases, the anti-idiotype antibody binds an anti-GPRC5D antibody or antigen-binding fragment thereof, or a chimeric antigen receptor comprising an anti-GPRC5D antibody or antigen-binding fragment thereof. In some examples, the anti-GPRC5D antibody is the target anti-GPRC5D antibody, as described in, e.g., Section 1.A. In some aspects, a conjugate containing the anti-idiotype antibodies described herein are provided in the articles of manufacture or kits.

In some embodiments, the kit or article of manufacture includes the anti-idiotype antibody or antigen binding fragment thereof and a binding reagent containing the extracellular domain, or portion of an extracellular domain, of a chimeric antigen receptor (CAR) to which the anti-idiotype antibody binds, such as specifically binds, or recognizes. In some embodiments, the extracellular domain of the CAR is or includes the anti-GPRC5D antibody (e.g., the target anti-GPRC5D antibody), or an antigen-binding fragment thereof.

In some embodiments, the kit or article of manufacture includes the anti-idiotype antibody or antigen binding fragment thereof, and instructions for using the anti-idiotype antibody or antigen binding fragment thereof, to: (i) detect a target antibody or antigen-binding fragment thereof or a CAR comprising a target antibody or antigen-binding fragment thereof, and/or (ii) select or enrich, from a population of cells, engineered cells expressing a CAR comprising the target antibody or antigen-binding fragment thereof, and/or (iii) stimulate an input composition comprising cells expressing a CAR comprising the target antibody or antigen-binding fragment thereof.

In some embodiments, the kit or article of manufacture includes a binding reagent comprising an extracellular domain of a CAR comprising a target antibody or antigen-binding fragment thereof, said extracellular domain or portion thereof comprising the target antibody or antigen-binding fragment thereof, and an anti-idiotype antibody or antigen-binding fragment thereof, or immunoconjugate, as provided herein.

In some embodiments, the binding reagent is a first binding reagent and the kit or article of manufacture additionally includes a second binding reagent. In such examples, the second binding reagent is an agent that is able to bind to the same or similar molecule as the first binding reagent. In some embodiments, the second binding reagent comprises the extracellular domain of the CAR or a portion thereof. In some aspects, the extracellular domain of the CAR or portion thereof of the first binding agent and the second binding agent is the same or substantially the same In some embodiments, the binding reagent, or at least one of the first and second binding reagents, is attached to a label (e.g. detectable label) such as a label described herein. In some embodiments, at least one of the first and second binding reagent is attached to a solid support or capable of being attached to a solid support, such as a solid support described herein. In some aspects, one of the first and second binding reagent is detectably labeled or is capable of producing a detectable signal and the other of the first and seconding binding reagent is attached or immobilized to the solid support. In some embodiments, the binding reagents are provided as a kit or as part of a system as described elsewhere herein for use in connection with an immunoassay (e.g. sandwich or bridge assay). In some embodiments, the first binding reagent is bound to a solid support, optionally a streptavidin coated solid support. In some embodiments, the second soluble protein is linked directly or indirectly to a detectable label, such as SULFO-Tag.

In some embodiments, the kit further comprises an anti-idiotype antibody or antigen-binding fragment. In some aspects, the anti-idiotype antibody binds an anti-GPRC5D antibody or antigen-binding fragment thereof, or a chimeric antigen receptor comprising an anti-GPRC5D antibody or antigen-binding fragment thereof. In some examples, the anti-GPRC5D antibody is the target anti-GPRC5D antibody as described in, e.g., Section I.A. In some embodiments, the anti-idiotype antibody or antigen-binding fragment thereof is provided as a positive control sample. In some examples, the positive control sample forms a complex with the first and second soluble proteins or reagents which contains regions of the extracellular domain of a chimeric antigen receptor (CAR) comprising the anti-GPRC5D antibody or an antigen-binding fragment thereof.

In some embodiments, the kit or article of manufacture includes a cartridge device, e.g., for use in any of the methods described in Section IV.A. In some embodiments, the microfluidic cartridge contains a sample composition chamber. In some embodiments, the microfluidic cartridge contains a blister compartment. In some embodiments, the microfluidic cartridge contains a treatment compartment adapted for fluid mixing, said treatment compartment in fluid communication with the sample composition chamber and the blister. In some embodiments, the microfluidic cartridge contains an evaluation chamber including a reading zone, wherein the evaluation chamber is in fluid communication with the treatment chamber. In some embodiments, the reading zone allows for analysis of the sample as it passes through the reading zone.

In some embodiments, the blister contains an anti-idiotype antibody or antigen binding fragment thereof. In some embodiments, the anti-idiotype antibody is conjugated to a detectable label, e.g., a fluorescent label. In some aspects, the anti-idiotype antibody binds an anti-GPRC5D antibody or antigen-binding fragment thereof, or a chimeric antigen receptor comprising an anti-GPRC5D antibody or antigen-binding fragment thereof. In some examples, the anti-GPRC5D antibody is the target anti-GPRC5D antibody as described in, e.g., Section I.A.

In some embodiments, the kit or article of manufacture includes a dried-down anti-idiotype antibody or antigen binding fragment thereof, e.g., for use in any of the methods described in Section IV.A. In some embodiments, the dried-down anti-idiotype antibody is conjugated to a detectable label, e.g., a fluorescent label. In some aspects, the dried-down anti-idiotype antibody binds an anti-GPRC5D antibody or antigen-binding fragment thereof, or a chimeric antigen receptor comprising an anti-GPRC5D antibody or antigen-binding fragment thereof. In some examples, the anti-GPRC5D antibody is the target anti-GPRC5D antibody as described in, e.g., Section I.A. In some embodiments, the dried-down anti-idiotype antibody or antigen binding fragment thereof is contained in a tube. In some embodiments, the tube further contains other dried-down reagents, e.g., other labelled antibodies, dyes, or cell lysing agents.

In some embodiments, the kit or article of manufacturer comprises reagents or components for carrying out any of the provided methods. In some embodiments, the article of manufacture or kit comprises one or more reagent or other materials desirable from a commercial, therapeutic, and user standpoint including secondary antibodies, affinity labels, capture reagents, buffers, diluents, signal detection agents, filters, needles, syringes, capillary tubes, and package inserts with instructions for use.

In some embodiments, the kits can be provided as articles of manufacture that include packing materials for the packaging of the antibodies or compositions thereof or the one or more additional reagents, e.g. binding reagents, or components. For example, the kits can contain containers, bottles, tubes, vial and any packaging material suitable for separating or organizing the components of the kit.

In some embodiments, the kit includes one or more containers. Suitable containers include, for example, bottles, vials (e.g., dual chamber vials), syringes (such as single or dual chamber syringes) and test tubes. The one or more containers may be formed from a variety of materials such as glass or plastic. The one or more containers hold a composition comprising an antibody or other reagents, e.g. binding reagents, for use in the methods. The article of manufacture or kit herein may comprise the antibodies or reagents in separate containers or in the same container. In some embodiments, the one or more containers holding the composition may be a single-use vial or a multi-use vial, which, in some cases, may allow for repeat use of the reconstituted composition.

In some embodiments, the article of manufacture or kit may further comprise a second container comprising a suitable diluent. The article of manufacture or kit may further include other materials desirable from a commercial, therapeutic, and user standpoint, including other buffers, diluents, filters, needles, syringes, therapeutic agents and/or package inserts with instructions for use.

The articles of manufacture may include a container and a label or package insert on or associated with the container. Suitable containers include, for example, bottles, vials, syringes, IV solution bags, etc. The containers may be formed from a variety of materials such as glass or plastic. The container in some embodiments holds a composition containing an anti-idiotype antibody as provided herein which is by itself or is combined with another composition effective for treating, preventing and/or diagnosing a disease or condition. In some embodiments, the container has a sterile access port. Exemplary containers include an intra-venous solution bags, vials, including those with stoppers pierceable by a needle for injection. The article of manu-facture may include a first container with a composition contained therein, wherein the composition includes the anti-idiotype antibody. Alternatively, or additionally, the article of manufacture may further include another or the same container comprising an acceptable buffer. It may further include other materials such as other buffers, diluents, filters, needles, and/or syringes.

In some embodiments, the article of manufacture or kit comprises a solid support, including a solid support formed of glass (e.g., controlled pore glass), polysaccharides (e.g., agarose), polyacrylamides, polystyrene, polyvinyl alcohol, nitrocellulose, cellulose, nylon, silicones and other material well known in the art that is used in a solid support for direct or indirect attachment of a binding reagent as described. Solid supports included in the articles of manufacture or kits provided herein include, but are not limited to, a bead, column (e.g., chromatography column, etc.), an array (e.g., microarray, nanoarray, etc.), an assay plate, a cartridge, a stick, a filter, a strip or any other solid support described herein.

In some embodiments, the article of manufacture or kit may further comprise a second container comprising a suitable diluent. The article of manufacture or kit may further include other materials desirable from a commercial, therapeutic, and user standpoint, including other buffers, diluents, filters, needles, syringes, therapeutic agents and/or package inserts with instructions for use.

In some embodiments, the kit can, optionally, include instructions. Instructions typically include a tangible expres-sion describing the antibodies and, optionally, other com-ponents included in the kit, e.g. binding reagent, and meth-ods for using the antibodies and/or other components in or in conjunction with any of the uses or methods as described. In some embodiments, the instructions are provided as a label or a package insert, which is on or associated with the container. In some embodiments, the instructions may indi-cate directions for reconstitution and/or use of the compo-sition.

In some embodiments, instructions are provided for using the anti-idiotype antibody to detect the target anti-GPRC5D antibody or antigen-binding fragment thereof or a chimeric antigen receptor comprising the target anti-GPRC5D anti-body or antigen-binding fragment thereof, such as in accord with or conjunction with any of the methods or assays as described. In some examples, instructions are provided for using the anti-idiotype antibody to select or enrich, from a population of cells, engineered cells expressing a chimeric antigen receptor (CAR) comprising the target anti-GPRC5D antibody or an antigen-binding fragment thereof. In some examples, instructions are provided for using the anti-idiotype antibody to stimulate an input composition com-prising cells expressing a chimeric antigen receptor com-prising the target anti-GPRC5D antibody or antigen-binding fragment thereof.

In some embodiments, instructions are provided for use of the kit provided to detect a molecule that binds to a chimeric antigen receptor of the cell therapy, such as an antibody, e.g. an antibody produced by a humoral immune response to the chimeric antigen receptor (CAR). In some embodiments, the instructions are provided for contacting a binding reagent with a sample from a subject having been administered a cell therapy comprising cells engineered with a CAR comprising a target antibody that is the anti-GPRC5D antibody (e.g., the target anti-GPRC5D antibody as described in, e.g., Section IA) or an antigen-binding fragment thereof, wherein the binding reagent comprises the extracellular domain of the CAR or a portion of the extracellular domain comprising the target antibody or the antigen-binding fragment thereof. In some aspects, the instructions also specify detecting the presence or absence of a complex comprising the binding reagents and a molecule from the sample that binds to both the first and the second binding reagent, optionally wherein the molecule is or comprises an antibody. In some aspects, the GPRC5D antibody is the target anti-GPRC5D antibody.

VI. DEFINITIONS

Unless defined otherwise, all terms of art, notations and other technical and scientific terms or terminology used herein are intended to have the same meaning as is com-monly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, reference to a "corresponding form" of an antibody means that when comparing a property or activity of two antibodies, the property is compared using the same form of the antibody. For example, if it is stated that an antibody has greater activity compared to the activity of the corresponding form of a first antibody, that means that a particular form, such as a scFv of that antibody, has greater activity compared to the scFv form of the first antibody.

As used herein, recitation that nucleotides or amino acid positions "correspond to" nucleotides or amino acid posi-tions in a disclosed sequence, such as set forth in the Sequence listing, refers to nucleotides or amino acid posi-tions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Proj-ects, Smith, D. W., ed., Academic Press, New York, 1993;

Computer Analysis of Sequence Data, Part I, Griffin, A. M., and Griffin, H. G., eds., Humana Press, New. Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The terms "full length antibody," "intact antibody," and "whole antibody" are used herein interchangeably to refer to an antibody having a structure substantially similar to a native antibody structure or having heavy chains that contain an Fc region as defined herein.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848: 79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-idiotype antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign™ (DNASTAR) software. Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The terms "polypeptide" and "protein" are used interchangeably to refer to a polymer of amino acid residues, and are not limited to a minimum length. Polypeptides, including the provided antibodies and antibody chains and other peptides, e.g., linkers, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that binds to the marker (e.g., specifically binds to the marker) and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that binds to the marker (e.g., specifically binds to the marker) and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

VII. EXEMPLARY EMBODIMENTS

Among the provided embodiments are:

1. An anti-idiotype antibody or antigen-binding fragment thereof that binds to or recognizes an anti-GPRC5D target antibody or antigen-binding fragment thereof, wherein the anti-idiotype antibody or antigen-binding fragment thereof comprises:
a VH region comprising a heavy chain complementarity-determining region 1 (CDR-H1) comprising the amino acid sequence set forth in SEQ ID NO: 15, a CDR-H2 comprising the amino acid sequence set forth in SEQ ID NO: 16, and a CDR-H3 comprising the amino acid sequence set forth in SEQ ID NO: 17; and
a VL region comprising a light chain complementarity-determining region 1 (CDR-L1) comprising the amino acid sequence set forth in SEQ ID NO: 22, a CDR-L2 comprising the amino acid sequence set forth in SEQ ID NO: 23, and a CDR-L3 comprising the amino acid sequence set forth in SEQ ID NO: 24.

2. An anti-idiotype antibody or antigen-binding fragment thereof that binds to or recognizes an anti-GPRC5D target antibody or antigen-binding fragment thereof, wherein the anti-idiotype antibody or antigen-binding fragment thereof comprises:
a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 25; and
a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 26.

3. The anti-idiotype antibody or antigen-binding fragment thereof of embodiment 1 or embodiment 2, wherein:
the VH region comprises an amino acid sequence having at least 90% sequence identity to the amino acid sequence set forth in SEQ ID NO: 25; and
the VL region comprises an amino acid sequence having at least 90% sequence identity to the amino acid sequence set forth in SEQ ID NO: 26.

4. An anti-idiotype antibody or antigen-binding fragment thereof that binds to or recognizes an anti-GPRC5D target antibody or antigen-binding fragment thereof, wherein the anti-idiotype antibody or antigen-binding fragment thereof comprises:
a VH region comprising an amino acid sequence having at least 90% sequence identity to the amino acid sequence set forth in SEQ ID NO: 25; and
a VL region comprising an amino acid sequence having at least 90% sequence identity to the amino acid sequence set forth in SEQ ID NO: 26.

5. The anti-idiotype antibody or antigen-binding fragment thereof of any one of embodiments 2-4, wherein:

the VH region comprises a CDR-H1 comprising the amino acid sequence set forth in SEQ ID NO: 15, a CDR-H2 comprising the amino acid sequence set forth in SEQ ID NO: 16, and a CDR-H3 comprising the amino acid sequence set forth in SEQ ID NO: 17; and the VL region comprising a CDR-L1 comprising the amino acid sequence set forth in SEQ ID NO: 22, a CDR-L2 comprising the amino acid sequence set forth in SEQ ID NO: 23, and a CDR-L3 comprising the amino acid sequence set forth in SEQ ID NO: 24.

6. The anti-idiotype antibody or antigen-binding fragment thereof of any one of embodiments 1-5, wherein:

the VH region comprises the amino acid sequence set forth in SEQ ID NO: 25; and the VL region comprises the amino acid sequence set forth in SEQ ID NO: 26.

7. An anti-idiotype antibody or antigen-binding fragment thereof that binds to or recognizes an anti-GPRC5D target antibody or antigen-binding fragment thereof, wherein the anti-idiotype antibody or antigen-binding fragment thereof comprises:

a heavy chain variable (VH) region comprising the amino acid sequence set forth in SEQ ID NO: 25; and a light chain variable (VL) region comprising the amino acid sequence set forth in SEQ ID NO: 26.

8. The anti-idiotype antibody or antigen-binding fragment thereof of any one of embodiments 1-7, comprising at least a portion of an immunoglobulin constant region of a heavy chain and/or a light chain.

9. The anti-idiotype antibody or antigen-binding fragment thereof of embodiment 8, wherein the anti-idiotype antibody or antigen-binding fragment comprises a heavy chain constant region comprising an Fc region or a portion of the Fc comprising the CH2 and CH3 domains and/or a light chain constant region comprising a CL domain.

10. The anti-idiotype antibody or antigen-binding fragment thereof of embodiment 8 or embodiment 9, wherein the constant region is from IgG, optionally IgG1.

11. The anti-idiotype antibody or antigen-binding fragment thereof of embodiment 9 or embodiment 10, wherein the light chain constant region is from a kappa light chain.

12. The anti-idiotype antibody or antigen-binding fragment thereof of any one of embodiments 8-11, which is an intact antibody or full-length antibody.

13. The anti-idiotype antibody or antigen-binding fragment thereof of any one of embodiments 1-12, wherein the anti-idiotype antibody or antigen-binding fragment thereof comprises:

a heavy chain comprising an amino acid sequence having at least 90% sequence identity to the amino acid sequence set forth in SEQ ID NO: 27; and a light chain comprising an amino acid sequence having at least 90% sequence identity to the amino acid sequence set forth in SEQ ID NO: 28.

14. The anti-idiotype antibody or antigen-binding fragment thereof of any one of embodiments 1-13, wherein the anti-idiotype antibody or antigen-binding fragment thereof comprises:

a heavy chain comprising an amino acid sequence set forth in SEQ ID NO: 27; and a light chain comprising an amino acid sequence set forth in SEQ ID NO: 28.

15. The anti-idiotype antibody or antigen-binding fragment thereof of any one of embodiments 1-11, which is an antigen-binding fragment.

16. The anti-idiotype antibody or antigen-binding fragment thereof of embodiment 15, wherein the antigen-binding fragment is selected from among Fab fragments, F(ab')2 fragments, Fab' fragments, Fv fragments, an scFv, and a single domain antibody.

17. The anti-idiotype antibody or antigen-binding fragment thereof of any one of embodiments 1-16, which is humanized.

18. The anti-idiotype antibody or antigen-binding fragment thereof of any one of embodiments 1-17, which is recombinant.

19. The anti-idiotype antibody or antigen-binding fragment thereof of any one of embodiments 1-18, which is monoclonal.

20. The anti-idiotype antibody or antigen-binding fragment thereof of any one of embodiments 1-19, wherein the anti-GPRC5D target antibody or antigen-binding fragment thereof binds to or recognizes human G Protein-Coupled Receptor Class C Group 5 Member D (GPRC5D).

21. The anti-idiotype antibody or antigen-binding fragment thereof of any one of embodiments 1-20, wherein the anti-GPRC5D target antibody or antigen-binding fragment thereof comprises a VH region comprising the amino acid sequence set forth in SEQ ID NO: 7, and a VL region comprising the amino acid sequence set forth in SEQ ID NO: 8.

22. The anti-idiotype antibody or antigen-binding fragment thereof of embodiment 21, wherein the anti-GPRC5D target antibody or antigen-binding fragment thereof is a single chain fragment.

23. The anti-idiotype antibody or antigen-binding fragment thereof of embodiment 22, wherein the single chain fragment comprises a flexible linker positioned between the VH region and the VL region.

24. The anti-idiotype antibody or antigen-binding fragment thereof of embodiment 23, wherein the flexible linker comprises the amino acid sequence set forth in SEQ ID NO: 10.

25. The anti-idiotype antibody or antigen-binding fragment thereof of any one of embodiments 22-24, wherein the single chain fragment of the anti-GPRC5D target antibody or antigen binding fragment is a single chain variable fragment (scFv).

26. The anti-idiotype antibody or antigen-binding fragment thereof of embodiment 25, wherein the scFv comprises the amino acid sequence set forth in SEQ ID NO: 9.

27. The anti-idiotype antibody or antigen-binding fragment thereof of any one of embodiments 1-26, wherein the anti-idiotype antibody or antigen-binding fragment binds to or recognizes an epitope within or including all or a portion of a complementarity determining region (CDR) of the anti-GPRC5D target antibody or antigen-binding fragment thereof.

28. The anti-idiotype antibody or antigen-binding fragment thereof of any one of embodiments 1-27, wherein:

the anti-GPRC5D target antibody or antigen-binding fragment thereof is within or included in an antigen-binding domain of an extracellular portion of a chimeric antigen receptor (CAR); and/or the anti-idiotype antibody or antigen-binding fragment thereof specifically binds the anti-GPRC5D target antibody or antigen-binding fragment thereof comprised within or included in an antigen-binding domain of an extracellular portion of a CAR.

29. The anti-idiotype antibody or antigen-binding fragment thereof of any one of embodiments 25-27, wherein:

the scFv is within or included in an extracellular portion of a CAR; and/or the anti-idiotype antibody or antigen-binding fragment thereof specifically binds the scFv comprised within or included in an extracellular portion of a CAR.

30. The anti-idiotype antibody or antigen-binding fragment thereof of embodiment 28 or embodiment 29, wherein the CAR further comprises a transmembrane domain linked to the antigen-binding domain via a spacer.

31. The anti-idiotype antibody of antigen-binding fragment thereof of embodiment 30, wherein the spacer is an immunoglobulin spacer, optionally wherein the spacer comprises the amino acid sequence set forth in SEQ ID NO: 11.

32. The anti-idiotype antibody or antigen-binding fragment thereof of embodiment 30 or embodiment 31, wherein the transmembrane domain comprises a transmembrane portion of CD28, which optionally is human CD28.

33. The anti-idiotype antibody or antigen-binding fragment thereof of any one of embodiments 30-32, wherein the anti-idiotype antibody or antigen-binding fragment thereof does not bind to an epitope in the spacer domain of the CAR.

34. The anti-idiotype antibody or antigen-binding fragment thereof of any one of embodiments 1-33, wherein the anti-idiotype antibody or antigen-binding fragment thereof does not bind or does not specifically bind to CD28 or a portion thereof, which optionally is human CD28.

35. The anti-idiotype antibody or antigen-binding fragment thereof of any one of embodiments 1-34, wherein the anti-idiotype antibody or antigen-binding fragment thereof does not bind to an epitope in an Fc domain, which optionally is a human IgG1 Fc domain.

36. The anti-idiotype antibody or antigen-binding fragment thereof of any one of embodiments 1-35, wherein the anti-idiotype antibody or antigen-binding fragment thereof specifically binds to the anti-GPRC5D target antibody or antigen-binding fragment thereof.

37. The anti-idiotype antibody or antigen-binding fragment thereof of any one of embodiments 1-36, wherein the anti-idiotype antibody or antigen-binding fragment thereof has a dissociation constant to the anti-GPRC5D target antibody or antigen-binding fragment thereof that is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM.

38. The anti-idiotype antibody or antigen-binding fragment thereof of any one of embodiments 1-37, wherein the anti-idiotype antibody or antigen-binding fragment thereof is an agonist of a CAR comprising the anti-GPRC5D target antibody or antigen-binding fragment thereof.

39. The anti-idiotype antibody or antigen-binding fragment thereof of embodiment 38, wherein the anti-idiotype antibody or antigen-binding fragment thereof is an agonist of the CAR when in solution.

40. The anti-idiotype antibody or antigen-binding fragment thereof of embodiment 38, wherein the anti-idiotype antibody or antigen-binding fragment thereof is an agonist of the CAR when immobilized to a support or a stationary phase, optionally wherein the support or stationary phase is a plate or a bead.

41. A conjugate, comprising the anti-idiotype antibody or antigen-binding fragment thereof of any one of embodiments 1-40 and a heterologous molecule or moiety.

42. The conjugate of embodiment 41, wherein the heterologous molecule or moiety is a label.

43. The conjugate of embodiment 42, wherein the label is selected from a fluorescent dye, a fluorescent protein, a radioisotope, a chromophore, a metal ion, a gold particle, a silver particle, a magnetic particle, a polypeptide, an enzyme, a streptavidin, a biotin, a luminescent compound, and an oligonucleotide.

44. The conjugate of embodiment 42, wherein the heterologous molecule or moiety is a protein, peptide, nucleic acid or small molecule, which optionally is or comprises a toxin or a Strep-Tag.

45. A nucleic acid molecule(s) encoding the heavy chain and/or the light chain of the anti-idiotype antibody or antigen-binding fragment thereof of any one of embodiments 1-40.

46. The nucleic acid molecule(s) of embodiment 45, comprising:

a sequence of nucleotides encoding (i) the heavy chain variable region set forth in SEQ ID NO: 25, (ii) a heavy chain variable region that has at least 90% sequence identity to the amino acid sequence set forth in SEQ ID NO: 25; or (iii) a degenerate sequence of (i) or (ii); and a sequence of nucleotides encoding (iv) the light chain variable region set forth in SEQ ID NO: 26, (v) a light chain variable region that has at least 90% sequence identity to the amino acid sequence set forth in SEQ ID NO: 26; or (vi) a degenerate sequence of (iv) or (v).

47. The nucleic acid molecule(s) of embodiment 45, comprising:

a sequence of nucleotides encoding (i) the heavy chain set forth in SEQ ID NO: 27, (ii) a heavy chain that has at least 90% sequence identity to the amino acid sequence set forth in SEQ ID NO: 27; or (iii) a degenerate sequence of (i) or (ii); and a sequence of nucleotides encoding (iv) the light chain set forth in SEQ ID NO: 28, (v) a light chain that has at least 90% sequence identity to the amino acid sequence set forth in SEQ ID NO: 28; or (vi) a degenerate sequence of (iv) or (v).

48. The nucleic acid molecule(s) of any one of embodiments 45-47, wherein the nucleic acid molecule(s) encoding the heavy chain and/or light chain comprises a signal sequence.

49. The nucleic acid molecule(s) of any one of embodiments 45-48, wherein the nucleic acid molecule(s) comprise one or more nucleotide sequences selected from the group consisting of SEQ ID NOs: 29-32.

50. A vector, comprising the nucleic acid molecule(s) of any one of embodiments 45-49.

51. A cell, comprising the anti-idiotype antibody or antigen-binding fragment thereof of any one of embodiments 1-40, the nucleic acid molecule of any one of embodiments 45-49, or the vector of embodiment 50.

52. A method of producing an anti-idiotype antibody or antigen-binding fragment thereof, comprising:

expressing the heavy and/or light chain encoded by the nucleic acid molecule(s) of any one of embodiments 45-49 or the vector of embodiment 50 in a suitable host cell; and recovering or isolating the antibody.

53. A method of producing an anti-idiotype antibody or antigen-binding fragment thereof, comprising:

culturing the cell of embodiment 51 under conditions in which the heavy chain and/or light chain is expressed; and recovering or isolating the antibody.

54. An anti-idiotype antibody or antigen-binding fragment thereof produced by the method of embodiment 52 or embodiment 53.

55. A composition, comprising the anti-idiotype antibody or antigen-binding fragment thereof of any one of embodiments 1-40, the conjugate of any one of embodiments 41-44, or the cell of embodiment 51.

56. The composition of embodiment 55, further comprising a pharmaceutically acceptable excipient.

57. A kit, comprising one or more of the anti-idiotype antibody or antigen-binding fragment thereof of any one of embodiments 1-40, the conjugate of any one of embodiments 41-44, the nucleic acid molecule(s) of any one of embodiments 45-49, and, optionally, instructions for use.

58. The kit of embodiment 57, further comprising a reagent or support for immobilizing the anti-idiotype antibody or antigen-binding fragment thereof or the conjugate, wherein said reagent or support is a bead, a column, a microwell, a stick, a filter, a strip or a soluble oligomeric streptavidin mutein reagent.

59. A method of detecting a target antibody or antigen-binding fragment thereof, comprising:

(a) contacting a composition comprising a target antibody or antigen-binding fragment thereof with the anti-idiotype antibody or antigen-binding fragment thereof of any one of embodiments 1-40 or the conjugate of any one of embodiments 41-44 that specifically binds to the target antibody or antigen-binding fragment thereof, and (b) detecting the anti-idiotype antibody bound to the target antibody or antigen-binding fragment thereof.

60. The method of embodiment 59, wherein the target antibody or antigen-binding fragment thereof is bound to a cell or expressed on the surface of a cell, and the detecting in (b) comprises detecting cells bound with the anti-idiotype antibody or antigen-binding fragment thereof.

61. The method of embodiment 60, wherein the cell expresses on its surface a CAR comprising the target antibody or antigen-binding fragment thereof.

62. A method of detecting a CAR comprising a target antibody or antigen-binding fragment thereof, comprising:

(a) contacting a cell expressing a CAR comprising a target antibody or antigen-binding fragment thereof with the anti-idiotype antibody or antigen-binding fragment thereof of any one of embodiments 1-40, or the conjugate of any one of embodiments 41-44, that specifically binds to the target antibody or antigen-binding fragment thereof, and (b) detecting cells bound with the anti-idiotype antibody or antigen-binding fragment thereof.

63. The method of embodiment 62, wherein the anti-idiotype antibody or antigen-binding fragment thereof is directly or indirectly labeled for detection.

64. A method of selecting cells from a cell population, comprising:

(a) contacting a cell population expressing a CAR comprising a target antibody or antigen-binding fragment thereof or a cell bound to a target antibody or antigen-binding fragment thereof with the anti-idiotype antibody or antigen-binding fragment thereof of any one of embodiments 1-40, or the conjugate of any one of embodiments 41-44, that specifically binds to the target antibody or antigen-binding fragment thereof, and (b) selecting cells bound with the anti-idiotype antibody or antigen-binding fragment thereof.

65. The method of embodiment 64, wherein the cells bound with the anti-idiotype antibody or antigen-binding fragment thereof are selected by affinity-based separation.

66. The method of embodiment 65, wherein the affinity-based separation is immunoaffinity-based separation.

67. The method of embodiment 65 or embodiment 66, wherein the affinity-based separation is by flow cytometry.

68. The method of embodiment 65 or embodiment 66, wherein the affinity-based separation is by magnetic activated cell sorting.

69. The method of embodiment 65 or embodiment 66, wherein the affinity-based separation comprises affinity chromatography.

70. The method of embodiment 68 or embodiment 69, wherein the anti-idiotype antibody or antigen-binding fragment thereof is reversibly bound or immobilized to a support or a stationary phase.

71. A method of stimulating cells, comprising incubating an input composition comprising cells expressing a CAR comprising a target antibody or antigen-binding fragment thereof with the anti-idiotype antibody or antigen-binding fragment thereof of any one of embodiments 1-40, or the conjugate of any one of embodiments 41-44, that specifically binds to the target antibody or antigen-binding fragment thereof, thereby generating an output composition comprising stimulated cells.

72. A method of producing a cell composition, comprising:

(a) introducing into cells a nucleic acid molecule(s) encoding a CAR, thereby generating an input composition; and (b) incubating the input composition with the anti-idiotype antibody or antigen-binding fragment thereof of any one of embodiments 1-40, or the conjugate of any one of embodiments 41-44, that specifically binds to an antigen receptor of the CAR, thereby producing the cell composition.

73. The method of embodiment 72, wherein the introducing in (a) comprises introducing the nucleic acid molecule(s) into the cells by viral transduction, transposition, electroporation, or chemical transfection.

74. The method of embodiment 72 or embodiment 73, wherein the introducing in (a) comprises introducing the nucleic acid molecule(s) in the cells by transduction with a viral vector comprising the nucleic acid molecule(s), optionally wherein the viral vector is a retroviral vector or a lentiviral vector.

75. The method of embodiment 72 or embodiment 73, wherein the introducing in (a) comprises introducing the nucleic acid molecule(s) in the cells by transposition with a transposon comprising the nucleic acid molecule(s).

76. The method of embodiment 72 or embodiment 73, wherein the introducing in (a) comprises introducing the nucleic acid molecule(s) in the cells by electroporation or transfection of a vector comprising the nucleic acid molecule(s).

77. The method of any one of embodiments 72-76, further comprising a step of activating the cells prior to step (a).

78. The method of embodiment 77, wherein the step of activating the cells comprises contacting the cells with an agonist of CD3 and optionally an agonist of CD28.

79. The method of embodiment 78, wherein the step of activating the cells comprises contacting the cells with a reagent comprising agonistic anti-CD3 and anti-CD28 antibodies.

80. The method of any one of embodiments 72-79, wherein the incubation is performed under conditions in which the anti-idiotype antibody or antigen-binding fragment thereof binds to the CAR, thereby inducing or modulating a signal in one or more cells in the input composition.

81. The method of any one of embodiments 72-80, wherein the cells comprise T cells.

82. The method of embodiment 81, wherein the T cells comprise CD4+ and/or CD8+ T cells.

83. The method of any one of embodiments 72-82, wherein the anti-idiotype antibody or antigen-binding fragment thereof is immobilized to a solid support, which optionally comprises or is conjugated to a reagent comprising a plurality of binding sites capable of reversibly binding to the anti-idiotype antibody or antigen-binding fragment thereof.

84. The method of any one of embodiments 72-82, wherein the anti-idiotype antibody or antigen-binding fragment thereof is immobilized to a soluble reagent, which optionally is or comprises a plurality of binding sites capable of reversibly binding to the anti-idiotype antibody or antigen-binding fragment thereof.

85. The method of embodiment 83 or embodiment 84, wherein the reagent comprises a streptavidin mutein.

86. The method of any one of embodiments 72-85, wherein the incubation is for at least or about at least 5 minutes, 10 minutes, 30 minutes, 60 minutes, 2 hours, 6 hours, 12 hours, 24 hours, 36, 48 hours, 72 hours or 96 hours.

87. The method of any one of embodiments 72-86, wherein the input composition comprises less than or less than about 60%, less than or less than about 50%, less than or less than about 40%, less than or less than about 30%, less than or less than about 20% or less than or less than about 10% CAR-expressing cells as a percentage of the total cells in the composition.

88. The method of any one of embodiments 72-87, wherein:

the number of CAR-expressing cells in the output composition is increased by greater than 1.2-fold, 1.5-fold, 2.0-fold, 3.0-fold, 4.0-fold, 5.0-fold, 10-fold or more compared to the number of CAR-expressing cells in the input composition; and/or the percentage of CAR-expressing in the output composition compared to the total cells in the composition is increased by greater than 10%, 20%, 40%, 50%, 60%, 70%, 80%, or more.

89. The method of any one of embodiments 72-88, wherein prior to the introducing and/or the incubating, the cells are not selected or enriched for CAR-expressing cells.

90. A method of purifying an anti-idiotype antibody or antigen-binding fragment thereof, comprising:

(a) contacting a composition comprising a target antibody or antigen-binding fragment thereof with the anti-idiotype antibody or antigen-binding fragment thereof of any one of embodiments 1-40, or the conjugate of any one of embodiments 41-44, that specifically binds to the target antibody or antigen-binding fragment thereof; and (b) isolating complexes comprising the anti-idiotype antibody or antigen-binding fragment thereof.

91. The method of embodiment 90, wherein the complexes comprising the anti-idiotype antibody or antigen-binding fragment thereof are isolated by affinity-based separation.

92. The method of embodiment 91, wherein the affinity-based separation is immunoaffinity-based separation.

93. The method of embodiment 92, wherein the affinity-based separation is magnetic-based separation.

94. The method of embodiment 92, wherein the affinity-based separation comprises affinity chromatography.

95. A method of depleting cells, comprising administering, to a subject, a composition comprising the anti-idiotype antibody or antigen-binding fragment thereof of any one of embodiments 1-40, or the conjugate of any one of embodiments 41-44, that specifically binds to a target antibody or antigen-binding fragment thereof, wherein the subject has been administered a cell expressing a CAR comprising the target antibody or antigen-binding fragment thereof.

96. The method of embodiment 95, wherein the depletion occurs via antibody-dependent cell-mediated cytotoxicity (ADCC).

97. The method of any one of embodiments 59-96, wherein the target antibody or antigen-binding fragment thereof is a single chain fragment.

98. The method of embodiment 97, wherein the single chain fragment comprises an scFv.

99. The method of any one of embodiments 59-98, wherein the target antibody or antigen-binding fragment thereof comprises a VH region comprising the amino acid sequence set forth in SEQ ID NO: 7, and a VL region comprising the amino acid sequence set forth in SEQ ID NO: 8.

100. The method of embodiment 99, wherein the target antibody or antigen-binding fragment thereof is an scFv and the VH region and the VL region are joined by a flexible linker.

101. The method of embodiment 100, wherein the flexible linker comprises the amino acid sequence set forth in SEQ ID NO: 10, and the scFv comprises the amino acid sequence set forth in SEQ ID NO: 9.

102. An article of manufacture comprising the anti-idiotype antibody or antigen-binding fragment thereof of any one of embodiments 1-40, or the conjugate of any one of embodiments 41-44, and instructions for using the anti-idiotype antibody or antigen-binding fragment thereof to:

detect a target antibody or antigen-binding fragment thereof or a CAR comprising the target antibody or antigen-binding fragment thereof; and/or select or enrich, from a population of cells, engineered cells expressing a CAR comprising the target antibody or antigen-binding fragment thereof; and/or stimulate an input composition comprising cells expressing a CAR comprising the target antibody or antigen-binding fragment thereof.

103. An article of manufacture comprising:

a binding reagent comprising an extracellular domain of a CAR comprising a target antibody or antigen-binding fragment thereof, said extracellular domain or portion thereof comprising the target antibody or antigen-binding fragment thereof; and an anti-idiotype antibody or antigen-binding fragment of any of embodiments 1-40, or the conjugate of any one of embodiments 41-44.

104. The article of manufacture of embodiment 103, wherein the binding reagent is a first binding reagent and the article of manufacture further comprises a second binding reagent comprising the extracellular domain or portion thereof of the CAR.

105. The article of manufacture of embodiment 103 or embodiment 104, wherein the extracellular domain of the CAR or portion thereof of the first and second binding reagent is the same.

106. The article of manufacture of any of embodiments 103-105, further comprising instructions for using the binding reagent, optionally the first and second binding reagent, for assaying a sample for the presence or absence of a molecule that binds to the binding reagent using an immunoassay, optionally wherein the immunoassay is a bridge or sandwich immunoassay, optionally wherein the sample is from a subject having been administered a cell therapy comprising cells engineered with a CAR comprising the target antibody or antigen-binding fragment thereof.

107. The article of manufacture of any of embodiments 103-106, wherein the binding reagent, optionally the first and/or second binding reagent, is detectably labeled or capable of producing a detectable signal.

108. The article of manufacture of any of embodiments 104-107, wherein one of the first and second binding reagent is attached to a solid support of is capable of being attached to a solid support and the other of the first and second binding reagent is detectably labeled or is capable of producing a detectable signal.

109. The article of manufacture of embodiment 108, wherein the article of manufacture further comprises a solid support, optionally wherein the one of the first and second binding reagent is linked directly or indirectly to biotin, and the solid support comprises a streptavidin-coated surface.

110. The article of manufacture of any one of embodiments 102-109, wherein the target antibody or antigen-binding fragment thereof is a single chain fragment.

111. The article of manufacture of embodiment 110, wherein the single chain fragment comprises an scFv.

112. The article of manufacture of any one of embodiments 102-111, wherein the target antibody or antigen-binding fragment thereof comprises a VH region comprising the amino acid sequence set forth in SEQ ID NO: 7, and a VL region comprising the amino acid sequence set forth in SEQ ID NO: 8.

113. The article of manufacture of embodiment 112, wherein the target antibody or antigen-binding fragment thereof is an scFv and the VH region and the VL region are joined by a flexible linker.

114. The article of manufacture of embodiment 113, wherein the flexible linker comprises the amino acid sequence set forth in SEQ ID NO: 10, and the scFv comprises the amino acid sequence set forth in SEQ ID NO: 9.

Among the provided embodiments are:

1. An anti-idiotype antibody or antigen-binding fragment thereof that binds to or recognizes an anti-GPRC5D target antibody or antigen-binding fragment thereof, wherein the anti-idiotype antibody or antigen-binding fragment comprises:

a heavy chain variable (VH) region comprising the amino acid sequence set forth in SEQ ID NO: 25; and a light chain variable (VL) region comprising the amino acid sequence set forth in SEQ ID NO: 26.

2. An anti-idiotype antibody or antigen-binding fragment thereof that binds to or recognizes an anti-GPRC5D target antibody or antigen-binding fragment thereof, wherein the anti-idiotype antibody or antigen-binding fragment thereof comprises:

a VH region comprising an amino acid sequence having at least 90% sequence identity to the amino acid sequence set forth in SEQ ID NO: 25; and a VL region comprising an amino acid sequence having at least 90% sequence identity to the amino acid sequence set forth in SEQ ID NO: 26.

3. An anti-idiotype antibody or antigen-binding fragment thereof that binds to or recognizes an anti-GPRC5D target antibody or antigen-binding fragment thereof, wherein the anti-idiotype antibody or antigen-binding fragment thereof comprises:

a VH region comprising a heavy chain complementarity-determining region 1 (CDR-H1) comprising the amino acid sequence set forth in SEQ ID NO: 15, a CDR-H2 comprising the amino acid sequence set forth in SEQ ID NO: 16, and a CDR-H3 comprising the amino acid sequence set forth in SEQ ID NO: 17; and a VL region comprising a light chain complementarity-determining region 1 (CDR-L1) comprising the amino acid sequence set forth in SEQ ID NO: 22, a CDR-L2 comprising the amino acid sequence set forth in SEQ ID NO: 23, and a CDR-L3 comprising the amino acid sequence set forth in SEQ ID NO: 24.

4. An anti-idiotype antibody or antigen-binding fragment thereof that binds to or recognizes an anti-GPRC5D target antibody or antigen-binding fragment thereof, wherein the anti-idiotype antibody or antigen-binding fragment thereof comprises:

a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 25; and a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 26.

5. The anti-idiotype antibody or antigen-binding fragment thereof of any one of embodiments 1, 2, and 4, wherein:

the VH region comprises a CDR-H1 comprising the amino acid sequence set forth in SEQ ID NO: 15, a CDR-H2 comprising the amino acid sequence set forth in SEQ ID NO: 16, and a CDR-H3 comprising the amino acid sequence set forth in SEQ ID NO: 17; and the VL region comprising a CDR-L1 comprising the amino acid sequence set forth in SEQ ID NO: 22, a CDR-L2 comprising the amino acid sequence set forth in SEQ ID NO: 23, and a CDR-L3 comprising the amino acid sequence set forth in SEQ ID NO: 24.

6. The anti-idiotype antibody or antigen-binding fragment thereof of any one of embodiments 3-5, wherein:

the VH region comprises an amino acid sequence having at least 90% sequence identity to the amino acid sequence set forth in SEQ ID NO: 25; and the VL region comprises an amino acid sequence having at least 90% sequence identity to the amino acid sequence set forth in SEQ ID NO: 26.

7. The anti-idiotype antibody or antigen-binding fragment thereof of any one of embodiments 3-6, wherein:

the VH region comprises the amino acid sequence set forth in SEQ ID NO: 25; and the VL region comprises the amino acid sequence set forth in SEQ ID NO: 26.

8. The anti-idiotype antibody or antigen-binding fragment thereof of any one of embodiments 1-7, wherein the anti-idiotype antibody or antigen-binding fragment thereof comprises:

a heavy chain comprising an amino acid sequence having at least 90% sequence identity to the amino acid sequence set forth in SEQ ID NO: 27; and a light chain comprising an amino acid sequence having at least 90% sequence identity to the amino acid sequence set forth in SEQ ID NO: 28.

9. The anti-idiotype antibody or antigen-binding fragment thereof of any one of embodiments 1-8, wherein the anti-idiotype antibody or antigen-binding fragment thereof comprises:

a heavy chain comprising an amino acid sequence set forth in SEQ ID NO: 27; and a light chain comprising an amino acid sequence set forth in SEQ ID NO: 28.

10. The anti-idiotype antibody or antigen-binding fragment thereof of any one of embodiments 1-9, wherein the anti-GPRC5D target antibody or antigen-binding fragment thereof comprises a VH region comprising the amino acid sequence set forth in SEQ ID NO: 7, and a VL region comprising the amino acid sequence set forth in SEQ ID NO: 8.

11. The anti-idiotype antibody or antigen-binding fragment thereof of embodiment 10, wherein the anti-GPRC5D target antibody or antigen-binding fragment thereof is a single chain fragment.

12. The anti-idiotype antibody or antigen-binding fragment thereof of embodiment 11, wherein the single chain fragment comprises a flexible linker positioned between the VH region and the VL region.

13. The anti-idiotype antibody or antigen-binding fragment thereof of embodiment 12, wherein the flexible linker comprises the amino acid sequence set forth in SEQ ID NO: 10.

14. The anti-idiotype antibody or antigen-binding fragment thereof of any one of embodiments 11-13, wherein the single chain fragment of the anti-GPRC5D target antibody or antigen binding fragment is a single chain variable fragment (scFv).

15. The anti-idiotype antibody or antigen-binding fragment thereof of embodiment 14, wherein the scFv comprises the amino acid sequence set forth in SEQ ID NO: 9.

16. The anti-idiotype antibody or antigen-binding fragment thereof of any one of embodiments 1-15, wherein the anti-idiotype antibody or antigen-binding fragment thereof binds to or recognizes an epitope within or including all or a portion of a complementarity determining region (CDR) of the anti-GPRC5D target antibody or antigen-binding fragment.

17. The anti-idiotype antibody or antigen-binding fragment thereof of any one of embodiments 1-16, wherein:

the anti-GPRC5D target antibody or antigen-binding fragment thereof is within or included in an antigen-binding domain of an extracellular portion of a chimeric antigen receptor (CAR); and/or the anti-idiotype antibody or antigen-binding fragment thereof specifically binds the anti-GPRC5D target antibody or antigen-binding fragment thereof comprised within or included in an antigen-binding domain of an extracellular portion of a CAR.

18. The anti-idiotype antibody or antigen-binding fragment thereof of any one of embodiments 14-16, wherein:

the scFv is within or included in an extracellular portion of a CAR; and/or the anti-idiotype antibody or antigen-binding fragment thereof specifically binds the scFv comprised within or included in an extracellular portion of a CAR.

19. The anti-idiotype antibody or antigen-binding fragment thereof of embodiment 17 or embodiment 18, wherein the CAR further comprises a transmembrane domain linked to the antigen-binding domain via a spacer.

20. The anti-idiotype antibody of antigen-binding fragment thereof of embodiment 19, wherein the spacer is an immunoglobulin spacer, optionally wherein the spacer comprises the amino acid sequence set forth in SEQ ID NO: 11.

21. The anti-idiotype antibody or antigen-binding fragment thereof of embodiment 19 or embodiment 20, wherein the transmembrane domain comprises a transmembrane portion of CD28, which optionally is human CD28.

22. The anti-idiotype antibody or antigen-binding fragment thereof of any one of embodiments 19-21, wherein the anti-idiotype antibody or antigen-binding fragment thereof does not bind to an epitope in the spacer domain of the CAR.

23. The anti-idiotype antibody or antigen-binding fragment thereof of any one of embodiments 1-22, wherein the anti-idiotype antibody or antigen-binding fragment thereof does not bind or does not specifically bind to CD28 or a portion thereof, which optionally is human CD28.

24. The anti-idiotype antibody or antigen-binding fragment thereof of any one of embodiments 1-23, wherein the anti-idiotype antibody or antigen-binding fragment thereof does not bind to an epitope in an Fc domain, which optionally is a human IgG1 Fc domain.

25. The anti-idiotype antibody or antigen-binding fragment thereof of any one of embodiments 1-24, wherein the anti-GPRC5D target antibody or antigen-binding fragment thereof binds to or recognizes human G Protein-Coupled Receptor Class C Group 5 Member D (GPRC5D).

26. The anti-idiotype antibody or antigen-binding fragment thereof of any one of embodiments 1-25, wherein the anti-idiotype antibody or antigen-binding fragment thereof is an agonist of a CAR comprising the anti-GPRC5D target antibody or antigen-binding fragment thereof.

27. The anti-idiotype antibody or antigen-binding fragment thereof of embodiment 26, wherein the anti-idiotype antibody or antigen-binding fragment thereof is an agonist of the CAR when immobilized to a support or a stationary phase, optionally wherein the support or stationary phase is a plate or a bead.

28. The anti-idiotype antibody or antigen-binding fragment thereof of any one of embodiments 1-27, wherein the anti-idiotype antibody or antigen-binding fragment thereof has a binding affinity (EC50) and/or a dissociation constant to the anti-GPRC5D target antibody or antigen-binding fragment thereof that is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM.

29. The anti-idiotype antibody or antigen-binding fragment thereof of any one of embodiments 1-28, which is humanized.

30. The anti-idiotype antibody or antigen-binding fragment thereof of any one of embodiments 1-29, which is recombinant.

31. The anti-idiotype antibody or antigen-binding fragment thereof of any one of embodiments 1-30, which is monoclonal.

32. The anti-idiotype antibody or antigen-binding fragment thereof of any one of embodiments 1-31, which is an antigen-binding fragment.

33. The anti-idiotype antibody or antigen-binding fragment thereof of embodiment 32, wherein the antigen-binding fragment is selected from among Fab fragments, F(ab')2 fragments, Fab' fragments, Fv fragments, an scFv, or a single domain antibody.

34. The anti-idiotype antibody or antigen-binding fragment thereof of any one of embodiments 1-33, comprising at least a portion of an immunoglobulin constant region.

35. The anti-idiotype antibody or antigen-binding fragment thereof of embodiment 34, wherein the at least a portion of an immunoglobulin constant region comprises an Fc region or a portion of the Fc comprising the CH2 and CH3 domains.

36. The anti-idiotype antibody or antigen-binding fragment thereof of embodiment 34 or embodiment 35, wherein the constant region is derived from human IgG.

37. The anti-idiotype antibody or antigen-binding fragment thereof of any one of embodiments 34-36, which is an intact antibody or full-length antibody.

38. A conjugate, comprising the anti-idiotype antibody or antigen-binding fragment thereof of any one of embodiments 1-37 and a heterologous molecule or moiety.

39. The conjugate of embodiment 38, wherein the heterologous molecule or moiety is a label.

40. The conjugate of embodiment 39, wherein the label is selected from a fluorescent dye, a fluorescent protein, a radioisotope, a chromophore, a metal ion, a gold particle, a silver particle, a magnetic particle, a polypeptide, an enzyme, a streptavidin, a biotin, a luminescent compound or an oligonucleotide.

41. The conjugate of embodiment 39, wherein the heterologous molecule or moiety is a protein, peptide, nucleic acid or small molecule, which optionally is or comprises a toxin or a Strep-Tag.

42. A nucleic acid molecule(s) encoding the heavy chain and/or the light chain of the anti-idiotype antibody or antigen-binding fragment thereof of any one of embodiments 1-37.

43. The nucleic acid molecule(s) of embodiment 42, comprising:

a sequence of nucleotides encoding (i) the heavy chain variable region set forth in SEQ ID NO: 25, (ii) a heavy chain variable region that has at least 90% sequence identity to the amino acid sequence set forth in SEQ ID NO: 25; or (iii) a degenerate sequence of (i) or (ii); and a sequence of nucleotides encoding (iv) the light chain variable region set forth in SEQ ID NO: 26, (v) a light chain variable region that has at least 90% sequence identity to the amino acid sequence set forth in SEQ ID NO: 26; or (vi) a degenerate sequence of (iv) or (v).

44. The nucleic acid molecule(s) of embodiment 42, comprising:

a sequence of nucleotides encoding (i) the heavy chain set forth in SEQ ID NO: 27, (ii) a heavy chain that has at least 90% sequence identity to the amino acid sequence set forth in SEQ ID NO: 27; or (iii) a degenerate sequence of (i) or (ii); and a sequence of nucleotides encoding (iv) the light chain set forth in SEQ ID NO: 28, (v) a light chain that has at least 90% sequence identity to the amino acid sequence set forth in SEQ ID NO: 28; or (vi) a degenerate sequence of (iv) or (v).

45. The nucleic acid molecule(s) of any one of embodiments 42-44, wherein the nucleotide sequence encoding the heavy chain and/or light chain comprises a signal sequence.

46. The nucleic acid molecule(s) of any one of embodiments 42-45, wherein the nucleic acid molecule(s) comprise one or more nucleotide sequences selected from the group consisting of SEQ ID NOs: 29-32.

47. A vector, comprising the nucleic acid molecule(s) of any one of embodiments 42-46.

48. A cell, comprising the anti-idiotype antibody or antigen-binding fragment thereof of any one of embodiments 1-37, the nucleic acid molecule of any one of embodiments 42-46, or the vector of embodiment 47.

49. A method of producing an anti-idiotype antibody or antigen-binding fragment thereof, comprising expressing the heavy and/or light chain encoded by the nucleic acid molecule(s) of any one of embodiments 42-45 or the vector of embodiment 47 in a suitable host cell; and recovering or isolating the antibody.

50. A method of producing an anti-idiotype antibody or antigen-binding fragment thereof, comprising culturing the cell of embodiment 48 under conditions in which the heavy chain and/or light chain is expressed; and recovering or isolating the antibody.

51. An anti-idiotype antibody or antigen-binding fragment thereof produced by the method of embodiment 49 or embodiment 50.

52. A composition, comprising the anti-idiotype antibody or antigen-binding fragment thereof of any one of embodiments 1-37, the conjugate of any one of embodiments 38-41, or the cell of embodiment 48.

53. The composition of embodiment 52, further comprising a pharmaceutically acceptable excipient.

54. A kit, comprising one or more of the anti-idiotype antibody or antigen-binding fragment thereof of any one of embodiments 1-37, the conjugate of any one of embodiments 38-41, the nucleic acid molecule(s) of any one of embodiments 42-45, and, optionally, instructions for use.

55. The kit of embodiment 54, further comprising a reagent or support for immobilizing the anti-idiotype antibody or antigen-binding fragment thereof or the conjugate, wherein said reagent or support is a bead, a column, a microwell, a stick, a filter, a strip or a soluble oligomeric streptavidin mutein reagent.

56. A method of detecting a target antibody or antigen-binding fragment thereof, comprising:

(a) contacting a composition comprising a target antibody or antigen-binding fragment thereof with the anti-idiotype antibody or antigen-binding fragment thereof of any one of embodiments 1-37 or the conjugate of any one of embodiments 38-41 that specifically binds to the target antibody or antigen-binding fragment thereof; and (b) detecting the anti-idiotype antibody bound to the target antibody or antigen-binding fragment thereof.

57. The method of embodiment 56, wherein the target antibody or antigen-binding fragment thereof is bound to a cell or expressed on the surface of a cell and detecting in (b) comprises detecting cells bound with the anti-idiotype antibody or antigen-binding fragment thereof.

58. The method of embodiment 57, wherein the cell expresses on its surface a CAR comprising the target antibody or antigen-binding fragment thereof.

59. A method of detecting a CAR comprising a target antibody or antigen-binding fragment thereof, comprising:

(a) contacting a cell expressing a CAR comprising a target antibody or antigen-binding fragment thereof with the anti-idiotype antibody or antigen-binding fragment thereof of any one of embodiments 1-37, or the conjugate of any one of embodiments 38-41, that specifically binds to the target antibody or antigen-binding fragment thereof; and (b) detecting cells bound with the anti-idiotype antibody or antigen-binding fragment thereof.

60. The method of embodiment 59, wherein the anti-idiotype antibody or antigen-binding fragment thereof is directly or indirectly labeled for detection.

61. A method of selecting cells from a cell population, comprising:

(a) contacting a cell population expressing a CAR comprising a target antibody or antigen-binding fragment thereof or a cell bound to a target antibody or antigen-binding fragment thereof with the anti-idiotype antibody or antigen-binding fragment thereof of any one of embodiments 1-37, or the conjugate of any one of embodiments 38-41, that specifically binds to the target antibody or antigen-binding fragment thereof; and (b) selecting cells bound with the anti-idiotype antibody or antigen-binding fragment thereof.

62. The method of embodiment 61, wherein the cells bound with the anti-idiotype antibody or antigen-binding fragment thereof are selected by affinity-based separation.

63. The method of embodiment 62, wherein the affinity-based separation is immunoaffinity-based separation.

64. The method of embodiment 62 or embodiment 63, wherein the affinity-based separation is by flow cytometry.

65. The method of embodiment 62 or embodiment 63, wherein the affinity-based separation is by magnetic activated cell sorting.

66. The method of embodiment 62 or embodiment 63, wherein the affinity-based separation comprises affinity chromatography.

67. The method of embodiment 65 or embodiment 66, wherein the anti-idiotype antibody or antigen-binding fragment thereof is reversibly bound or immobilized to a support or a stationary phase.

68. A method of stimulating cells, comprising incubating an input composition comprising cells expressing a CAR comprising a target antibody or antigen-binding fragment thereof with the anti-idiotype antibody or antigen-binding fragment thereof of any one of embodiments 1-37, or the conjugate of any one of embodiments 38-41, that specifically binds to the target antibody or antigen-binding fragment thereof, thereby generating an output composition comprising stimulated cells.

69. A method of producing a cell composition, comprising:

(a) introducing into cells a nucleic acid molecule(s) encoding a CAR, thereby generating an input composition; and (b) incubating the input composition with the anti-idiotype antibody or antigen-binding fragment thereof of any one of embodiments 1-37, or the conjugate of any one of embodiments 38-41, that specifically binds to an antigen receptor of the CAR, thereby producing the cell composition.

70. The method of embodiment 69, wherein the introducing in (a) comprises introducing the nucleic acid molecule(s) into the cells by viral transduction, transposition, electroporation, or chemical transfection.

71. The method of embodiment 69 or embodiment 70, wherein the introducing in (a) comprises introducing the nucleic acid molecule(s) in the cells by transduction with a viral vector comprising the nucleic acid molecule(s), optionally wherein the viral vector is a retroviral vector or a lentiviral vector.

72. The method of embodiment 69 or embodiment 70, wherein the introducing in (a) comprises introducing the nucleic acid molecule(s) in the cells by transposition with a transposon comprising the nucleic acid molecule(s).

73. The method of embodiment 69 or embodiment 70, wherein the introducing in (a) comprises introducing the nucleic acid molecule(s) in the cells by electroporation or transfection of a vector comprising the nucleic acid molecule(s).

74. The method of any one of embodiments 69-73, further comprising a step of activating the cells prior to step (a).

75. The method of embodiment 74, wherein the step of activating the cells comprises contacting the cells with an agonist of CD3 and optionally an agonist of CD28.

76. The method of embodiment 75, wherein the step of activating the cells comprises contacting the cells with a reagent comprising agonistic anti-CD3 and anti-CD28 antibodies.

77. The method of any one of embodiments 69-76, wherein the incubation is performed under conditions in which the anti-idiotype antibody or antigen-binding fragment thereof binds to the CAR, thereby inducing or modulating a signal in one or more cells in the input composition.

78. The method of any one of embodiments 69-77, wherein the cells comprise T cells.

79. The method of embodiment 78, wherein the T cells comprise CD4+ and/or CD8+ T cells.

80. The method of any one of embodiments 69-79, wherein the anti-idiotype antibody or antigen-binding fragment thereof is immobilized to a solid support, which optionally comprises or is conjugated to a reagent comprising a plurality of binding sites capable of reversibly binding to the anti-idiotype antibody or antigen-binding fragment thereof.

81. The method of any one of embodiments 69-79, wherein the anti-idiotype antibody or antigen-binding fragment thereof is immobilized to a soluble reagent, which optionally is or comprises a plurality of binding sites capable of reversibly binding to the anti-idiotype antibody or antigen-binding fragment thereof.

82. The method of embodiment 80 or embodiment 81, wherein the reagent comprises a streptavidin mutein.

83. The method of any one of embodiments 69-82, wherein the incubation is for at least or about at least 5 minutes, 10 minutes, 30 minutes, 60 minutes, 2 hours, 6 hours, 12 hours, 24 hours, 36, 48 hours, 72 hours or 96 hours.

84. The method of any one of embodiments 69-83, wherein the input composition comprises less than or less than about 60%, less than or less than about 50%, less than or less than about 40%, less than or less than about 30%, less than or less than about 20% or less than or less than about 10% CAR-expressing cells as a percentage of the total cells in the composition.

85. The method of any one of embodiments 69-84, wherein:

the number of CAR-expressing cells in the output composition is increased by greater than 1.2-fold, 1.5-fold, 2.0-fold, 3.0-fold, 4.0-fold, 5.0-fold, 10-fold or more compared to the number of CAR-expressing cells in the input composition; and/or the percentage of CAR-expressing in the output composition compared to the total cells in the composition is increased by greater than 10%, 20%, 40%, 50%, 60%, 70%, 80%, or more.

86. The method of any one of embodiments 69-85, wherein prior to the introducing and/or incubating the cells are not selected or enriched for CAR-expressing cells.

87. A method of purifying an anti-idiotype antibody or antigen-binding fragment thereof, comprising:

(a) contacting a composition comprising a target antibody or antigen-binding fragment thereof with the anti-idiotype antibody or antigen-binding fragment thereof of any one of embodiments 1-37, or the conjugate of any one of embodiments 38-41, that specifically binds to a target antibody or antigen-binding fragment thereof, and (b) isolating complexes comprising the anti-idiotype antibody or antigen-binding fragment thereof.

88. The method of embodiment 87, wherein the complexes comprising the anti-idiotype antibody or antigen-binding fragment thereof are isolated by affinity-based separation.

89. The method of embodiment 88, wherein the affinity-based separation is immunoaffinity-based separation.

90. The method of embodiment 89, wherein the affinity-based separation is magnetic-based separation.

91. The method of embodiment 89, wherein the affinity-based separation comprises affinity chromatography.

92. A method of depleting cells, comprising administering, to a subject, a composition comprising the anti-idiotype antibody or antigen-binding fragment thereof of any one of embodiments 1-37, or the conjugate of any one of embodiments 38-41, that specifically binds to a target antibody or antigen-binding fragment thereof, wherein the subject has been administered a cell expressing a CAR comprising the target antibody or antigen-binding fragment thereof.

93. The method of embodiment 92, wherein the depletion occurs via antibody-dependent cell-mediated cytotoxicity (ADCC).

94. The method of any one of embodiments 56-93, wherein the target antibody or antigen-binding fragment thereof is a single chain fragment.

95. The method of embodiment 94, wherein the single chain fragment comprises an scFv.

96. The method of any one of embodiments 56-95, wherein the target antibody or antigen-binding fragment thereof comprises a VH region comprising the amino acid sequence set forth in SEQ ID NO: 7, and a VL region comprising the amino acid sequence set forth in SEQ ID NO: 8.

97. The method of embodiment 96, wherein the target antibody or antigen-binding fragment thereof is an scFv and the VH region and the VL region are joined by a flexible linker.

98. The method of embodiment 97, wherein the flexible linker comprises the amino acid sequence set forth in SEQ ID NO: 10, and the scFv comprises the amino acid sequence set forth in SEQ ID NO: 9.

99. An article of manufacture comprising the anti-idiotype antibody or antigen-binding fragment thereof of any one of embodiments 1-37, or the conjugate of any one of embodiments 38-41, and instructions for using the anti-idiotype antibody or antigen-binding fragment thereof to:

detect a target antibody or antigen-binding fragment thereof or a CAR comprising a target antibody or antigen-binding fragment thereof; and/or select or enrich, from a population of cells, engineered cells expressing a CAR comprising the target antibody or antigen-binding fragment thereof; and/or stimulate an input composition comprising cells expressing a CAR comprising the target antibody or antigen-binding fragment thereof.

100. An article of manufacture comprising:

a binding reagent comprising an extracellular domain of a CAR comprising a target antibody or antigen-binding fragment thereof, said extracellular domain or portion thereof comprising the target antibody or antigen-binding fragment thereof; and an anti-idiotype antibody or antigen-binding fragment of any of embodiments 1-37, or the conjugate of any one of embodiments 38-41.

101. The article of manufacture of embodiment 100, wherein the binding reagent is a first binding reagent and the article of manufacture further comprises a second binding reagent comprising the extracellular domain or portion thereof of the CAR.

102. The article of manufacture of embodiment 100 or embodiment 101, wherein the extracellular domain of the CAR or portion thereof of the first and second binding reagent is the same.

103. The article of manufacture of any of embodiments 100-102, further comprising instructions for using the binding reagent, optionally the first and second binding reagent, for assaying a sample for the presence or absence of a molecule that binds to the binding reagent using an immunoassay, optionally wherein the immunoassay is a bridge or sandwich immunoassay, optionally wherein the sample is from a subject having been administered a cell therapy comprising cells engineered with a CAR comprising a target antibody that is the or antigen-binding fragment thereof.

104. The article of manufacture of any of embodiments 100-103, wherein the binding reagent, optionally the first and/or second binding reagent, is detectably labeled or capable of producing a detectable signal.

105. The article of manufacture of any of embodiments 101-104, wherein one of the first and second binding reagent is attached to a solid support of is capable of being attached to a solid support and the other of the first and second binding reagent is detectable label or is capable of producing a detectable signal.

106. The article of manufacture of embodiment 105, wherein the article of manufacture further comprises a solid support, optionally wherein the one of the first and second binding reagent is linked, directly or indirectly to biotin, and the solid support comprises a streptavidin-coated surface.

107. The article of manufacture of any one of embodiments 99-106, wherein the target antibody or antigen-binding fragment thereof is a single chain fragment.

108. The article of manufacture of embodiment 107, wherein the single chain fragment comprises an scFv.

109. The article of manufacture of any one of embodiments 99-108, wherein the target antibody or antigen-binding fragment thereof comprises a VH region comprising the amino acid sequence set forth in SEQ ID NO: 7, and a VL region comprising the amino acid sequence set forth in SEQ ID NO: 8.

110. The article of manufacture of embodiment 109, wherein the target antibody or antigen-binding fragment thereof is an scFv and the VH region and the VL region are joined by a flexible linker.

111. The article of manufacture of embodiment 110, wherein the flexible linker comprises the amino acid sequence set forth in SEQ ID NO: 10, and the scFv comprises the amino acid sequence set forth in SEQ ID NO: 9.

VIII. EXAMPLES

The following examples are included for illustrative purposes only and are not intended to limit the scope of the invention.

Example 1: Generation and Assessment of Anti-Idiotype Antibodies Against Anti-GPRC5D Chimeric Antigen Receptors Anti-idiotypic antibodies that recognize the scFv portion of an exemplary anti-GPRC5D chimeric antigen receptor (CAR) were generated and assessed. Amino acid sequences (SEQ ID NOs) of an exemplary anti-idiotypic antibody that was generated is listed in Table E1.

TABLE E1

Amino acid sequences (SEQ ID NOs) of an exemplary anti-idiotypic antibody clone.

| Clone ID | VH | VL | Heavy Chain | Light Chain | Kabat CDR-H1 H2 H3 | Kabat CDR-L1 L2 L3 | Chothia CDR-H1 H2 H3 | Chothia CDR-L1 L2 L3 | AbM CDR-H1 H2 H3 | AbM CDR-L1 L2 L3 |
|---|---|---|---|---|---|---|---|---|---|---|
| 8 | 25 | 26 | 27 | 28 | 15 16 17 | 22 23 24 | 18 19 17 | 22 23 24 | 20 21 17 | 22 23 24 |

A. Anti-ID Antibodies Against an Anti-GPRC5D CAR

Anti-idiotype antibodies (anti-IDs) recognizing the scFv portion of an exemplary anti-GPRC5D antibody were generated. The anti-GPRC5D CAR contained an anti-GPRC5D scFv with variable heavy and variable light chain regions derived from an anti-GPRC5D antibody (having a variable light region and a variable heavy region sequence of SEQ ID NO: 8 and 7, respectively, separated by a linker set forth in SEQ ID NO: 10; scFv sequence set forth in SEQ ID NO: 9), a human IgG-derived spacer (SEQ ID NO: 11), a human CD28-derived transmembrane domain (SEQ ID NO: 12), a human 4-1BB-derived intracellular signaling domain (SEQ ID NO: 13), and a human CD3 zeta-derived signaling domain (SEQ ID NO: 14).

Mice were immunized with the anti-GPRC5D scFv fused to a mouse Fc. Immune cells were isolated from spleens of immunized mice, and antibody-producing spleen cells were fused with tumor cells (e.g., myeloma cells) to produce hybridoma fusion cells. Hybridoma cells were clonally expanded, and supernatant was screened by ELISA for binding to the recombinant soluble scFv-Fc and by flow cytometry for binding to anti-GPRC5D CAR-expressing cells. Supernatant from hybridoma clones were counter-screened by ELISA against a non-target scFv-Fc and by flow cytometry against cells expressing a non-target CAR. Each selected hybridoma clone was expanded and antibody purified for further characterization.

B. Assessment of Binding of Anti-Idiotypic Antibody to Anti-GPRC5D CAR by Flow Cytometry Anti-ID antibody clones were assessed for the ability to specifically bind to T cells engineered with the anti-GPRC5D CAR, to identify candidate clones that can be suitable for use in flow cytometry. $1\times10^5$ Jurkat T cells engineered to express the anti-GPRC5D CAR, or an unrelated control CAR specific for a different antigen (Control CAR), or non-engineered (parental) Jurkat cells, were incubated with 2.5 pg/mL of one of 10 anti-ID antibody clones (clones 1, 2, 3, 4, 5, 6, 7, 8, 9, and 10) conjugated to Alexa Fluor®647 fluorophore for 20 minutes at 4° C. The cells were washed 2x with FACS buffer, resuspended in 150p of FACS buffer, and subject to flow cytometry analysis. Clone 1 is an anti-idiotype antibody against Control CAR.

As shown in FIG. 1A, the mean fluorescence intensity (MFI) was determined in two separate experiments (Experiment #1 and Experiment #2), and clones 7, 8, 9, and 10 were observed to exhibit the highest MFI among the clones tested.

Figure 1B:
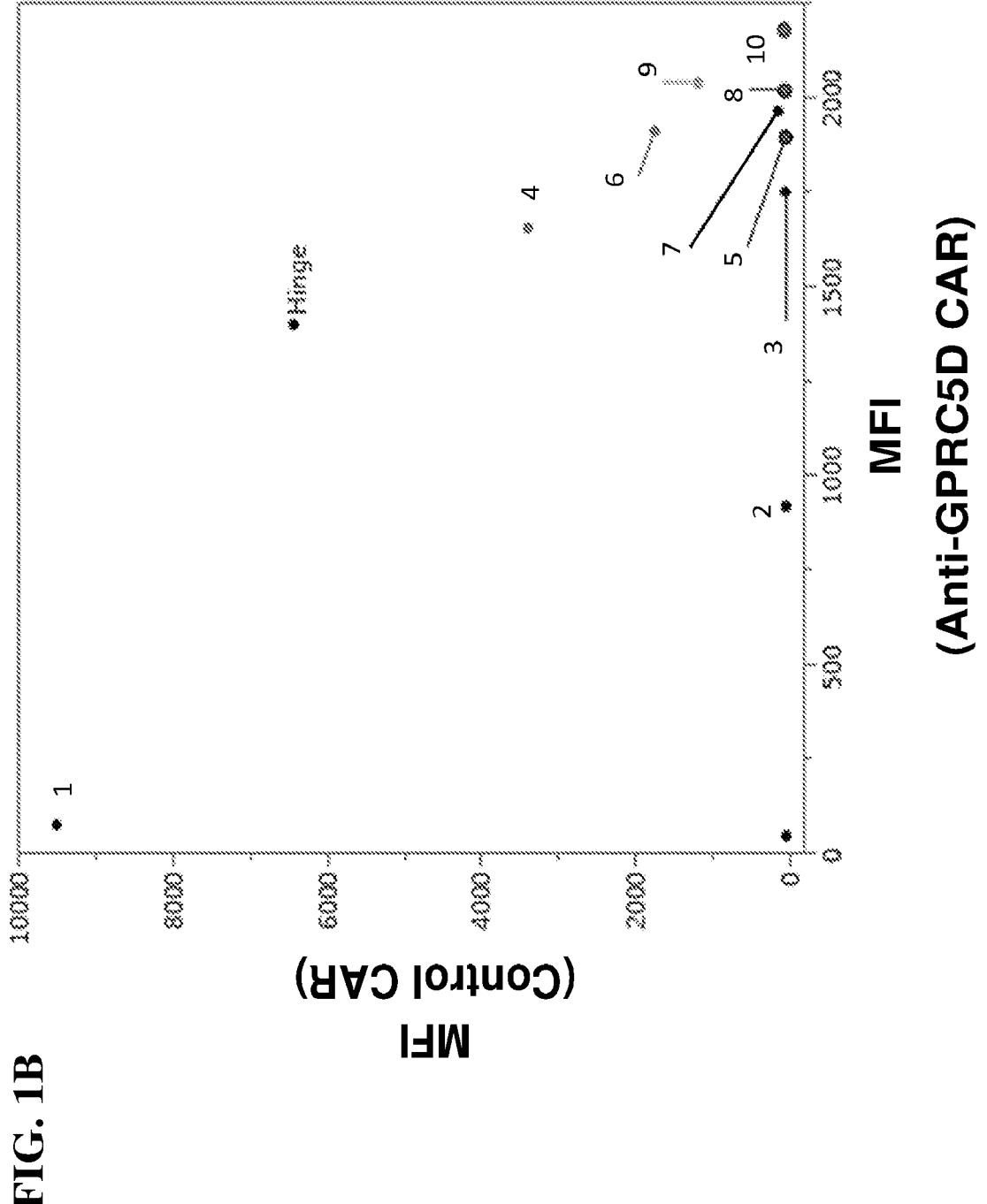

As shown in FIG. 1B, clone 8 was observed to exhibit among the highest MFI for the anti-GPRC5D CAR among the clones tested, and was observed to exhibit among the lowest MFI for the Control CAR among the clones tested. This demonstrates that clone 8 exhibits unique features suitable for use in specifically detecting the anti-GPRC5D CAR.

C. Assessment of T Cell Stimulation Agonistic Activity of Soluble or Plate-Bound Anti-Idiotype Antibodies Various anti-ID antibody clones described above were tested for their agonistic activity for T cell stimulation, using a reporter cell line.

A reporter cell line was generated containing a Nur77-tdTomato knock-in reporter, where the nucleic acid sequences encoding a tdTomato fluorescent protein was knocked-in at the endogenous Nur77 locus. Orphan nuclear hormone receptor Nur77 (also called Nr4a1) is an immediate-early response gene induced by activation of signal from the T cell receptor and/or via molecules containing immunoreceptor tyrosine-based activation motif (ITAM). A nucleic acid sequence encoding tdTomato was targeted for integration in-frame with the endogenous Nur77 gene at the final exon, prior to the stop codon, by introducing a genetic disruption using gene editing and targeting the nucleic acid sequence encoding tdTomato for integration at a site near the genetic disruption by homology-dependent repair (HDR).

The Nur77-tdTomato reporter cell line was engineered to express the anti-GPRC5D CAR, or Control CAR, and reporter expression was assessed after incubation with a soluble anti-ID antibody or a plate-bound anti-ID antibody. For assessing soluble anti-ID antibodies, a multi-well plate was blocked overnight with phosphate buffer saline (PBS) and 10% fetal bovine serum (FBS). 2.5 pg/mL of one of 10 anti-ID antibody clones (clones 1, 2, 3, 4, 5, 6, 7, 8, 9, and 10) in RPMI media with 10% FBS was added to the plate. For assessing plate-bound anti-ID antibodies, a multi-well plate was coated with 2.5 pg/mL of one of the anti-ID antibody clones in PBS overnight at 4° C. or 4 hours at 37° C., followed by washing with RPMI media with 10% FBS. $1 \times 10^5$ Nur77-tdTomato reporter cells were added to each well and incubated at 37° C. for 20 hours. The samples were stained with 4',6-diamidino-2-phenylindole (DAPI), and assessed by flow cytometry for DAPI staining and tdTomato fluorescence intensity.

Figure 2A:
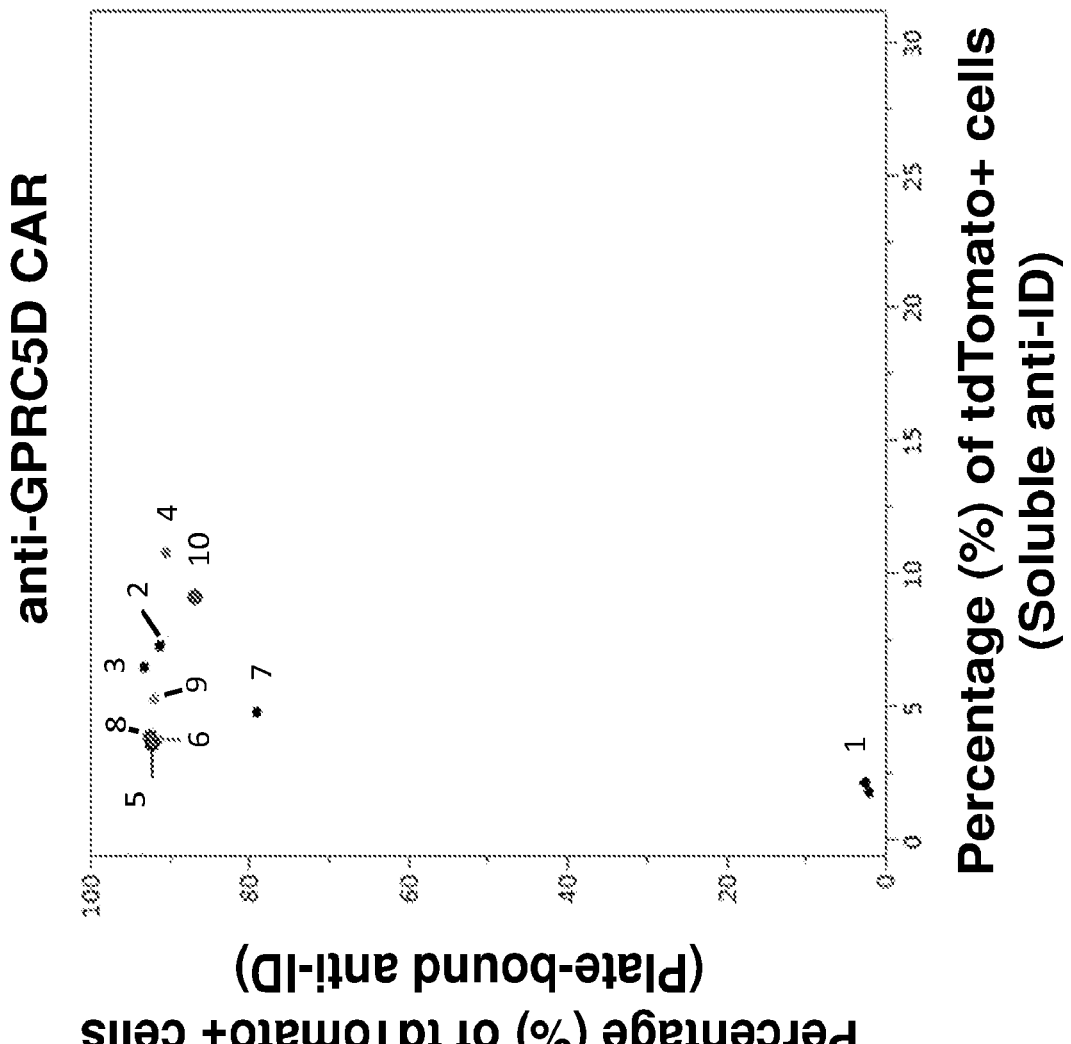
FIGS. 2A-2B depict the results of assays that tested certain anti-ID antibodies for their agonistic activity for T cell stimulation, using a reporter cell line engineered with the anti-GPRC5D CAR, or the Control CAR, which was incubated with a soluble anti-ID antibody or a plate-bound anti-ID antibody.
Figure 2B:
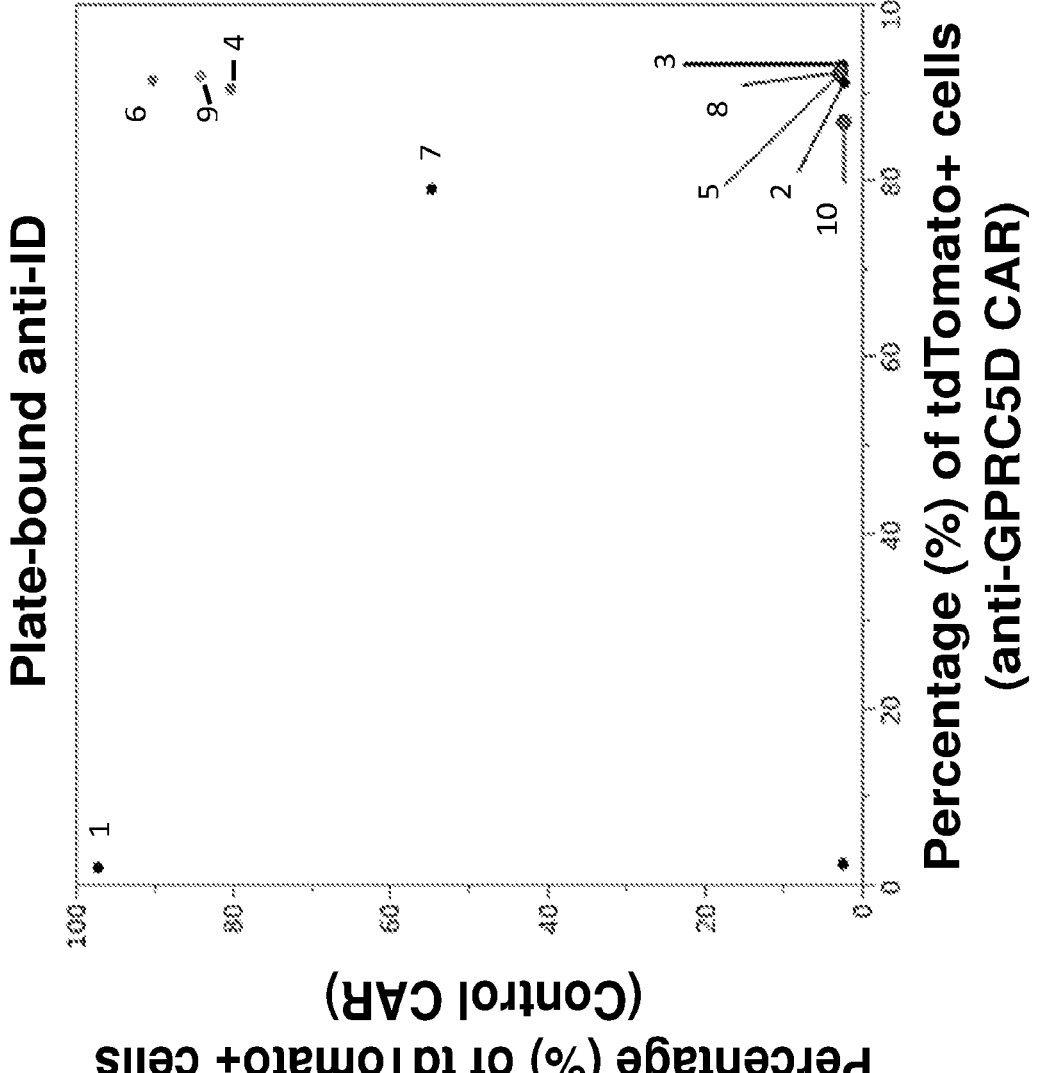

The results are shown in FIGS. 2A-2B. As shown in FIG. 2A, incubation with each of the plate-bound anti-ID clones resulted in a high percentage of tdTomato+ cells expressing the anti-GPRC5D CAR, with the exception of clone 1 that is an anti-idiotype antibody against Control CAR. This demonstrates that each of these clones, with the exception of clone 1, exhibit agonistic activity in plate-bound form. Incubation with soluble anti-ID clones resulted in a smaller percentage of tdTomato+ cells expressing the anti-GPRC5D CAR, which demonstrated that these clones exhibit relatively weak agonistic activity in soluble form. As shown in FIG. 2B, the plate-bound clones 2, 3, 5, 8, and 10 exhibited a low percentage of tdTomato+ cells expressing the Control CAR, which was observed to be less than approximately 5% of the cells for each of those clones, and exhibited a high percentage of tdTomato+ cells expressing the anti-GPRC5D CAR, which was observed to be greater than approximately 85% of the cells for each of those clones.

Example 2: Assessment of CAR Binding of Candidate Anti-Idiotype Antibody in Primary T Cells A candidate anti-idiotype antibody (clone 8) was assessed for its ability to specifically bind to T cells engineered to express the exemplary anti-GPRC5D CAR described in Example 1. To generate anti-GPRC5D CAR-T cells, primary human T cells were isolated from whole blood and stimulated with anti-CD3/anti-CD28 magnetic beads for 72 hours in the presence of recombinant IL-2, IL-7, and IL-15. T cells were transduced on days 2 to 3 after initiation of the stimulation by spinoculation with virus encoding the exemplary anti-GPRC5D CAR, cultivated under conditions for expansion, harvested, and cryopreserved.

After engineering, aliquots of $5 \times 10^5$ anti-GPRC5D CAR-T or mock-processed T cells from five healthy donors were analyzed for CAR expression by flow cytometry. To test for specificity of CAR binding by anti-ID clone 8, clone 8 binding to primary T cells transduced to express a non-target anti-BCMA CAR was also assessed. The non-target anti-BCMA CAR contained an anti-BCMA scFv, an immunoglobulin spacer, a human CD28-derived transmembrane domain, a human 4-1BB-derived intracellular signaling domain, and a human CD3 zeta-derived signaling domain.

Cells were incubated with 1.25 pg/mL of clone 8 conjugated to a fluorescent dye Alexa Fluor™ 488, and flow cytometry events were collected on a FACSymphony™ flow cytometer (BD Biosciences, San Jose, CA). Data was analyzed with FlowJo™ Software (Treestar Inc., Ashland, OR).

Figure 3:
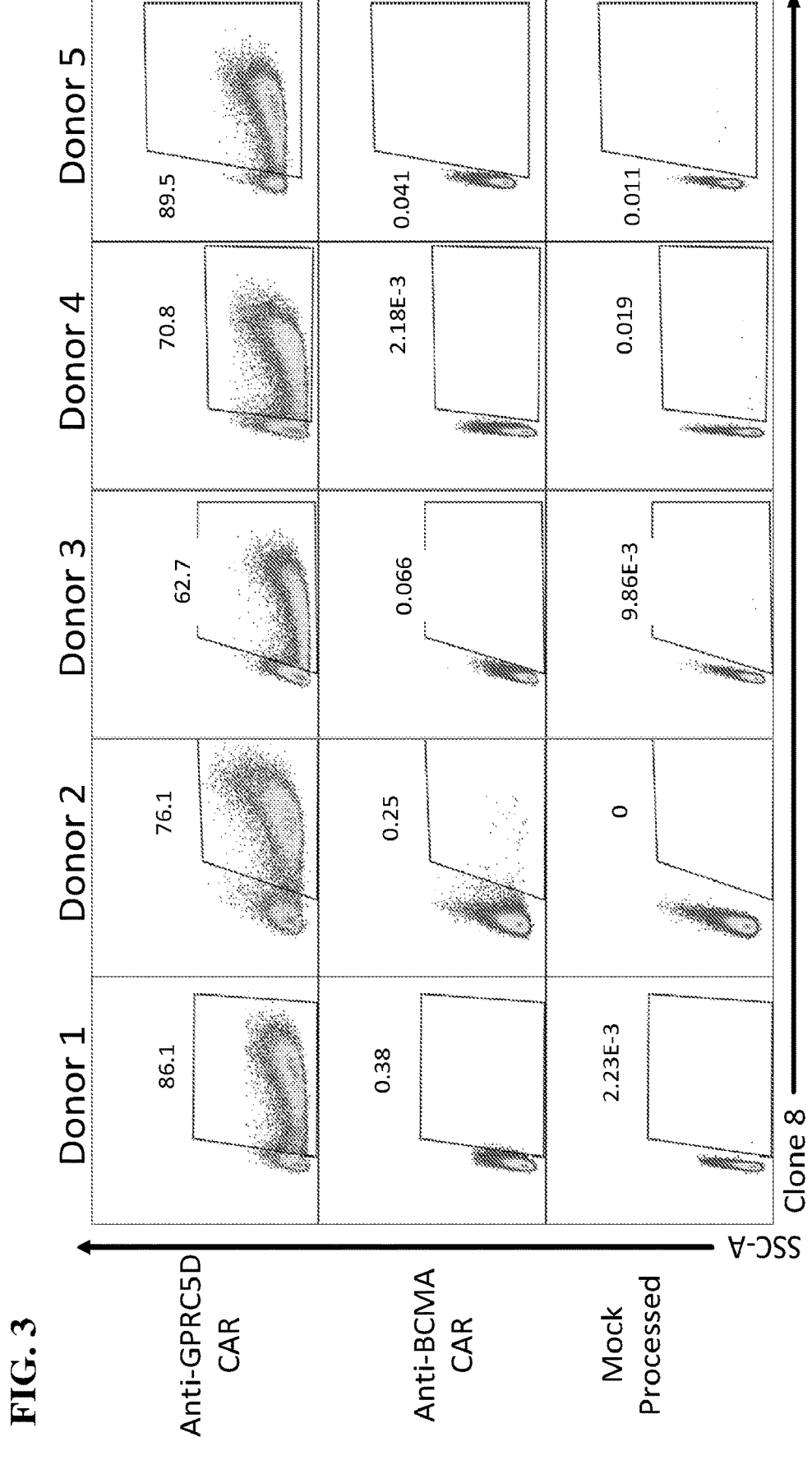
FIG. 3 depicts the results of assays that tested a candidate anti-ID antibody for its ability to specifically bind to primary T cells engineered to express the anti-GPRC5D CAR.

FIG. 3 shows the flow cytometry results for fluorophore-conjugated clone 8 binding against anti-GPRC5D CAR-T cells, anti-BCMA CAR-T cells, and mock-processed T cells. The number shown for each sample indicates the percentage of cells bound to clone 8. As shown, clone 8 binding was highly specific to T cells expressing the exemplary anti-GPRC5D CAR. Across samples, greater than 60% of cells engineered to express the anti-GPRC5D CAR showed positive labelling by anti-ID clone 8. In contrast, less than 0.5% of mock-processed T cells or anti-BCMA CAR-T cells showed positive labelling.

These results demonstrate that anti-ID clone 8 is able to specifically bind to primary T cells expressing the exemplary anti-GPRC5D CAR.

Example 3: Measuring CAR Expression Using Candidate Anti-Idiotype Antibody in Cartridge-Based Flow System The use of a candidate anti-idiotype antibody (clone 8) for measuring anti-GPRC5D CAR expression in a cartridge-based flow system (Accellix) was assessed. To test for specificity, clone 8 binding was analyzed for primary T cells transduced to express the exemplary anti-GPRC5D CAR described in Example 1 as well as for primary T cells transduced to express non-target antigen receptors, including non-GPRC5D targeting CARs (containing an scFv directed against CD19 or BCMA) or an engineered TCR. To test for linearity of CAR detection frequency using anti-ID clone 8 in the cartridge-based flow system, serially diluted samples of primary T cells expressing the exemplary anti-GPRC5D CAR were also prepared and analyzed.

To generate anti-GPRC5D CAR-T cells, primary human T cells were isolated from apheresis material and stimulated with anti-CD3/anti-CD28 magnetic beads for 24 hours in the presence of recombinant IL-2, IL-7, and IL-15. T cells were transduced one day after initiation of the stimulation by spinoculation with virus encoding the exemplary anti-GPRC5D CAR, cultivated under conditions for expansion, harvested, and cryopreserved.

To prepare cell samples for testing, vials containing the cryopreserved anti-GPRC5D CAR-T cell compositions were thawed, mixed, and assessed for CAR expression using the cartridge-based flow system. For analysis, approximately 40 µL of cell sample was dispensed into a dried-down reagent tube containing the fluorescently labeled anti-ID clone 8 or into a dried-down reagent tube that lacked the fluorescently labeled anti-ID clone 8 antibody as the fluorescence minus one (FMO) control. Both the sample and FMO control dried-down reagent tubes also contained the same additional fluorescently-labeled antibodies for multi-color flow cytometry detection of other T cell markers (e.g. CD3 or CD45) and for staining for viable cells. The reagent tube was pulse vortexed for two minutes, and 15 µL of FMO sample were transferred to a flow cartridge. The cartridge was then inserted into an Accellix benchtop instrument for signal acquisition and spectral analyses.

For all subsequent analyses, cells were gated to exclude fluorescent quality control beads and dead cells, and CD3 and CAR expression were measured as percentages of viable CD45+ cells in full stain samples. FMO samples were used to set CD3+ CAR+ gates, which were adjusted so that the frequency of CAR expression in the FMO samples was approximately 0.07-0.15% (% parent population).

A. Binding Specificity of Candidate Anti-Idiotype Antibody

To test the binding specificity of clone 8 for the exemplary anti-GPRC5D CAR, FMO and full stain samples were prepared and analyzed as described above.

Results showed that on average, 52.94% of viable CD45+ primary T cells engineered to express the exemplary anti-GPRC5D CAR showed positive staining by fluorophore-conjugated clone 8 across tested samples. In contrast, mock-transduced or cells transduced with non-target antigen receptors showed less than 0.5% CAR frequency. These results demonstrate the specificity of anti-ID clone 8 for detection of the exemplary anti-GPRC5D CAR.

B. Linearity of CAR Detection Frequency Using Candidate Anti-Idiotype Antibody

To assess linearity, FMO and full stain samples were prepared and analyzed as described above using a cell sample containing primary T cells expressing the exemplary anti-GPRC5D CAR. The frequency of CD3+ and CD3+ CAR+ cells among viable CD45+ cells of the undiluted cell sample was first assessed. Based on this measurement, expected CD3+ and CD3+ CAR+ frequencies were calculated for eight sample dilution points (90%, 80%, 70%, 30%, 10%, 5%, 2%, and 1% cell sample), after which the cell sample was diluted and analyzed for observed CD3+ and CD3+ CAR+ frequencies. For dilution, CD3-depleted, non-CAR expressing, cryopreserved apheresis product was used as the diluent matrix. Two dilution series were performed, and observed frequencies were averaged prior to subsequent analyses. Linearity of CD3+ and CD3+ CAR+ detection was assessed based on the correlation of expected and observed frequencies.

Table E4 shows the expected and observed frequencies of CD3+ cells among viable CD45+ cells. Based on these values, the coefficient of correlation ($r^2$) value was 0.999, with the best-fit line having a slope of 1.013 and a y-intercept of −1.032.

TABLE E4

| Expected and Observed CD3+ Detection Frequencies (% of Viable CD45+ Cells) | | |
|---|---|---|
| Dilution Point (% Cell Sample) | Observed CD3+ | Expected CD3+ |
| 0 (Neat diluent) | 1.58 | N/A |
| 1 | 4.34 | 2.572 |
| 2 | 4.09 | 3.57 |
| 5 | 7.78 | 6.56 |
| 10 | 12.94 | 11.55 |
| 30 | 32.86 | 31.49 |
| 70 | 69.35 | 71.37 |
| 80 | 81.69 | 81.34 |
| 90 | 91.91 | 91.31 |
| 100 | 99.70 | N/A |

Table E5 shows the expected and observed frequencies of CD3+ CAR+ cells among viable CD45+ cells. Based on these values, the $r^2$ value was 0.996, with the best-fit line having a slope of 0.9931 and a y-intercept of 0.2521.

TABLE E5

| Expected and Observed CD3+ CAR+ Detection Frequencies (% of Viable CD45+ Cells) | | |
|---|---|---|
| Dilution Point (% Cell Sample) | Observed CD3+ CAR+ | Expected CD3+ CAR+ |
| 0 (Neat diluent) | 0.02 | N/A |
| 1 | 0.69 | 0.66 |
| 2 | 1.23 | 1.31 |
| 5 | 2.96 | 3.29 |
| 10 | 6.67 | 6.57 |
| 30 | 20.17 | 19.71 |
| 70 | 43.28 | 45.99 |
| 80 | 50.65 | 52.56 |
| 90 | 62.84 | 59.13 |
| 100 | 65.71 | N/A |

Abbreviations: N/A (not applicable)

Taken together, these results show that use of the candidate anti-idiotype antibody (clone 8) allows for specific and accurate assessment of expression of the exemplary anti-GPRC5D CAR in a cartridge-based flow system.

Example 4: Detecting CAR-T Cells In Vivo Using Candidate Anti-ID Antibody

The ability of a candidate anti-idiotype antibody (clone 8) to detect CAR-T cells in vivo was assessed. Cells from the OPM-2 multiple myeloma (MM) cell line were engineered to express green fluorescent protein and red-shifted Italian firefly luciferase. After harvest, $2\times10^6$ engineered OPM-2 cells were injected intravenously into immune-deficient mice via tail vein. Fourteen days later, mice were administered intravenously via tail vein either approximately $5\times10^5$, $1\times10^6$, or $2\times10^6$ human CD4+ and CD8+ T cells engineered to express the exemplary anti-GPRC5D CAR. On days 7, 14, 21, and 28 post CAR-T cell treatment, approximately 200 µL of blood was collected via retro-orbital sinus from the treated, anesthetized mice. The blood samples were then assessed for the presence of administered CAR-T cells by staining with an antibody cocktail that included fluorophore-conjugated anti-ID clone 8. Flow cytometry events were collected on a flow cytometer and analyzed.

Table E6 shows the mean count/µL of anti-GPRC5D CAR-expressing cells detected in blood using anti-ID clone 8 at days 7, 14, 21, or 28 post CAR-T cell treatment. Per treatment group, the values shown in Table E6 are the mean and standard deviation (SD) across four animals.

TABLE E6

| Quantification of CAR-T Cells in Peripheral Blood of Mice Treated With T Cells Expressing Anti-GPRC5D CAR | | | | |
|---|---|---|---|---|
| CAR-T Cell Dose | Day 7 Mean (SD) of Count/µL | Day 14 Mean (SD) of Count/µL | Day 21 Mean (SD) of Count/µL | Day 28 Mean (SD) of Count/µL |
| $5 \times 10^5$ Cells | 1.93 (0.57) | 4.70 (2.47) | 0.474 (0.327) | 0.106 (0.064) |
| $1 \times 10^6$ Cells | 9.82 (4.22) | 13.38 (6.39) | 1.62 (1.19) | 0.769 (1.010) |
| $2 \times 10^6$ Cells | 18.36 (12.51) | 16.28 (7.87) | 2.03 (0.93) | 2.74 (3.98) |

These results indicate that candidate anti-idiotype antibody clone 8 can be used to detect and quantify T cells expressing the anti-GPRC5D CAR in vivo.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. An anti-idiotype antibody or antigen-binding fragment thereof that binds to an anti-GPRC5D target antibody or antigen-binding fragment thereof, wherein the anti-idiotype antibody or antigen-binding fragment thereof comprises:

a VH region comprising a heavy chain complementarity-determining region 1 (CDR-H1) comprising the amino acid sequence set forth in SEQ ID NO: 15, a CDR-H2 comprising the amino acid sequence set forth in SEQ ID NO: 16, and a CDR-H3 comprising the amino acid sequence set forth in SEQ ID NO: 17; and a VL region comprising a light chain complementarity-determining region 1 (CDR-L1) comprising the amino acid sequence set forth in SEQ ID NO: 22, a CDR-L2 comprising the amino acid sequence set forth in SEQ ID NO: 23, and a CDR-L3 comprising the amino acid sequence set forth in SEQ ID NO: 24.

2. An anti-idiotype antibody or antigen-binding fragment thereof that binds to an anti-GPRC5D target antibody or antigen-binding fragment thereof, wherein the anti-idiotype antibody or antigen-binding fragment thereof comprises:

a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 25; and a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 26.

3. The anti-idiotype antibody or antigen-binding fragment thereof of claim 1, wherein:

the VH region comprises an amino acid sequence having at least 90% sequence identity to the amino acid sequence set forth in SEQ ID NO: 25; and the VL region comprises an amino acid sequence having at least 90% sequence identity to the amino acid sequence set forth in SEQ ID NO: 26.

4. The anti-idiotype antibody or antigen-binding fragment thereof of claim 1, wherein:

the VH region comprises the amino acid sequence set forth in SEQ ID NO: 25; and the VL region comprises the amino acid sequence set forth in SEQ ID NO: 26.

5. The anti-idiotype antibody or antigen-binding fragment thereof of claim 1, which is an intact antibody or full-length antibody.

6. The anti-idiotype antibody or antigen-binding fragment thereof of claim 1, wherein the anti-idiotype antibody or antigen-binding fragment thereof comprises:

a heavy chain comprising an amino acid sequence having at least 90% sequence identity to the amino acid sequence set forth in SEQ ID NO: 27; and a light chain comprising an amino acid sequence having at least 90% sequence identity to the amino acid sequence set forth in SEQ ID NO: 28.

7. The anti-idiotype antibody or antigen-binding fragment thereof of claim 1, wherein the anti-idiotype antibody or antigen-binding fragment thereof comprises:

a heavy chain comprising an amino acid sequence set forth in SEQ ID NO: 27; and a light chain comprising an amino acid sequence set forth in SEQ ID NO: 28.

8. The anti-idiotype antibody or antigen-binding fragment thereof of claim 1, which is an antigen-binding fragment.

9. The anti-idiotype antibody or antigen-binding fragment thereof of claim 8, wherein the antigen-binding fragment is selected from among Fab fragments, F(ab')2 fragments, Fab' fragments, Fv fragments, an scFv, and a single domain antibody.

10. The anti-idiotype antibody or antigen-binding fragment thereof of claim 1, wherein the anti-GPRC5D target antibody or antigen-binding fragment thereof comprises a VH region comprising the amino acid sequence set forth in SEQ ID NO: 7, and a VL region comprising the amino acid sequence set forth in SEQ ID NO: 8.

11. The anti-idiotype antibody or antigen-binding fragment thereof of claim 10, wherein the anti-GPRC5D target antibody or antigen binding fragment is a single chain variable fragment (scFv).

12. The anti-idiotype antibody or antigen-binding fragment thereof of claim 11, wherein the scFv comprises the amino acid sequence set forth in SEQ ID NO: 9.

13. The anti-idiotype antibody or antigen-binding fragment thereof of claim 1, wherein the anti-idiotype antibody or antigen-binding fragment thereof binds the anti-GPRC5D target antibody or antigen-binding fragment thereof comprised within or included in an antigen-binding domain of an extracellular portion of a CAR.

14. The anti-idiotype antibody or antigen-binding fragment thereof of claim 1, wherein the anti-idiotype antibody or antigen-binding fragment thereof is an agonist of a CAR comprising the anti-GPRC5D target antibody or antigen-binding fragment thereof.

15. A conjugate, comprising the anti-idiotype antibody or antigen-binding fragment thereof of claim 1 and a heterologous molecule or moiety.

16. A conjugate, comprising the anti-idiotype antibody or antigen-binding fragment thereof of claim 2 and a heterologous molecule or moiety.

17. A nucleic acid molecule(s) encoding the heavy chain and/or the light chain of the anti-idiotype antibody or antigen-binding fragment thereof of claim 1.

18. A nucleic acid molecule(s) encoding the heavy chain and/or the light chain of the anti-idiotype antibody or antigen-binding fragment thereof of claim 2.

19. A vector, comprising the nucleic acid molecule(s) of claim 17.

20. A cell, comprising the nucleic acid molecule(s) of claim 17.

21. A method of producing an anti-idiotype antibody or antigen-binding fragment thereof, comprising:

expressing the heavy and/or light chain encoded by the nucleic acid molecule(s) of claim 17 in a suitable host cell; and recovering or isolating the antibody.

22. A method of producing an anti-idiotype antibody or antigen-binding fragment thereof, comprising:

culturing the cell of claim 20 under conditions in which the heavy chain and/or light chain is expressed; and recovering or isolating the antibody.

23. A composition, comprising the anti-idiotype antibody or antigen-binding fragment thereof of claim 1 or a conjugate comprising the anti-idiotype antibody or antigen-binding fragment thereof of claim 1 and a heterologous molecule or moiety.

24. A method of detecting a target antibody or antigen-binding fragment thereof, comprising:

(a) contacting a composition comprising a target antibody or antigen-binding fragment thereof with the anti-idiotype antibody or antigen-binding fragment thereof of claim 1 or a conjugate comprising the anti-idiotype antibody or antigen-binding fragment thereof of claim 1 and a heterologous molecule or moiety, wherein the anti-idiotype antibody or antigen-binding fragment thereof specifically binds to the target antibody or antigen-binding fragment thereof; and (b) detecting the anti-idiotype antibody bound to the target antibody or antigen-binding fragment thereof.

25. The method of claim 24, wherein the target antibody or antigen-binding fragment thereof is bound to a cell or expressed on the surface of a cell, and the detecting in (b) comprises detecting cells bound with the anti-idiotype antibody or antigen-binding fragment thereof, and wherein the cell expresses on its surface a CAR comprising the target antibody or antigen-binding fragment thereof.

26. The method of claim 25, wherein the cell expresses on its surface a CAR comprising the target antibody or antigen-binding fragment thereof.

27. A method of detecting a target antibody or antigen-binding fragment thereof, comprising:

(a) contacting a composition comprising a target antibody or antigen-binding fragment thereof with the anti-idiotype antibody or antigen-binding fragment thereof of claim 2 or a conjugate comprising the anti-idiotype antibody or antigen-binding fragment thereof of claim 2 and a heterologous molecule or moiety, wherein the anti-idiotype antibody or antigen-binding fragment thereof specifically binds to the target antibody or antigen-binding fragment thereof; and (b) detecting the anti-idiotype antibody bound to the target antibody or antigen-binding fragment thereof.

28. A method of selecting cells from a cell population, comprising:

(a) contacting a cell population expressing a CAR comprising a target antibody or antigen-binding fragment thereof or a cell bound to a target antibody or antigen-binding fragment thereof with the anti-idiotype antibody or antigen-binding fragment thereof of claim 1 or a conjugate comprising the anti-idiotype antibody or antigen-binding fragment thereof of claim 1 and a heterologous molecule or moiety, wherein the anti-idiotype antibody or antigen-binding fragment thereof specifically binds to the target antibody or antigen-binding fragment thereof; and (b) selecting cells bound with the anti-idiotype antibody or antigen-binding fragment thereof.

29. A method of stimulating cells, comprising incubating an input composition comprising cells expressing a CAR comprising a target antibody or antigen-binding fragment thereof with the anti-idiotype antibody or antigen-binding fragment thereof of claim 1 or a conjugate comprising the anti-idiotype antibody or antigen-binding fragment thereof of claim 1 and a heterologous molecule or moiety, wherein the anti-idiotype antibody or antigen-binding fragment thereof specifically binds to the target antibody or antigen-binding fragment thereof, thereby generating an output composition comprising stimulated cells.

30. A method of producing a cell composition, comprising:

(a) introducing into cells a nucleic acid molecule(s) encoding a CAR, thereby generating an input composition; and (b) incubating the input composition with the anti-idiotype antibody or antigen-binding fragment thereof of claim 1 or a conjugate comprising the anti-idiotype antibody or antigen-binding fragment thereof of claim 1 and a heterologous molecule or moiety, wherein the anti-idiotype antibody or antigen-binding fragment thereof specifically binds to an antigen receptor of the CAR, thereby producing the cell composition.

31. A method of purifying an anti-idiotype antibody or antigen-binding fragment thereof, comprising:

(a) contacting a composition comprising a target antibody or antigen-binding fragment thereof with the anti-idiotype antibody or antigen-binding fragment thereof of claim 1 or a conjugate comprising the anti-idiotype antibody or antigen-binding fragment thereof of claim 1 and a heterologous molecule or moiety, wherein the anti-idiotype antibody or antigen-binding fragment thereof specifically binds to the target antibody or antigen-binding fragment thereof; and (b) isolating complexes comprising the anti-idiotype antibody or antigen-binding fragment thereof.

32. A method of depleting cells, comprising administering, to a subject, a composition comprising the anti-idiotype antibody or antigen-binding fragment thereof of claim 1 or a conjugate comprising the anti-idiotype antibody or antigen-binding fragment thereof of claim 1 and a heterologous molecule or moiety, wherein the anti-idiotype antibody or antigen-binding fragment thereof specifically binds to a target antibody or antigen-binding fragment thereof, wherein the subject has been administered a cell expressing a CAR comprising the target antibody or antigen-binding fragment thereof.

* * * * *